US008653307B2

(12) United States Patent
Stoltz et al.

(10) Patent No.: US 8,653,307 B2
(45) Date of Patent: Feb. 18, 2014

(54) LIPHAGAL ENANTIOMERS AND THEIR DERIVATIVES AND PRECURSORS, AND ENANTIOSELECTIVE METHODS OF MAKING THE SAME

(75) Inventors: Brian M Stoltz, San Marino, CA (US); Ryan McFadden, Foster City, CA (US); Scott C. Virgil, Pasadena, CA (US); Helene Kolding, Lyngby (DK); Jennifer L Alleva, Princeton, NJ (US); Joshua J Day, Fort Collins, CO (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/485,835

(22) Filed: May 31, 2012

(65) Prior Publication Data

US 2013/0023676 A1 Jan. 24, 2013

Related U.S. Application Data

(60) Provisional application No. 61/491,631, filed on May 31, 2011.

(51) Int. Cl.
C07C 49/00 (2006.01)
(52) U.S. Cl.
USPC ............................................. 568/373; 568/374
(58) Field of Classification Search
USPC ................................................. 568/373, 374
See application file for complete search history.

(56) References Cited

FOREIGN PATENT DOCUMENTS

WO WO 2006/081659 A1 8/2006

OTHER PUBLICATIONS

Marion et al. Organic Letters, 2006, 8 (2), 321-324.*
Miyaoka et al. Chemical & Pharmaceutical Bulletin (1989), 37(10), 2882-3.*
Tobe et al. J. Org. Chem. 1981,46, 5009-5011.*
Abad et al. J. Chem. Soc. Perkin Trans. 1 1993 1861-1867.*
Tsuji et al. J. Am. Chem. Soc. 2003, 125, 951-961.*
International Search Report and the Written Opinion of the International Searching Authority, or the Declaration, dated Jan. 30, 2013, for International application No. PCT/US2012/040310, 9 pages.
Alvarez-Manzaneda, et al., "Enantioselective Total Synthesis of the Selective PI3 Kinase Inhibitor Liphagal", Organic Letters, 2010, vol. 12, No. 20, pp. 4450-4453; American Chemical Society.
Behenna, et al., "The Enantioselective Tsuji Allylation", Journal of the American Chemical Society, 2004, vol. 126, pp. 15044-15045; American Chemical Society.
Bélanger, et al., "Enantioselective Pd-Catalyzed Allylation Reaction of Fluorinated Silyl Enol Ethers", Journal of the American Chemical Society, 2007, vol. 129, pp. 1034-1035; American Chemical Society.
Bélanger, et al., "Unexpected Effect of the Fluorine Atom on the Optimal Ligand-to-Palladium Ratio in the Enantioselective Pd-Catalyzed Allylation Reaction of Fluorinated Enol Carbonates", Chem. Commun., 2008, pp. 3251-3253; The Royal Society of Chemistry.
Bélanger, et al., "Use of 5,5-(Dimethyl)-i-Pr-PHOX as a Practical Equivalent to t-Bu-PHOX in Asymmetric Catalysis", Organic Letters, 2009, vol. 11, No. 10, pp. 2201-2204; American Chemical Society.
Birkett, et al., "A New Approach to Dihydrobenzofurans and Dihydrobenzopyrans (Chromans) Based on the Intramolecular Trapping by Alcohols of Benzynes Generated from 7-Substituted-1-aminobenzotriazoles", Tetrahedron, 2000, vol. 56, pp. 1013-1023; Elsevier Sciences Ltd.
Braun, et al., "Tsuji-Trost-Allylierung mit Ketonenolaten", Angewandte Chemie, 2006, vol. 118, pp. 7106-7109; Wiley-VCH Verlag GmbH & Co. KGaA, Wienheim.
Braun, et al, "Tsuji-Trust Allylic Alkylation with Ketone Enolates", Angewandte Chemie Internet Edition, 2006, vol. 45, pp. 6952-6955; Wiley-VCH Verlag GmbH, Weinheim.
Braun, et al., "Diastereoselecktive und Enantioselektive Palladium-katalysierte Allylsubstitution mit nicht Stabilisierten Ketonenolaten", Angewandte Chemie, 2000, vol. 112, Nr. 19, pp. 3637-3640; Wiley-VCH Verlag GmbH, Weinheim.
Braun, et al., "Diastereoselective and Enantioselective Palladium-Catalyzed Allylic Substitution with Nonstabilized Ketone Enolates", Angewandte Chemie Internet Edition, 2000, vol. 39, No. 19, pp. 3494-3497; Wiley-VCH Verlag GmbH, Weinheim.
Braun, et al., "New Developments in Stereoselective Palladium-Catalyzed Allylic Alkylations of Preformed Enolates", Synlett, 2006, No. 5, pp. 661-676; Georg Thieme Verlag Stuttgart, New York.
Braun, et al., "Palladium-Catalyzed Diastereoselective and Enantioselective Allylic Alkylations of Ketone Enolates", Adv. Synth. Catal., 2008, vol. 350, pp. 303-314; Wiley-VCH Verlag GmbH & Co. KGaA, Weinheim.
Burchat, et al., "Titration of Alkyllithiums with a Simple Reagent to a Blue Endpoint", Journal of Organometallic Chemistry, 1997, vol. 542, pp. 281-283; Elsevier Science S.A.
Burger, et al., "Catalytic Asymmetric Synthesis of Cyclic α-Alkylated α-Fluoroketones", Synlett, 2006, No. 17, pp. 2824-2826; Georg Thieme Verlag Stuttgart, New York.
Cantley, "The Phosphoinositide 3-Kinase Pathway", Science, May 31, 2002, vol. 296, pp. 1655-1657.
Cargill, et al., "Acid-Catalyzed Rearrangements of β,γ-Unsaturated Ketones", Accounts of Chemical Research, 1974, vol. 7, pp. 106-113.
Carril, et al., "On-Water Chemistry: Copper-Catalyzed Straightforward Synthesis of Benzo[b]furan Derivatives in Neat Water", Organic Letters, 2006, vol. 8, No. 7, pp. 1467-1470; American Chemical Society.
Deore, et al., "Efficient Synthesis of Key Intermediate Toward Liphagal Synthesis," Synthetic Communications, 2011, vol. 41, pp. 177-183; Taylor & Francis Group, LLC.
Engelman, et al., "The Evolution of Phosphatidylinositol 3-Kinases as Regulators of Growth and Metabolism", Nature Reviews, Genetics, Aug. 2006, vol. 7, pp. 606-619; Nature Publishing Group.

(Continued)

Primary Examiner — Nizal Chandrakumar
(74) Attorney, Agent, or Firm — Ropes & Gray LLP; David P. Halstead; David P. Pleynet

(57) ABSTRACT

Enantioenriched compositions of liphagal and its derivatives and precursors include more than 50 mol % of a first enantiomer based on the total amount of a first and a second enantiomer. A method of making an enantioenriched composition includes catalytic enantioselective alkylation, ring expansion, and intramolecular aryne cyclization.

9 Claims, No Drawings

(56) References Cited

OTHER PUBLICATIONS

Enquist, Jr., et al., "The Total Synthesis of (−)-cyanthiwigin F by Means of Double Catalytic Enantioselective Alkylation", *Nature*, Jun. 2008, vol. 453, pp. 1228-1231; Macmillan Publishers Limited.

George, et al., Enantiospecific, Biosynthetically Inspired Formal Total Synthesis of (+)-Liphagal, *Organic Letters*, 2010, vol. 12, No. 10, pp. 2394-2397; American Chemical Society.

Hixson, et al., "The Di-π-methane and Oxa-di-π-methane Rearrangements", *Chemical Reviews*, 1973, vol. 73, No. 5, pp. 531-551.

Kappe, "Controlled Microwave Heating in Modern Organic Synthesis", *Angewandte Chemie Internet Edition*, 2004, vol. 43, pp. 6250-6284; Wiley-VCH Verlag GmbH & Co. KGaA, Weinheim.

Kawatsura, et al., "Simple, Highly Active Palladium Catalysts for Ketone and Malonate Arylation: Dissecting the Importance of Chelation and Steric Hindrance", *Journal of the American Chemical Society*, 1999, vol. 121, pp. 1473-1478; American Chemical Society.

Kazmaier, "Palladium Catalyzed Allylic Alkylations of Nonstabilized Enolates", *Current Organic Chemistry*, 2003, vol. 7, pp. 317-328; Bentham Science Publishers Ltd.

Keith, et al., "The Inner-Sphere Process in the Enantioselective Tsuji Allylation Reaction with (S)-t-Bu-phosphinooxazoline Ligands", *Journal of the Chemical Society*, 2007, vol. 129, pp. 11876-11877.

Krout, et al., "Preparation of (S)-*tert*-ButylPHOX (Oxazole, 4-(1,1-dimethylethyl)-2-[2-(diphenylphosphino)phenyl]-4,5-dihydro-(4S)-)", *Organic Syntheses*, 2009, vol. 86, pp. 181-193.

Levine, et al., "Catalytic Enantioselective Approach to the Eudesmane Sesquiterpenoids: Total Synthesis of (+)-Carissone", *Organic Letters*, 2009, vol. 11, No. 2, pp. 289-292; American Chemical Society.

Marion, et al., "Liphagal, a Selective Inhibitor of PI3 Kinase α Isolated from the Sponge *Aka coralliphaga*: Structure Elucidation and Biomimetic Synthesis", *Organic Letters*, 2006, vol. 8, No. 2, pp. 321-324.

McDougal, et al., "High-Throughput Screening of the Asymmetric Decarboxylative Alkylation Reaction of Enolate-Stabilized Enol Carbonates", *Synlett*, 2010, No. 11, pp. 1712-1716; Georg Thieme Verlag Stuttgart, New York.

McFadden, et al., "The Catalytic Enantioselective, Protecting Group-Free Total Synthesis of (+)-Dichroanone", *Journal of the American Chemical Society*, 2006, vol. 128, pp. 7738-7739.

Mehta, et al., "A Concise Synthesis of the Bioactive Meroterpenoid Natural Product (±)-Liphagal, a Potent PI3K Inhibitor", *Tetrahedron Letters*, 2009, vol. 50, pp. 5260-5262; Elsevier Ltd.

Miyaoka, et al., "A Method for Synthesizing the Diformylcyclopentene Moiety of Halimedatrial", *Chem. Pharm. Bull.*, 1989, vol. 37, No. 10, pp. 2882-2883.

Mohr, et al., "Deracemization of Quaternary Stereocenters by Pd-Catalyzed Enantioconvergent Decarboxylative Allylation of Racemic β-Ketoesters", *Angewandte Chemie*, 2005, vol. 117, pp. 7084-7087; Wiley-VCH Verlag GmbH & Co. KGaA, Weinheim.

Mohr, et al., "Deracemization of Quaternary Stereocenters by Pd-Catalyzed Enantioconvergent Decarboxylative Allylation of Racemic β-Ketoesters", *Angewandte Chemie Internet Edition*, 2005, vol. 44, pp. 6924-6927; Wiley-VCH Verlag GmbH & Co. KGaA, Weinheim.

Mohr, et al., "Enantioselective Tsuji Allylations", *Chemistry an Asian Journal*, 2007, vol. 2, pp. 1476-1491; Wiley-VCH Verlag GmbH & Co. KGaA, Weinheim.

Mohr, et al., "Preparation of (S)-2-Allyl-2-Methylcyclohexanone (Cyclohexanone, 2-methyl-2-(2-propen-1-yl)-, (2S)-)", *Organic Syntheses*, 2009, vol. 86, pp. 194-211.

Mukherjee, et al., "A Catalytic, Asymmetric Formal Synthesis of (+)-Hamigeran B", *Organic Letters*, 2011, vol. 13, No. 5, pp. 825-827; American Chemical Society.

Nakamura, et al., "Synthesis of Chiral α-Fluoroketones through Catalytic Enantioselective Decarboxylation", *Angewandte Chemie*, 2005, vol. 117, pp. 7414-7417; Wiley-VCH Verlag GmbH & co. KGaA, Weinheim.

Nakamura, et al., "Synthesis of Chiral α-Fluoroketones through Catalytic Enantioselective Decarboxylation", *Angewandte Chemie Internet Edition*, 2005, vol. 44, pp. 7248-7251;Wiley-VCH Verlag GmbH & co. KGaA, Weinheim.

Olah, et al., "Preparative Carbocation Chemistry. 13.[1] Preparation of Carbocations from Hydrocarbons via Hydrogen Abstraction with Nitrosonium Hexafluorophosphate and Sodium Nitrite-Trifluoromethanesulfonic Acid", *Journal of Organic Chemistry*, 1978, vol. 43, No. 1, pp. 173-175.

Pereira, et al., "Synthesis of Phosphatidylinositol 3-Kinase (PI3K) Inhibitory Analogues of the Sponge Meroterpenoid Liphagal", *Journal of Medicinal Chemistry*, 2010, vol. 53, No. 24, pp. 8523-8533; American Chemical Society.

Petrova, et al., "Enantioselective Total synthesis of (+)-Cassiol", *Organic Letters*, 2009, vol. 11, No. 2, pp. 293-295; American Chemical Society.

Razin, et al., "Isomerization of Dymethyl exo,exo-1,3-Dipropyl-Bicyclo[1.1.0]Butane-2,4-Dicarboxylate Under the Action of $AlBr^{3}$", Translated from *Zhurnal Organicheskol Khimii*, Mar. 1968, vol. 4, No. 3, p. 535 (2 sheets).

Samuels, et al., "High Frequency of Mutations of the *PIK3CA* Gene in Human Cancers", *Science*, Apr. 23, 2004, vol. 304, p. 554.

Schulz, et al., "Palladium-Catalyzed Synthesis of Substituted Cycloheptane-1,4-diones by an Asymmetric Ring-Expanding Allylation (AREA)", *Angewandte Chemie Internet Edition*, 2007, vol. 46, pp. 3966-3970; Wiley-VCH Verlag GmbH & Co., KGaA, Weinheim.

Schulz, et al., Palladiumkatalysierte Synthese von Substituierten Cycloheptan-1,4-dionen durch Asymmetrische, Ringerweiternde Allylierung (AREA), *Angewandte Chemie*, 2007, vol. 119, pp. 4040-4044; Wiley-VCH Verlag GmbH & Co., KGaA, Weinheim.

Seto, et al., "Catalytic Enantioselective Alkylation of Substituted Dioxanone Enol Ethers: Ready Access to C(α)-Tetrasubstituted Hydroxyketones, Acids, and Esters", *Angewandte Chemie*, 2008, vol. 120, pp. 6979-6982; Wiley-VCH Verlag GmbH & Co., KGaA, Weinheim.

Seto, et al., "Catalytic Enantioselective Alkylation of Substituted Dioxanone Enol Ethers: Ready Access to C(α)-Tetrasubstituted Hydroxyketones, Acids, and Esters", *Angewandte Chemie Internet Edition*, 2008, vol. 47, pp. 6873-6876; Wiley-VCH Verlag GmbH & Co., KGaA, Weinheim.

Sherden, et al., "Unusual Allylpalladium Carboxylate Complexes: Identification of the Resting State of Catalytic Enantioselective Decarboxylative Allylic Alkylation Reactions of Ketones", *Angewandte Chemie*, 2009, vol. 121, pp. 6972-6975; Wiley-VCH Verlag GmbH & Co. KGaA, Weinheim.

Sherden, et al., "Unusual Allylpalladium Carboxylate Complexes: Identification of the Resting State of Catalytic Enantioselective Decarboxylative Allylic Alkylation Reactions of Ketones", *Angewandte Chemie Internet Edition*, 2009, vol. 48, pp. 6840-6843; Wiley-VCH Verlag GmbH & Co. KGaA, Weinheim.

Streuff, et al., "A Palladium-Catalysed Enolate Alkylation Cascade for the Formation of Adjacent Quaternary and Tertiary Stereocentres", *Nature Chemistry*, Mar. 2010, vol. 2, pp. 192-196; Macmillan Publishers Limited.

Sundstrom, et al., "Inhibitors of Phosphoinositide-3-Kinase: A Structure-Based Approach to Understanding Potency and Selectivity", *Organic & Biomolecular Chemistry*, 2009, vol. 7, pp. 840-850; The Royal Society of Chemistry.

Trost, et al., "Regio- and Enantioselective Pd-Catalyzed Allylic Alkylation of Ketones through Allyl Enol Carbonates", *Journal of the American Chemical Society*, 2005, vol. 127, pp. 2846-2847; American Chemical Society.

Trost, et al, "Palladium-Catalyzed Asymmetric Allylic α-Alkylation of Acyclic Ketones", *Journal of the American Chemical Society*, 2005, vol. 127, pp. 17180-17181; American Chemical Society.

Trost, et al., "Catalytic Enantioselective Construction of All-Carbon Quaternary Stereocenters", *Synthesis*, 2006, No. 3, pp. 369-396.

Trost, et al., "Enantioselective Synthesis of α-Tertiary Hydroxyaldehydes by Palladium-Catalyzed Asymmetric Allylic Alkylation of Enolates", *Journal of the American Chemical Society*, 2007, vol. 129, pp. 282-283; American Chemical Society.

(56) References Cited

OTHER PUBLICATIONS

Trost, et al., "Asymmetric Allylic Alkylation of Cyclic Vinylogous Esters and Thioesters by Pd-Catalyzed Decarboxylation of Enol Carbonate and β-Ketoester Substrates", *Angewandte Chemie*, 2006, vol. 118, pp. 3181-3184.

Trost, et al., "Asymmetric Allylic Alkylation of Cyclic Vinylogous Esters and Thioesters by Pd-Catalyzed Decarboxylation of Enol Carbonate and β-Ketoester Substrates", *Angewandte Chemie Internet Edition*, 2006, vol. 45, pp. 3109-3112.

Trost, et al., "Palladium-Catalyzed Decarboxylative Asymmetric Allylic Alkylation of Enol Carbonates", *Journal of the American Chemical Society*, 2009, vol. 131, pp. 18343-18357; American Chemical Society.

Wakabayashi, et al., "Novel Products in the Reaction of 6-Cyanotricyclo[5.5.0.0$^{2.5}$]dodeca-3,6,9,12-tetraene with 2,3-Dichloro-5,6-dicyano-1,4-benzoquinone", *J Chem. Soc. Perkin Trans.*, 1990, pp. 1489-1490.

Ward, et al., "Therapeutic Potential of Phosphoinositide 3-Kinase Inhibitors", *Chemistry & Biology*, Mar. 2003, vol. 10, pp. 207-213; Elsevier Science Ltd.

Ward, et al., "Isoform-Specific Phosphoinositide 3-Kinase Inhibitors as Therapeutic Agents", *Current Opinion in Pharmacology*, 2003, vol. 3, pp. 426-434; Elsevier Ltd.

White, et al., "The Catalytic Asymmetric Total Synthesis of Elatol", *Journal of the American Chemical Society*, 2008, vol. 130, pp. 810-811; American Chemical Society.

White, et al., "A General Enantioselective Route to the Chamigrene Natural Product Family", *Tetrahedron*, 2010, vol. 66, pp. 4668-4686; Elsevier Ltd.

Yan, et al., "Highly Enantioselective Pd-Catalyzed Allylic Alkylations of Acyclic Ketones", *Angewandte Chemie*, 2005, vol. 117, pp. 6702-6704; Wiley-VCH Verlag GmbH & Co. KGaA, Weinheim.

Yan, et al., "Highly Enantioselective Pd-Catalyzed Allylic Alkylations of Acyclic Ketones", *Angewandte Chemie Internet Edition*, 2005, vol. 44, pp. 6544-6546; Wiley-VCH Verlag GmbH & Co. KGaA, Weinheim.

You, et al., "Enantioselektive Palladium-Katalysierte Decarboxylierende Allylische Alkylierungen", *Angewandte Chemie*, 2006, vol. 118, pp. 5372-5374; Wiley-VCH Verlag GmbH & Co. KGaA, Weinheim.

You, et al., "Enantioselective Palladium-Catalyzed Decarboxylative Allylic Alkylations", *Angewandte Chemie Internet Edition*, 2006, vol. 45, pp. 5246-5248; Wiley-VCH Verlag GmbH & Co. KGaA, Weinheim.

Zhang, et al., "Synthetic and Computational Studies on Liphagal: A Natural Product Inhibitor of PI-3K", *Tetrahedron Letters*, 2010, vol. 51, pp. 6120-6122; Elsevier Ltd.

Zhao, et al., "Enamines: Efficient Nucleophiles for the Palladium-Catalyzed Asymmetric Allylic Alkylation", *Tetrahedron*, 2009, vol. 65, pp. 512-517; Elsevier Ltd.

Zheng, W., et al., "Highly Regio-, Diastereo-, and Enantioselective Pd-Catalyzed Allylic Alkylation of Acyclic Ketone Enolates with Monosubstituted Allyl Substrates", *Journal of the American Chemical Society*, 2007, vol. 129, pp. 7718-7719.

Zuend, et al., "Scaleable Catalytic Asymmetric Strecker Syntheses of Unnatural α-Amino Acids", *Nature*, Oct. 2009, vol. 461, pp. 968-971; Macmillan Publishers Limited.

\* cited by examiner

LIPHAGAL ENANTIOMERS AND THEIR DERIVATIVES AND PRECURSORS, AND ENANTIOSELECTIVE METHODS OF MAKING THE SAME

CROSS-REFERENCE TO RELATED APPLICATION

This application claims priority to and the benefit of U.S. Provisional Patent Application Ser. No. 61/491,631 filed on May 31, 2011, the entire content of which is incorporated herein by reference.

STATEMENT OF FEDERAL SUPPORT

This invention was made with government support under Grant No. GM080269 awarded by the National Institutes of Health. The government has certain rights in the invention.

TECHNICAL FIELD

Embodiments of the present invention are directed to liphagal enantiomers, derivatives thereof and precursors thereto, and to enantioselective methods of making the same.

BACKGROUND

Phosphatidylinositol 3-kinases participate in the regulation of numerous biological functions and have been directly implicated in the pathogensis of diabetes and cancer. Indeed, the PI3K family of enzymes is intimately involved in numerous cellular pathways spanning proliferation, survival, adhesion, movement, differentiation, membrane trafficking, glucose transport, neurite outgrowth, and superoxide production in cells. Many natural and synthetic inhibitors of PI3K's are known, for example, myricetin, quercetin, resveratrol, staurosporine, viridin, wortmannin, and liphagal (all shown below) but selective inhibition of an individual isoform is rare. As the human genome has numerous kinases, the selective inhibition of one isoform of PI3K, for example, PI3Kα (a lipid kinase isoform that holds a central role in several cancers), would be particularly beneficial. For instance, selective inhibitors of individual isoforms of these enzymes would allow for the targeting of specific diseases spanning cancer, cardiovascular disease, and autoimmune disorders.

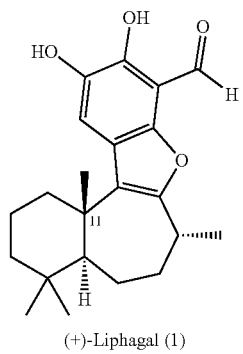

(+)-Liphagal (1)

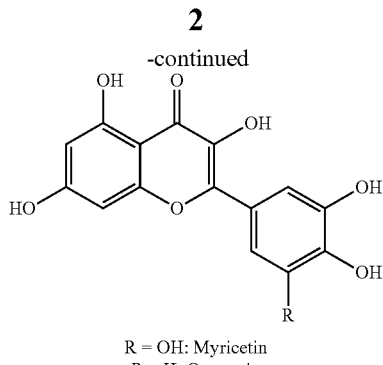

R = OH: Myricetin
R = H: Quercetin

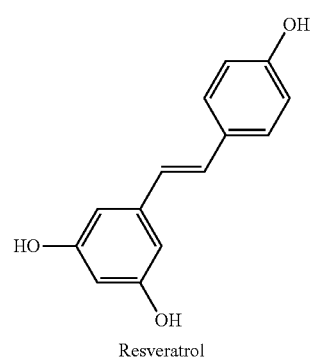

Resveratrol

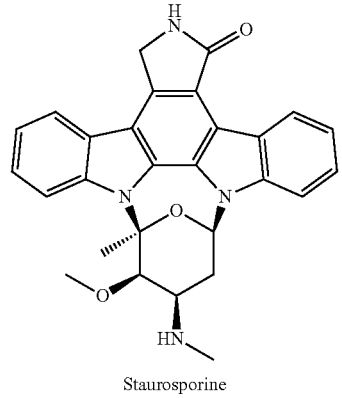

Staurosporine

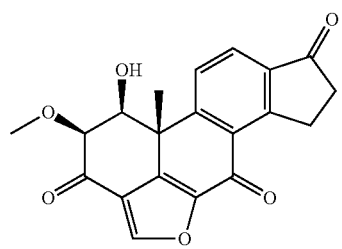

Viridin

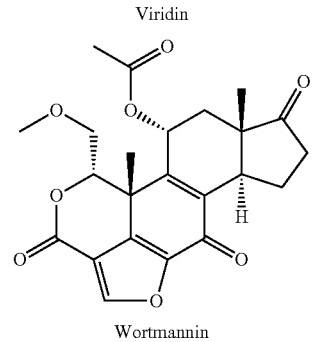

Wortmannin

Liphagal (the (+) enantiomer shown as compound 271 below), in the racemic form, has an $IC_{50}$ of 100 nM against PI3Kα, and is at least 10-fold more potent against this isoform of the enzyme compared to any other PI3K, including the γ isoform. While other natural and synthetic inhibitors of PI3Ks are known, they do not show the same selective inhibition of the PI3Kαisoform as liphagal does in the racemic form, and they do not possess the same potency. For example, although the natural product wortmannin (compound 273 shown below) shows an $IC_{50}$ of 12 nM toward PI3Kα, it has nearly equal potency against several other related enzymes. Additionally, quercitin (compound 274 shown below) and other molecules have been used in chemical genetics studies to understand the roles of certain PI3K's in cell signaling. Second generation synthetic molecules designed to mimic natural products (e.g., LY294002 (compound 275 shown below)) have also been developed and studied by the pharmaceutical industry. Though somewhat selective, molecules such as LY294002 (compound 275 shown below) lack the potency of liphagal (the (+) enantiomer shown as compound 271 below).

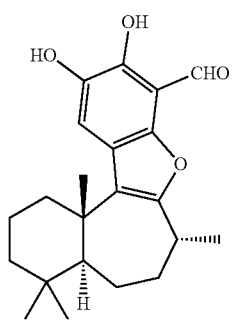

Liphagal (271)

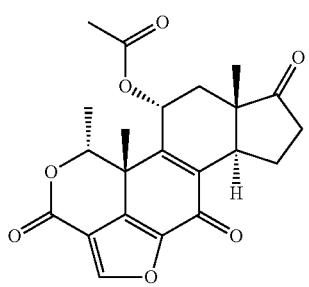

Wortmannin (273)

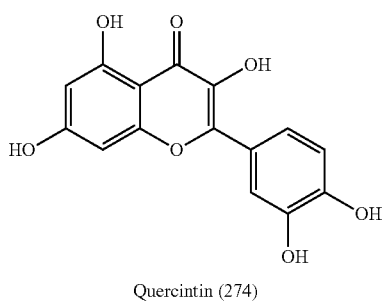

Quercintin (274)

-continued

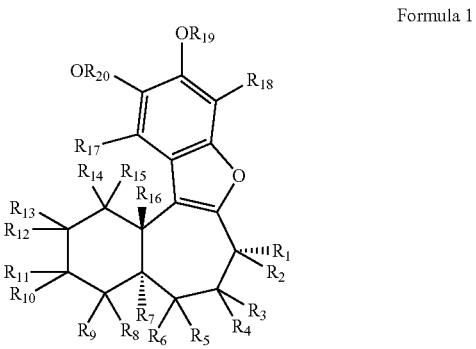

LY294002 (275)

With its unique biological activity and potentially novel mode of action, liphagal shows promise in the development of new therapeutics and as a chemical tool for studying cellular signaling and disease states. Additionally, liphagal (in the racemic form) displays substantial cytotoxicity toward various cancer cell lines. Against LoVo (human colon) cells, liphagal (in the racemic form) displays an $IC_{50}$ of 0.58 µM, and against another cell line, CaCo (human colon), liphagal (in the racemic form) displays an $IC_{50}$ value of 0.67 µM. Also, liphagal (in the racemic form) shows some cytotoxicity toward the MDA-468 breast cancer line, i.e., and $IC_{50}$ value of 1.58 µM.

From a structural perspective, liphagal is a tetracyclic meroterpenoid having an unprecedented [6-7-5-6] tetracyclic skeleton and has attracted significant attention from the synthetic organic community. While syntheses for the production of a racemic mixture of (±)-liphagal have been reported, no enantioselective method has been reported to date.

SUMMARY

According to some embodiments of the present invention, an enantioenriched composition includes a first enantiomer and optionally a second enantiomer. The first enantiomer is present in an amount greater than 50 mol % based on an amount of the first and second enantiomers, and the second enantiomer is present in an amount of about 0 to about less than 50 mol % based on the amount of the first and second enantiomers. The first and second enantiomers are (+) and (−) enantiomers of one another, and the first enantiomer is selected from compounds represented by Formulae 1 through 22.

Formula 1

-continued
Formula 2
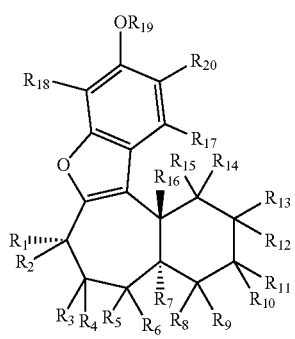
Formula 3
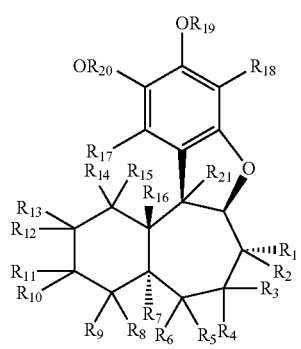
Formula 4
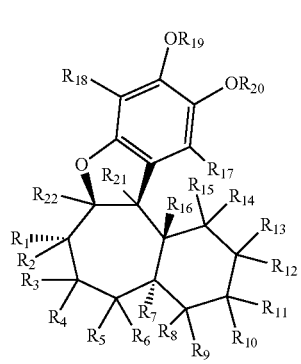
Formula 5
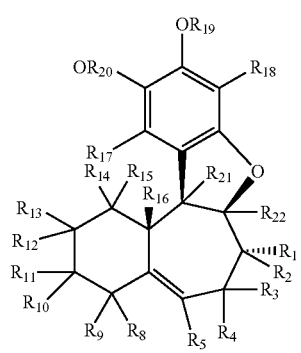
-continued
Formula 6
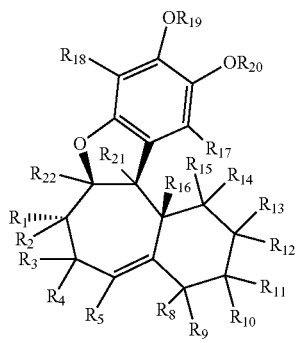
Formula 7
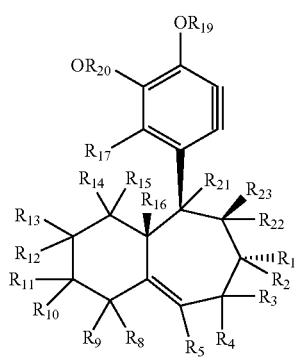
Formula 8
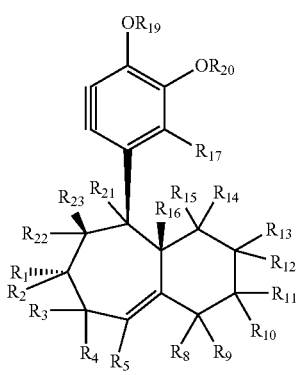
Formula 9
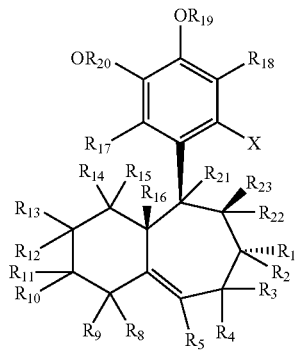

Formula 10
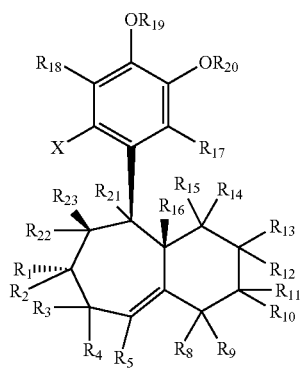
Formula 11
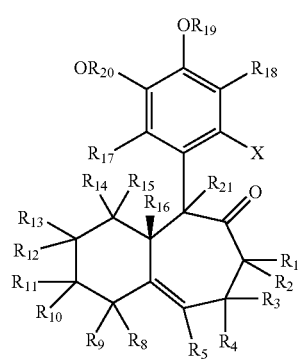
Formula 12
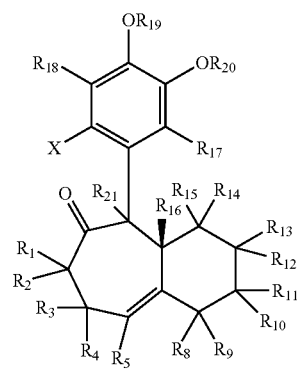
Formula 13
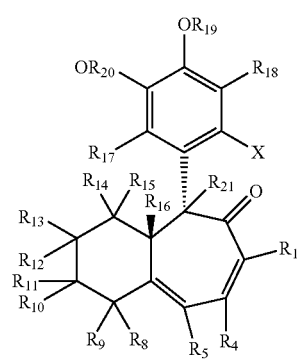
Formula 14
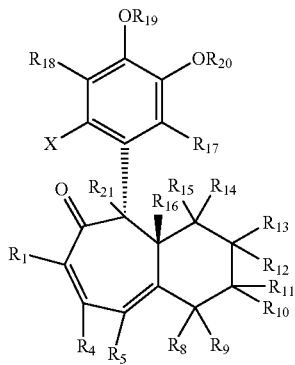
Formula 15
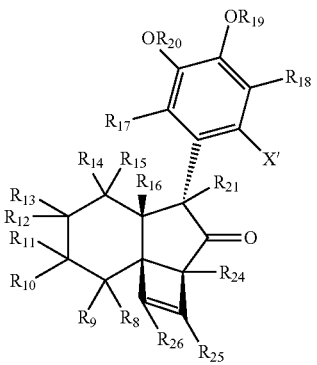
Formula 16
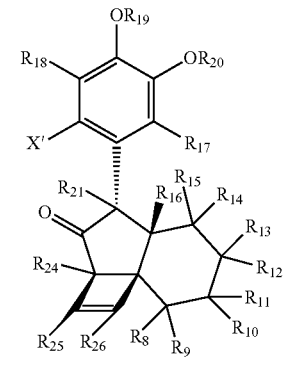
Formula 17
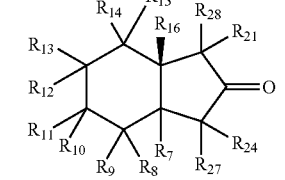
Formula 18
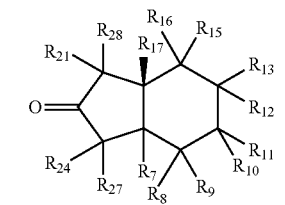

-continued

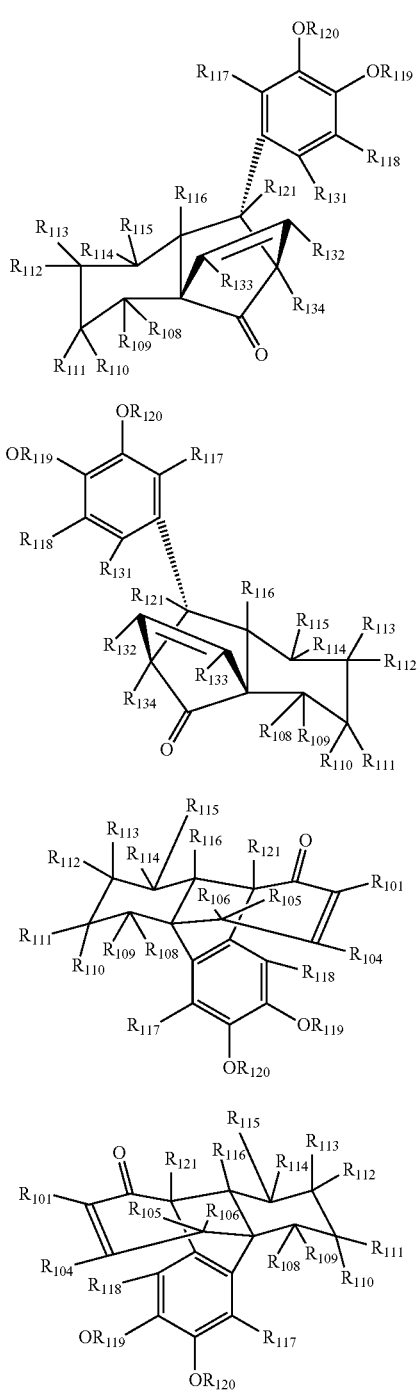

Formula 19

Formula 20

Formula 21

Formula 22

In Formulae 1 though 22, each of $R_1$ through $R_{30}$, $R_{101}$ through $R_{121}$, $R_{131}$ through $R_{134}$ and $R_{200}$ through $R_{204}$ is independently selected from hydrogen, substituted or unsubstituted hydrocarbyl groups, substituted or unsubstituted heteroatom containing hydrocarbyl groups, or functional groups, and two or more adjacent R groups may optionally combine to form a ring or a double bond. X is a halogen, and X' is hydrogen or a halogen.

According to other embodiments of the present invention, a method of making an enantioenriched composition includes enantioselective catalytic alkylation of a first precursor compound to form a second precursor compound; oxidation and condensation of the second precursor compound to form a third precursor compound; promotion of a photocycloaddition reaction of the third precursor compound to form a fourth precursor compound; exposure of the fourth precursor compound to a Lewis acid to form a fifth precursor compound; arylation of the fifth precursor compound to form a sixth precursor compound; functionalization of an aromatic group on the sixth precursor compound to form a seventh precursor compound; ring expansion of the seventh precursor compound to form an eighth precursor compound; reduction of the eighth precursor compound to form a ninth precursor compound; reduction of steric congestion in the ninth precursor compound to form a tenth precursor compound; intramolecular aryne cyclization of the tenth precursor compound to form a thirteenth precursor compound; stereoselective hydrogenation or substitution of the thirteenth precursor compound to form a fourteenth precursor compound; and oxidation of the fourteenth precursor compound to form a fifteenth compound.

The method may further include functionalization of the fifteenth precursor compound to form a compound of Formula 1, and/or demethylation (or desubstitution) of the compound of Formula 1 (or the fifteenth precursor compound) to yield a different compound of Formula 1. For example, demethylation (or desubstitution) of the fifteenth precursor compound could result in the formation of a compound of Formula 1 in which all of $R_{18}$, $R_{19}$ and $R_{20}$ are hydrogen. Also, in some embodiments, the intramolecular aryne cyclization includes stereoselective substitution of the tenth precursor to form an eleventh precursor; reduction of the eleventh precursor to form a twelfth precursor; and exposure of the twelfth precursor to a strong base to form the thirteenth precursor. Additionally, reduction of the steric congestion may be accomplished by epimerization of an aryl substituent of the ninth precursor compound to form the tenth precursor compound.

DETAILED DESCRIPTION

The potent biological activity of liphagal has prompted more than one attempt at its total synthesis. However, the complex tetracyclic structure of liphagal, which is highlighted by a chiral quaternary carbon center at C(11), makes total synthesis a significant challenge. Additionally, while syntheses of a racemic form of liphagal have been reported, these syntheses are not enantioselective, i.e., they produce compositions including an equal mixture of the (+) and (−) enantiomers. While it is not yet know which of the (+) and (−) enantiomers of liphagal shows the most bioactivity, those of ordinary skill in the art readily recognize that it is uncommon for both enantiomers of a compound to show bioactivity (or the same degree of bioactivity). As such, an enantioselective synthesis of either (or both of) the (+) or the (−) enantiomer(s) of liphagal would not only enable the determination of which enantiomer is bioactive (or the most bioactive), but would enable the production of an enantiomerically pure (or substantially enantiomerically pure, i.e., about 95 wt % to about 100 wt % of the desired enantiomer) composition, the development of derivatives that would potentially also be biologically active, and the development of precursors to the liphagal enantiomers and derivatives that would be useful in the production of the enantiomers and derivatives as well as other products.

According to embodiments of the present invention, a composition includes a major amount of a first enantiomer and a minor amount of a second enantiomer. As used herein, the term "major amount" denotes an amount of the first enantiomer that is greater than the amount of the second enantiomer, and a major amount is any amount greater than 50 mol %. Conversely, the term "minor amount," as used herein, denotes an amount of the second enantiomer that is less than the amount of the first enantiomer, and a minor amount is any amount less than 50 mol %. In particular, these compositions are intended to exclude racemic mixtures of the first and second enantiomers. As used herein, the term "racemic mixture" (or "racemate") refers to a substantially equimolar mixture of the first and second enantiomers. As used here, the term "substantially" is intended as a teem or approximation, and not degree, so that the teem "substanitally" is intended to cover a standard deviation from the listed value that may arise, for example, from the uncertainty involved in certain measurements and calculations. In some exemplary embodiments, the first composition includes about 90 mol % to 100 mol % of the first enantiomer, and about 0 mol % to about 10 mol % of the second enantiomer. For example, the composition may include about 95 mol % to about 100 mol % of the first enantiomer, and about 0 mol % to about 5 mol % of the second enantiomer, or the composition may include about 99 mol % to about 100 mol % of the first enantiomer and about 0 mol % to about 1 mol % of the second enantiomer.

Stated somewhat differently, the first enantiomer is present in an enantiomeric excess of greater than 50%, for example about 90 to about 100% or about 95 to about 100%. As used herein, "enantiomeric excess" (or "ee") is defined as |F(+)−F(−)| (or |F(−)−F(+)| for compositions including more of the (−) enantiomer) for a mixture of (+) and (−) enantiomers, with the composition given as the mole or weight fractions F(+) and F(−), such that F(+)+F(−)=1. When given as a percentage, enantiomeric excess is defined by 100*|F(+)−F(−)| (or 100*|F(+)−F(−)|).

The first and second enantiomers are independently selected from compounds represented by Formulae 1 through 22, described in detail below. However, the first and second enantiomers are enantiomers of each other, and therefore while the arrangement of the atoms in space may differ, their chemical formulae are identical. Accordingly, if the first enantiomer is a compound represented by Formula 1, then the second enantiomer is a corresponding compound represented by Formula 2. Similarly, if the second enantiomer is a compound of Formula 1, then the first enantiomer is a corresponding compound represented by Formula 2. As another example, if the first enantiomer is a compound of Formula 13, then the second enantiomer is a corresponding compound represented by Formula 14, and so on. Based on the descriptions of the compounds of Formulae 1 through 22 below, those of ordinary skill in the art would readily recognize which Formulae represent enantiomers within the meaning herein described. As used herein, the term "corresponding compound" refers to the opposite enantiomer, such that the first and second enantiomers are enantiomers of each other, for example, (+) and (−) enantiomers having the same chemical formula but a different (i.e., opposite or mirror-image) arrangement of atoms. Indeed, as can be seen from their structures depicted below, Formula 1 and Formula 2 are (+) and (−) enantiomers of the depicted structure. Accordingly, the term "corresponding compound" denotes that the R groups and other variables are identical in the first and second enantiomers, even though one enantiomer is represented by Formula 1 and the other is represented by Formula 2.

Formula 1

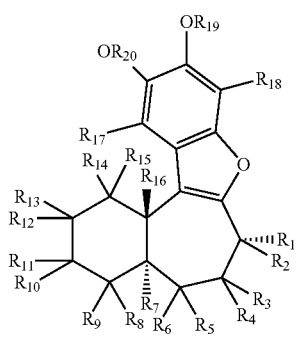

Formula 2

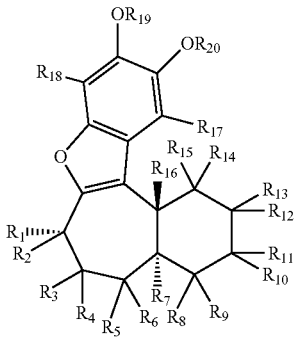

In Formulae 1 and 2, each of $R_1$ through $R_{20}$ may be independently selected from hydrogen, substituted and unsubstituted hydrocarbyl groups, substituted and unsubstituted heteroatom containing hydrocarbyl groups, and/or functional groups. Also, any two adjacent groups selected from $R_1$ through $R_{16}$ may optionally combine to form a double bond in the respective six-membered or seven-membered ring structure. As used herein, the term "hydrocarbyl groups" refers to univalent hydrocarbon radicals containing from 1 to 30 carbon atoms, for example, from 1 to 24 carbon atoms or 1 to 12 carbon atoms. The term "hydrocarbyl groups" includes linear, branched, cyclic, saturated and unsaturated species, for example, alkyl groups, alkenyl groups, alkynyl groups, aryl groups, and the like. Also, as used herein, the term "substituted," as in "substituted hydrocarbyl groups," refers to a hydrocarbyl group in which one or more hydrogen atoms (bonded to a carbon atom) is replaced with one or more non-hydrogen functional groups.

The term "functional groups" would be readily understood to those of ordinary skill in the art. However, some nonlimiting examples of suitable functional groups for use in Formulae 1 and 2 include halogens, hydroxyl groups, sulfhydryl groups, alkoxy groups (e.g., having from 1 to 24 carbon atoms), alkenyloxy groups (e.g., having from 2 to 24 carbon atoms), alkynyloxy groups (e.g., having from 2 to 24 carbon atoms), aryloxy groups (e.g., having from 5 to 24 carbon atoms), acyl groups including alkylcarbonyl groups of the formula —CO-alkyl (e.g., having from 2 to 24 carbon atoms) and arylcarbonyl groups of the formula —CO-aryl (e.g., having from 6 to 24 carbon atoms), acyloxy groups having the formula —O-acyl, alkoxycarbonyl groups having the formula —(CO)—O-alkyl (e.g., having from 2 to 24 carbon atoms), carbonyl groups (including aldehyde moieties having the formula —(CO)—H) and ketone moieties having the formula —(CO)—R where R is any hydrocarbyl group), aryloxycarbonyl groups having the formula —(CO)—O-aryl (e.g., having from 6 to 24 carbon atoms), halocarbonyl groups having the formula —CO—X (where X is a halogen), alkylcarbonato groups having the formula —O—(CO)—O-alkyl (e.g., having from 2 to 24 carbon atoms), arylcarbonato groups having the formula —O—(CO)—O-aryl (e.g., having from 6 to 24 carbon atoms), carboxy 1 groups having the formula —COOH, carboxylato groups having the formula —COO⁻, carbamoyl groups having the formula —(CO)—NH, mono-alkyl substituted carbamoyl groups having the formula —(CO)—NH-alkyl (e.g., the alkyl group having from 1 to 24 carbon atoms), di-alkyl substituted carbamoyl groups having the formula —(CO)—N-alkyl₂ (e.g., each alkyl group having from 1 to 24 carbon atoms), mono-aryl substituted carbamoyl groups having the formula —(CO)—NH-aryl (e.g., the aryl group having from 6 to 24 carbon atoms), di-aryl substituted carbamoyl groups having the formula —(CO)—N-aryl₂ (e.g., each aryl group having from 6 to 24 carbon atoms), di-N(alkyl)-N(aryl) substituted carbamoyl groups having the formula —(CO)—N-(alkyl)(aryl), thiocarbamoyl groups having the formula —(CS)—NH$_2$, carbamido groups having the formula —NH—(CO)—NH$_2$, cyano groups, isocyano groups, cyanato groups, isocyanato groups, isothiocyanato groups, azido groups, formyl groups, thioformyl groups, amino groups, mono-alkyl substituted amino groups (e.g., the alkyl group having from 1 to 24 carbon atoms), di-alkyl substituted amino groups (e.g., the alkyl group having from 1 to 24 carbon atoms), mono-aryl substituted amino groups (e.g., the aryl group having from 6 to 24 carbon atoms), di-aryl substituted amino groups (e.g., each aryl group having from 6 to 24 carbon atoms), alkylamido groups having the formula —NH—(CO)-alkyl (e.g., having from 2 to 24 carbon atoms), arylamido groups having the formula —NH—(CO)-aryl (e.g., having from 6 to 24 carbon atoms), imino groups having the formula —CR=NH (where R is hydrogen, alkyl, aryl, alkaryl, aralkyl, etc.), alkyl imino groups having the formula —CR=N-alkyl (where R is hydrogen, alkyl, aryl, aralkyl, alkaryl, etc.), aryl imino groups having the formula —CR=N-aryl (where R is hydrogen, alkyl, aryl, aralkyl, alkaryl, etc.), nitro groups, nitroso groups having the formula —NO, sulfo groups having the formula —SO$_2$—OH, sulfonato groups having the formula —SO$_2$—O$^-$, alkylsulfanyl groups having the formula —S-alkyl (also called, interchangeably, alkylthio groups), arylsulfanyl groups having the formula —S-aryl (also called, interchangeably arylthio groups), alkylsulfanyl groups having the formula —(SO)-alkyl, arylsulfinyl groups having the formula —(SO)-aryl, alkylsulfonyl groups having the formula —SO$_2$-alkyl, arylsulfonyl groups having the formula —SO$_2$-aryl, boryl groups having the formula —BH$_2$, borono groups having the formula —B(OH)$_2$, boronato groups having the formula —B(OR)$_2$ (where R is alkyl or another hydrocarbyl group), phosphono groups having the formula —P(O)(OH)$_2$, phosphonato groups having the formula —P(O)(O$^-$)$_2$, phosphinato groups having the formula —P(O)(O$^-$), phospho groups having the formula —PO$_2$, and phosphino groups having the formula —PH$_2$.

In addition to, or instead of, being substituted with a functional group, the substituted species may be substituted with hydrocarbyl groups, for example, alkyl groups (e.g., having from 1 to 24 carbon atoms, or from 1 to 12 carbon atoms, or from 1 to 6 carbon atoms), alkenyl groups (e.g., having from 2 to 24 carbon atoms, or from 2 to 13 carbon atoms, or from 2 to 6 carbon atoms), alkynyl groups (e.g., having from 2 to 24 carbon atoms, or from 2 to 12 carbon atoms, or from 2 to 6 carbon atoms), aryl groups (e.g., having from 5 to 24 carbon atoms, or from 5 to 14 carbon atoms), alkaryl groups (i.e., aryl with an alkyl substituent, e.g., having from 6 to 24 carbon atoms, or from 6 to 16 carbon atoms), and/or aralkyl groups (i.e., alkyl with an aryl substituent, e.g., having from 6 to 24 carbon atoms, or from 6 to 16 carbon atoms). Also, any of the functional groups or hydrocarbyl group substituents may be further substituted (if the group permits) with one or more additional functional groups or hydrocarbyl groups.

In some embodiments, for example, each of R$_1$ through R$_{20}$ is independently selected from hydrogen, carbonyl groups and alkyl groups. In some exemplary embodiments, each of R$_1$ through R$_{20}$ is selected from hydrogen, aldehyde carbonyl groups and methyl groups. For example, in some embodiments, each of R$_2$ through R$_7$, R$_{10}$ through R$_{15}$, R$_{17}$, R$_{19}$ and R$_{20}$ is hydrogen, each of R$_1$, R$_8$, R$_9$ and R$_{16}$ is an alkyl group, and R$_{18}$ is a carbonyl group. For example, in some embodiments, each of R$_2$ through R$_7$, R$_{10}$ through R$_{15}$ and R$_{17}$ is hydrogen, each of R$_1$, R$_8$, R$_9$, and R$_{16}$ is a methyl group, and each of R$_{18}$ and R$_{18}$' is an aldehyde carbonyl group. This configuration yields (+)-liphagal (Formula 1A below) and (−)-liphagal (Formula 2A below). However, it is understood that although this configuration is depicted as having each of R$_2$ through R$_7$, R$_{10}$ through R$_{15}$, R$_{17}$, R$_{19}$ and R$_{20}$ as hydrogen, any or all of these hydrogen atoms could be substituted with the substituents described above, yielding derivatives of (+)-liphagal or (−)-liphagal.

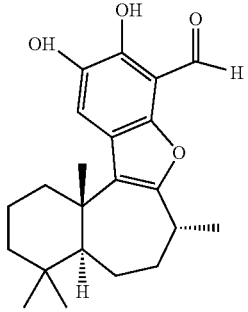

Formula 1A

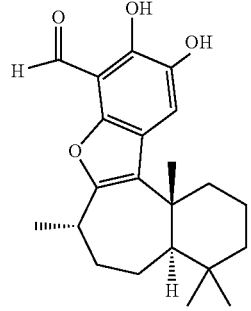

Formula 2A

In other embodiments, each of R$_2$ through R$_7$, R$_{10}$ through R$_{15}$ and R$_{17}$ is hydrogen, R$_{18}$ is an aldehyde carbonyl group, and each of R$_1$, R$_8$, R$_9$, R$_{16}$, R$_{19}$ and R$_{20}$ is an alkyl group (e.g., a methyl group). This configuration yields a (+)-enantiomer of Formula 1B below and a (−)-enantiomer of Formula 2B below. These enantiomers are precursors to (+)-liphagal and (−)-liphagal, respectively, and are compounds useful in the synthesis of (+)-liphagal and (−)-liphagal. It is understood that although this configuration is depicted as having each of R$_2$ through R$_7$, R$_{10}$ through R$_{15}$ and R$_{17}$ as hydrogen, any or all of these hydrogen atoms could be substituted with the substituents described above, yielding derivatives of the (+)-enantiomer or the (−)-enantiomer of Formulae 1B and 2B.

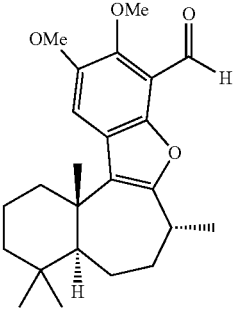

Formula 1B

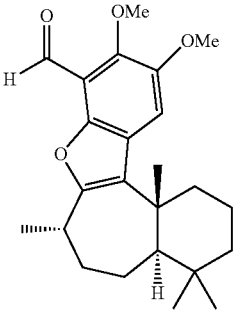

Formula 2B

According to some exemplary embodiments of the present invention, (+) and (−) precursors to the enantiomers of Formula 1B and Formula 2B also have the general formula of Formula 1 and Formula 2. However, in these precursors, each of $R_2$ through $R_7$, $R_{10}$ through $R_{15}$, $R_{17}$ and $R_{18}$ is hydrogen, and each of $R_1$, $R_8$, $R_9$, $R_{16}$, $R_{19}$ and $R_{20}$ is an alkyl group (e.g., a methyl group). This configuration yields a (+)-enantiomer of Formula 1C below and a (−)-enantiomer of Formula 2C below. It is understood that although this configuration is depicted as having each of $R_2$ through $R_7$, $R_{10}$ through $R_{15}$, $R_{17}$ and $R_{18}$ as hydrogen, any or all of these hydrogen atoms could be substituted with the substituents described above, yielding derivatives of the (+)-enantiomer or the (−)-enantiomer of Formulae 1C and 2C.

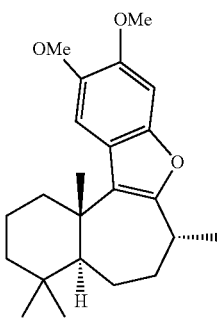

Formula 1C

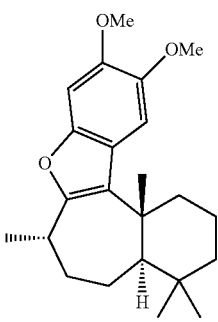

Formula 2C

In some embodiments, (+) and (−) precursors to the enantiomers and derivatives of Formulae 1C and 2C have the following Formulae 3 and 4.

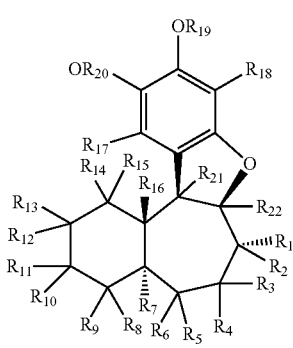

Formula 3

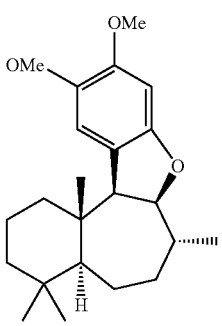

Formula 4

In Formulae 3 and 4, each of $R_1$ through $R_{20}$ is as described above with respect to Formulae 1 and 2 (i.e., like reference numerals designate like moieties and/or functional groups throughout). Also, any two adjacent groups selected from $R_1$ through $R_{16}$ may optionally combine to form a double bond in the respective six-membered or seven-membered ring structure. Additionally, $R_{21}$ and $R_{22}$ may each be independently selected from the substituents discussed above for $R_1$ through $R_{20}$ in Formulae 1 and 2. In some embodiments, however, $R_{21}$ and $R_{22}$ may be hydrogen. For example, in some embodiments of the present invention, in Formulae 3 and 4, each of $R_1$ through $R_{20}$ is independently selected from hydrogen, carbonyl groups and alkyl groups. In some exemplary embodiments, each of $R_1$ through $R_{20}$ is selected from hydrogen, aldehyde carbonyl groups and methyl groups. For example, in some embodiments, each of $R_2$ through $R_7$, $R_{10}$ through $R_{15}$, $R_{17}$, $R_{21}$ and $R_{22}$ is hydrogen, and each of $R_1$, $R_{16}$, $R_{19}$ and $R_{20}$ is an alkyl group. In some embodiments, for example, each of $R_2$ through $R_{15}$, $R_{17}$, $R_{18}$, $R_{21}$ and $R_{22}$ is hydrogen, and each of $R_1$, $R_8$, $R_9$, $R_{16}$, $R_{19}$ and $R_{20}$ is a methyl group. This configuration yields the (+)-enantiomer of Formula 3A below and the (−)-enantiomer of Formula 4A below. However, it is understood that although this configuration is depicted as having each of each of $R_2$ through $R_7$, $R_{10}$ through $R_{15}$, $R_{17}$, $R_{18}$, $R_{21}$ and $R_{22}$ as hydrogen, any or all of these hydrogen atoms could be substituted with the substituents described above, yielding additional derivatives of the (+)-enantiomer and the (−)-enantiomer of Formulae 3 and 4.

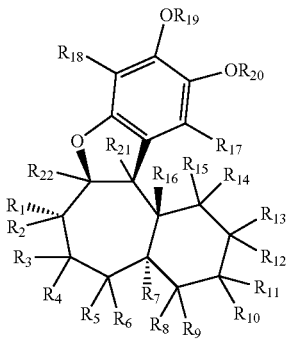

Formula 3a

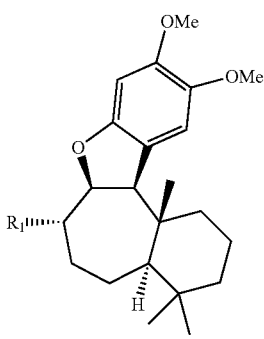

Formula 4a

According to other embodiments of the present invention, (+) and (−) precursors (Formulae 5 and 6 below) to the enantiomers of Formula 3 and 4 have the structures of Formulae 3 and 4 in which the $R_7$ and $R_6$ functional groups (or hydrogen atoms) combine to form carbon to carbon double bonds in the seven-membered rings. All of the R groups in the following Formulae 5 and 6 (except for $R_7$ and $R_6$ which are absent from Formulae 5 and 6) are as described above with respect to Formulae 3 and 4.

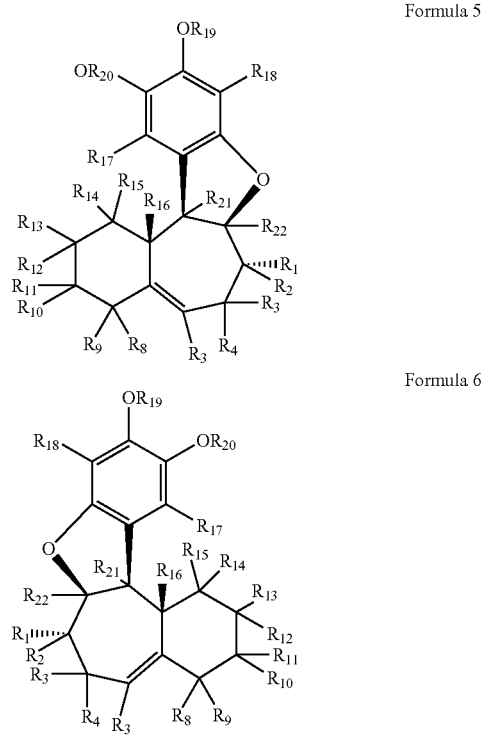

Formula 5

Formula 6

As in Formulae 3 and 4, each of $R_1$ through $R_5$ and $R_8$ through $R_{22}$ in Formulae 5 and 6 are as described above with respect to $R_1$ through $R_{20}$ in Formulae 1-4 (i.e., like reference numerals designate like moieties and/or functional groups throughout). Additionally, any two adjacent groups selected from $R_1$ through $R_5$, $R_8$ through $R_{16}$, $R_{21}$ and $R_{22}$ may optionally combine to form a carbon to carbon double bond in the respective six-membered ring or seven-membered ring. Also, $R_{21}$ and $R_{22}$ may each be independently selected from the substituents discussed above for $R_1$ through $R_{20}$. In some embodiments, however, $R_{21}$ and $R_{22}$ may be hydrogen. For example, in some embodiments of the present invention, in Formulae 5 and 6, each of $R_1$ through $R_5$, and $R_8$ through $R_{22}$ is independently selected from hydrogen, carbonyl groups and alkyl groups. In some exemplary embodiments, each of $R_1$ through $R_5$, and $R_8$ through $R_{22}$ is selected from hydrogen, aldehyde carbonyl groups and methyl groups. For example, in some embodiments, each of $R_2$ through $R_5$, $R_{10}$ through $R_{15}$, $R_{17}$, $R_{21}$, and $R_{22}$ is hydrogen, and each of $R_1$, $R_8$, $R_9$, $R_{16}$, $R_{19}$, and $R_{20}$ is an alkyl group. In some embodiments, for example, each of $R_2$ through $R_5$, $R_{10}$ through $R_{15}$, $R_{17}$, $R_{18}$, $R_{21}$, and $R_{22}$ is hydrogen, and each of $R_1$, $R_8$, $R_9$, $R_{16}$, $R_{19}$, and $R_{20}$ is a methyl group. This configuration yields the (+)-enantiomer of Formula 5A below and the (−)-enantiomer of Formula 6A below. However, it is understood that although this configuration is depicted as having each of each of $R_2$ through $R_5$ and $R_{10}$ through $R_{15}$, $R_{17}$, $R_{18}$, $R_{21}$, and $R_{22}$ as hydrogen, any or all of these hydrogen atoms could be substituted with the substituents described above, yielding additional derivatives of the (+)-enantiomer and the (−)-enantiomer of Formulae 5 and 6.

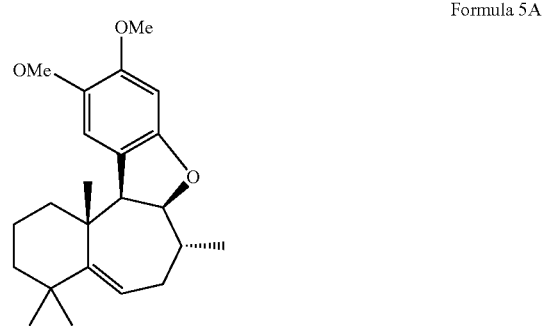

Formula 5A

Formula 6A

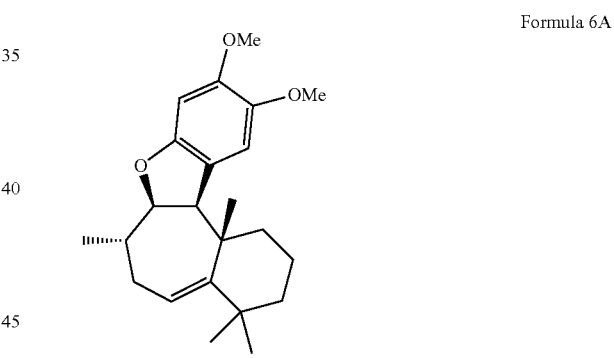

According to another embodiment of the present invention, (+) and (−) precursors to the enantiomers of Formulae 5, 6, 5A and 6A are represented by Formulae 7 and 8 below.

Formula 7

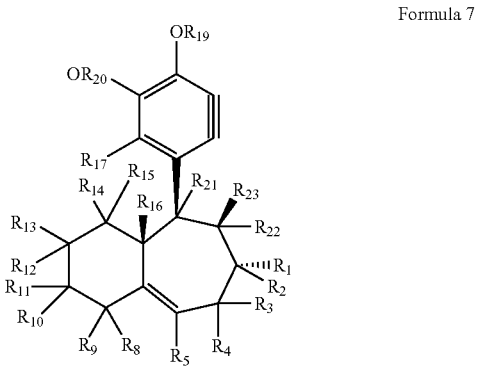

-continued

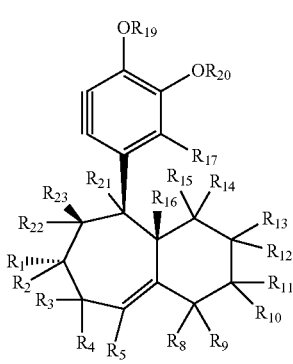

Formula 8

As can be seen from Formulae 7 and 8, these structures are related to their reaction products (i.e., Formulae 5 and 6) in the preservation of the 6-7 ring structure, but differ from their reaction products in the absence of the heteroaromatic ring attached to the seven membered ring, the presence of an alkyne in the six membered aromatic ring, the absence of $R_{18}$ (in Formula 7) and $R_{18}'$ (in Formula 8), and the inclusion of $R_{23}$ (in Formula 7) and $R_{23}'$ (in Formula 8). However, in Formulae 7 and 8, all of the like numbered R groups (except for $R_6$, $R_7$, and $R_{18}$ which are absent from Formulae 7 and 8) are as described above with respect to Formulae 1, 2, 3, 4, 5 and 6.

In Formula 7 and 8, each of $R_1$ through $R_5$ and $R_8$ through $R_{17}$ and $R_{19}$ through $R_{22}$ are as described above with respect to $R_1$ through $R_{20}$ (i.e., like reference numerals designate like moieties and/or functional groups throughout). Additionally, any two adjacent groups selected from $R_1$ through $R_5$, $R_8$ through $R_{16}$, $R_{21}$, and $R_{22}$ may optionally combine to form a carbon to carbon double bond in the respective six-membered ring or seven-membered ring. Also, $R_{21}$, and $R_{22}$ may each be independently selected from the substituents discussed above for $R_1$ through $R_{20}$. In some embodiments, however, $R_{21}$ and $R_{22}$ may be hydrogen.

Further, $R_{23}$ is an oxygen containing functional group. For example, $R_{23}$ may be a functional group represented by —OM, where M is an alkali metal. In some embodiments, for example, M may be lithium, sodium or potassium. For example, in some embodiments, M is lithium.

In some exemplary embodiments of the present invention, in Formulae 7 and 8, each of $R_1$ through $R_5$, $R_8$ through $R_{17}$ and $R_{19}$ through $R_{22}$ is independently selected from hydrogen, carbonyl groups and alkyl groups, and $R_{23}$ is a functional group represented by —OM as defined above. In some exemplary embodiments, each of $R_1$ through $R_5$, $R_8$ through $R_{17}$ and $R_{19}$ through $R_{22}$ is selected from hydrogen, aldehyde carbonyl groups and methyl groups, and $R_{23}$ is a functional group represented by —OM as defined above. For example, in some embodiments, each of $R_2$ through $R_5$, $R_{10}$ through $R_{15}$, $R_{17}$, $R_{21}$, and $R_{22}$ is hydrogen, each of $R_1$, $R_8$, $R_9$, $R_{16}$, $R_{19}$, and $R_{20}$ is an alkyl group, and $R_{23}$ is a functional group represented by —OM as defined above. In some embodiments, for example, each of $R_2$ through $R_5$, $R_{10}$ through $R_{15}$, $R_{17}$, $R_{21}$, and $R_{22}$ is hydrogen, each of $R_1$, $R_8$, $R_9$, $R_{16}$, $R_{19}$, and $R_{20}$ is a methyl group, and $R_{23}$ is a functional group represented by —OLi. This configuration yields the (+)-enantiomer of Formula 7A below and the (−)-enantiomer of Formula 8A below. However, it is understood that although this configuration is depicted as having each of each of each of $R_2$ through $R_5$ and $R_8$ through $R_{15}$, $R_{17}$, $R_{21}$, and $R_{22}$ as hydrogen, any or all of these hydrogen atoms could be substituted with the substituents described above, yielding additional derivatives of the (+)-enantiomer and the (−)-enantiomer of Formulae 7 and 8.

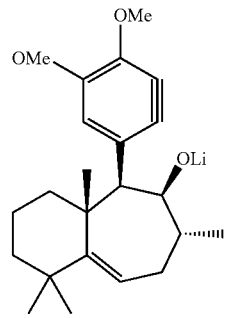

Formula 7A

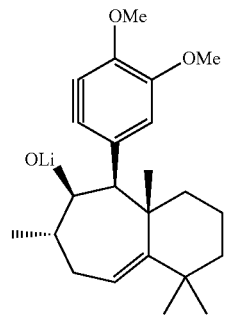

Formula 8A

According to another embodiment of the present invention, (+) and (−) precursors to the enantiomers of Formulae 7, 8, 7A and 8A are represented by Formulae 9 and 10 below.

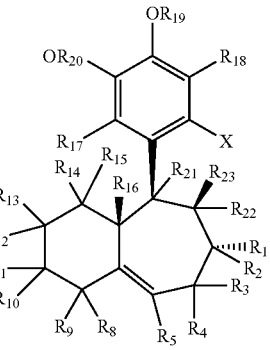

Formula 9

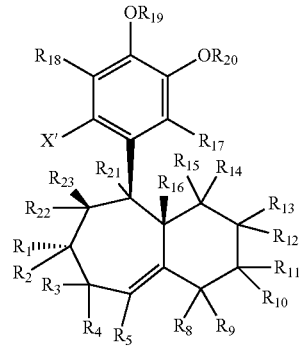

Formula 10

As can be seen from Formulae 9 and 10, these structures are related to the structures of their reaction products (i.e., Formulae 7 and 8) in the preservation of the 6-7 ring system, but differ from their reaction products in the presence of $R_{18}$, the inclusion of an X group, and the absence of the alkynyl linkage in the six membered aromatic ring. However, in Formulae 9 and 10, all of the like numbered R groups are as described above with respect to Formulae 7 and 8.

In Formula 9 and 10, each of $R_1$ through $R_5$ and $R_8$ through $R_{22}$ are as described above with respect to $R_1$ through $R_{22}$ (i.e., like reference numerals designate like moieties and/or functional groups throughout). Additionally, any two adjacent groups selected from $R_1$ through $R_5$, $R_8$ through $R_{16}$, $R_{21}$, and $R_{22}$ may optionally combine to form a carbon to carbon double bond in the respective six-membered ring or seven-membered ring. Also, $R_{21}$ and $R_{22}$ may each be independently selected from the substituents discussed above for $R_1$ through $R_{22}$. In some embodiments, however, $R_{21}$ and $R_{22}$ may be hydrogen.

Further, $R_{23}$ is an oxygen containing functional group. For example, $R_{23}$ may be a hydroxyl group. Also, X is a halogen, for example, Br, I, Cl or F. In some embodiments, for example, X is Br.

In some exemplary embodiments of the present invention, in Formulae 9 and 10, each of $R_1$ through $R_5$, and $R_8$ through $R_{22}$ is independently selected from hydrogen, carbonyl groups and alkyl groups, $R_{23}$ is an oxygen containing functional group, and X is a halogen. In some exemplary embodiments, each of $R_1$ through $R_5$, and $R_8$ through $R_{22}$ is selected from hydrogen, aldehyde carbonyl groups and methyl groups, $R_{23}$ is an oxygen containing functional group, and X is a halogen. For example, in some embodiments, each of $R_2$ through $R_5$, $R_{10}$ through $R_{15}$, $R_{17}$, $R_{18}$, $R_{21}$, and $R_{22}$ is hydrogen, each of $R_1$, $R_8$, $R_9$, $R_{16}$, $R_{19}$, and $R_{20}$ is an alkyl group, $R_{23}$ is an oxygen containing functional group, and X is a halogen. In some embodiments, for example, each of $R_2$ through $R_5$, $R_{10}$ through $R_{15}$, $R_{17}$, $R_{18}$, $R_{21}$, and $R_{22}$ is hydrogen, each of $R_1$, $R_8$, $R_9$, $R_{16}$, $R_{19}$, and $R_{20}$ is a methyl group, $R_{23}$ is a hydroxyl group, and X is a halogen (e.g., Br). This configuration yields the (+)-enantiomer of Formula 9A below and the (−)-enantiomer of Formula 10A below. However, it is understood that although this configuration is depicted as having each of $R_2$ through $R_5$ and $R_{10}$ through $R_{15}$, $R_{17}$, $R_{18}$, $R_{21}$, and $R_{22}$ as hydrogen, any or all of these hydrogen atoms could be substituted with the substituents described above, yielding additional derivatives of the (+)-enantiomer and the (−)-enantiomer of Formulae 9 and 10.

Formula 9A

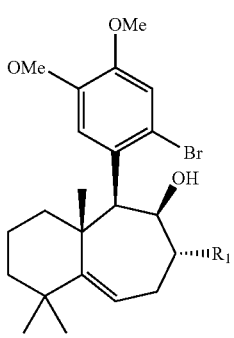

Formula 10A

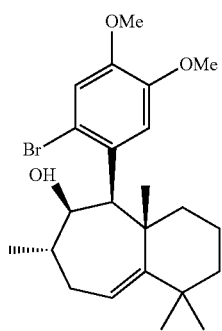

According to another embodiment of the present invention, (+) and (−) precursors to the enantiomers of Formulae 9, 10, 9A and 10A are represented by Formulae 11 and 12 below.

Formula 11

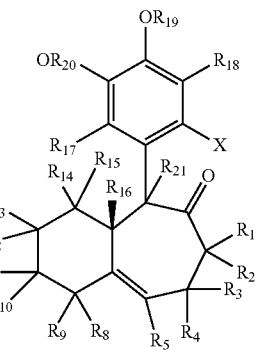

Formula 12

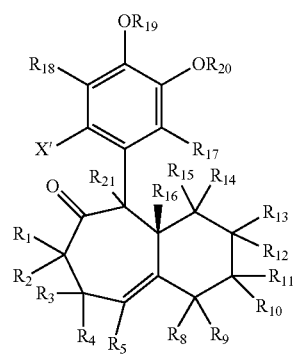

As can be seen from Formulae 11 and 12, these structures are related to the structures of their reaction products (i.e., Formulae 9 and 10) in the preservation of the 6-7 ring system, but differ from their reaction products in the presence of a carbonyl group on each of the seven-membered rings at the $R_{23}$ positions, and the absence of the $R_{22}$ and $R_{23}$ groups. However, in Formulae 11 and 12, all of the like numbered R groups are as described above with respect to Formulae 9 and 10.

In Formula 11 and 12, each of $R_1$ through $R_5$ and $R_8$ through $R_{21}$ are as described above with respect to $R_1$ through $R_{22}$ (i.e., like reference numerals designate like moieties and/or functional groups throughout). Additionally, any two adjacent groups selected from $R_1$ through $R_5$, $R_8$ through $R_{16}$, and $R_{21}$ may optionally combine to form a carbon to carbon double bond in the respective six-membered ring or seven-membered ring. Also, $R_{21}$ may each be independently selected from the substituents discussed above for $R_1$ through $R_{22}$. In some embodiments, however, $R_{21}$ may be hydrogen.

Also, X is a halogen, for example, Br, I, Cl or F. In some embodiments, for example, X is Br.

Additionally, although not depicted in Formulae 11 and 12, the bonds connecting the seven membered rings to the six membered aromatic rings can have any suitable stereochemistry. For example, the stereochemistry of that bond may be either that depicted in the following Formulae 11A and 12A or that depicted in the following Formulae 11B and 12B.

Formula 11A

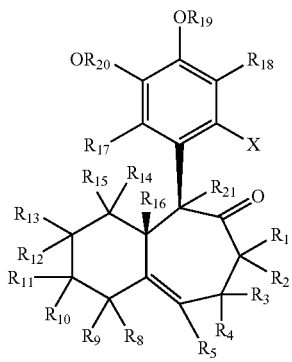

Formula 12A

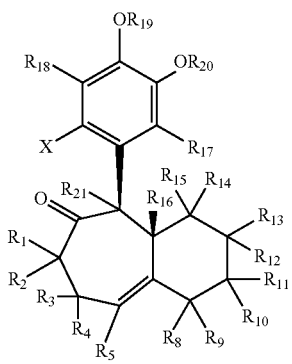

Formula 11B

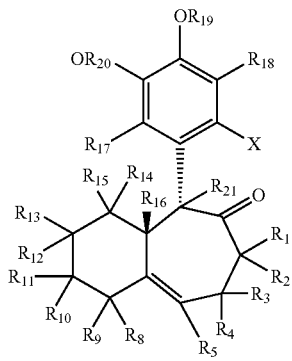

Formula 12B

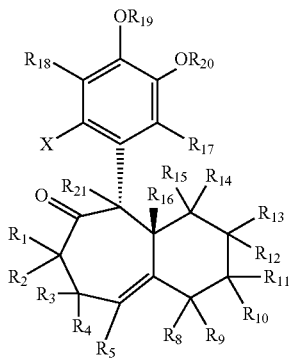

Similarly, although not depicted in Formulae 11 and 12, the bond connecting the $R_1$ and $R_1'$ groups to the seven membered rings can have any suitable stereochemistry. In some embodiments, for example, the stereochemistry of that bond is that depicted in the following Formulae 11C and 12C.

Formulae 11C

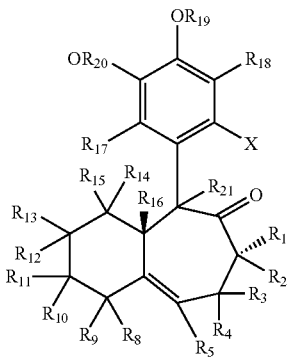

Formulae 12C

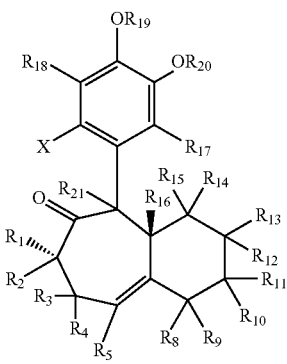

In some exemplary embodiments of the present invention, in Formulae 11 and 12, each of $R_1$ through $R_5$, and $R_8$ through $R_{21}$ is independently selected from hydrogen, carbonyl groups and alkyl groups, and X is a halogen. In some exemplary embodiments, each of $R_1$ through $R_5$, and $R_8$ through $R_{21}$ is selected from hydrogen, aldehyde carbonyl groups and methyl groups, and X is a halogen. For example, in some embodiments, each of $R_2$ through $R_5$, $R_{10}$ through $R_{15}$, $R_{17}$, $R_{18}$, and $R_{21}$ is hydrogen, each of $R_1$, $R_8$, $R_9$, $R_{16}$, $R_{19}$, and $R_{20}$ is an alkyl group, and X is a halogen. In some embodiments, for example, each of $R_2$ through $R_5$, $R_{10}$ through $R_{15}$, $R_{17}$, $R_{18}$, and $R_{21}$ is hydrogen, each of $R_1$, $R_8$, $R_9$, $R_{16}$, $R_{19}$, and $R_{20}$ is a methyl group, and X is a halogen (e.g., Br). This configuration yields the (+)-enantiomer of Formula 11D below and the (−)-enantiomer of Formula 12D below. However, although the stereochemistry of the bonds connecting the seven membered rings to the six membered aromatic rings, and the bonds connecting the $R_1$ groups to the seven membered rings are not shown in the below Formulae 11D and 12D, it is understood that these bonds can have any suitable stereochemistry, as discussed above. It is understood that although this configuration is depicted as having each of $R_2$ through $R_5$ and $R_{10}$ through $R_{15}$, $R_{17}$, $R_{18}$, and $R_{21}$ as hydrogen, any or all of these hydrogen atoms could be substituted with the substituents described above, yielding additional derivatives of the (+)-enantiomer and the (−)-enantiomer of Formulae 9 and 10.

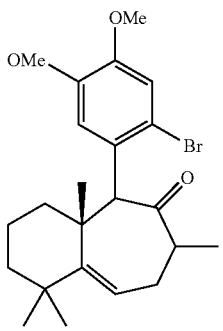

Formula 11D

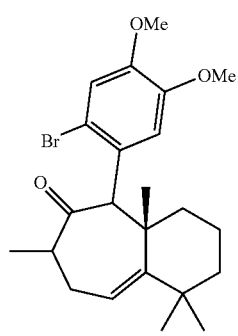

Formula 12D

According to other embodiments of the present invention, (+) and (−) precursors (Formulae 13 and 14 below) to the enantiomers of Formula 11 and 12 have the structures of Formulae 11 and 12 in which the $R_2$ and $R_3$ functional groups (or hydrogen atoms) combine to form carbon to carbon double bonds in the seven-membered rings. In Formulae 13 and 14, all of the like numbered R groups are as described above with respect to Formulae 11 and 12.

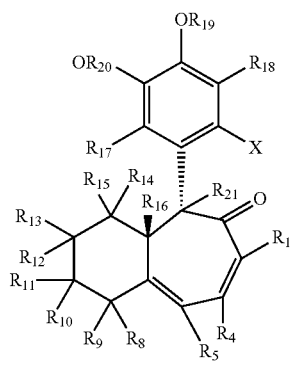

Formula 13

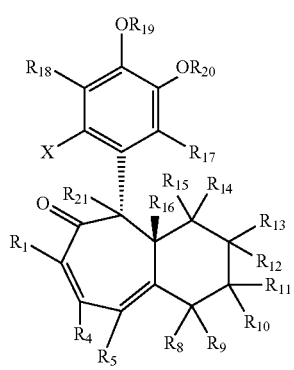

Formula 14

In Formula 13 and 14, each of $R_1$, $R_4$, $R_5$ and $R_8$ through $R_{21}$ are as described above with respect to $R_1$ through $R_{22}$ (i.e., like reference numerals designate like moieties and/or functional groups throughout). Additionally, any two adjacent groups selected from $R_8$ through $R_{16}$, and $R_{21}$ may optionally combine to form a carbon to carbon double bond in the respective six-membered rings or seven-membered rings. Also, $R_{21}$ may be selected from the substituents discussed above for $R_1$ through $R_{22}$. In some embodiments, however, $R_{21}$ may be hydrogen.

Also, X is a halogen, for example, Br, I, Cl or F. In some embodiments, for example, X is Br.

In some exemplary embodiments of the present invention, in Formulae 13 and 14, each of $R_1$, $R_4$, $R_5$, and $R_8$ through $R_{21}$ is independently selected from hydrogen, carbonyl groups and alkyl groups, and X is a halogen. In some exemplary embodiments, each of $R_1$, $R_4$, $R_5$, and $R_8$ through $R_{21}$, is selected from hydrogen, aldehyde carbonyl groups and methyl groups, and X is a halogen. For example, in some embodiments, each of $R_1$, $R_4$, $R_5$, $R_{10}$ through $R_{15}$, $R_{17}$, $R_{18}$, and $R_{21}$ is hydrogen, each of $R_8$, $R_9$, $R_{16}$, $R_{19}$, and $R_{20}$ is an alkyl group, and X is a halogen. In some embodiments, for example, each of $R_1$, $R_4$, $R_5$, $R_{10}$ through $R_{15}$, $R_{17}$, $R_{18}$, and $R_{21}$ is hydrogen, each of $R_8$, $R_9$, $R_{16}$, $R_{19}$, and $R_{20}$ is a methyl group, and X is a halogen (e.g., Br). This configuration yields the (+)-enantiomer of Formula 13A below and the (−)-enantiomer of Formula 14A below. It is understood that although this configuration is depicted as having each of $R_1$, $R_4$, $R_5$, $R_{10}$ through $R_{15}$, $R_{17}$, $R_{18}$, and $R_{21}$ as hydrogen, any or all of these hydrogen atoms could be substituted with the substituents described above, yielding additional derivatives of the (+)-enantiomer and the (−)-enantiomer of Formulae 11 and 12.

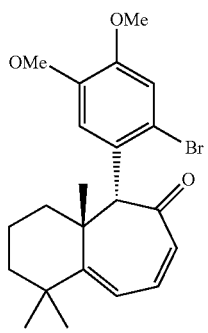

Formula 13A

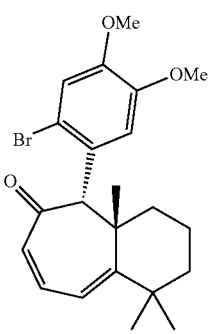

Formula 14A

According to other embodiments of the present invention, (+) and (−) precursors to the enantiomers of Formulae 13 and 14 are represented by Formulae 15 and 16 below. As can be seen from Formulae 15 and 16 below, these structures are precursors to the 6-7 ring system depicted in the previously described Formulae. In Formulae 15 and 16, all of the like numbered R groups are as described above with respect to Formulae 13 and 14.

Formula 15

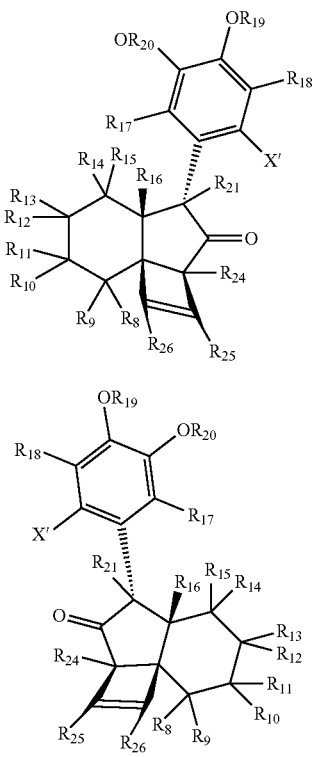

Formula 16

Formula 15A

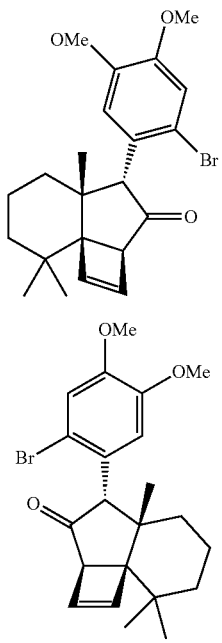

Formula 16A

In Formula 15 and 16, each of $R_8$ through $R_{21}$ are as described above with respect to $R_1$ through $R_{22}$ (i.e., like reference numerals designate like moieties and/or functional groups throughout). Additionally, any two adjacent groups selected from $R_8$ through $R_{16}$, and $R_{21}$ may optionally combine to form a carbon to carbon double bond in the respective six-membered rings or five-membered rings. Also, $R_{24}$, $R_{25}$, and $R_{26}$ may be selected from the substituents discussed above for $R_1$ through $R_{22}$. In some embodiments, however, $R_{24}$, $R_{25}$, and $R_{26}$ may be hydrogen.

Also, X' is either hydrogen or a halogen, for example, Br, I, Cl or F. In some embodiments, for example, X' is Br. In other embodiments, however, X' is hydrogen.

In some exemplary embodiments of the present invention, in Formulae 15 and 16, each of $R_8$ through $R_{21}$ and $R_{24}$ through $R_{26}$ is independently selected from hydrogen, carbonyl groups and alkyl groups, and X' is hydrogen or a halogen. In some exemplary embodiments, each of $R_8$ through $R_{21}$ and $R_4$ through $R_{26}$ is selected from hydrogen, aldehyde carbonyl groups and methyl groups, and X' is hydrogen or a halogen. For example, in some embodiments, each of $R_{10}$ through $R_{15}$, $R_{17}$, $R_{18}$, $R_{21}$, and $R_{24}$ through $R_{26}$ is hydrogen, each of $R_8$, $R_9$, $R_{16}$, $R_{19}$, and $R_{20}$ is an alkyl group, and X' is hydrogen or a halogen. In some embodiments, for example, each of $R_{10}$ through $R_{15}$, $R_{17}$, $R_{18}$, $R_{21}$, and $R_{24}$ through $R_{26}$ is hydrogen, each of $R_8$, $R_9$, $R_{16}$, $R_{19}$, and $R_{20}$ is a methyl group, and X' is a halogen (e.g., Br). This configuration yields the (+)-enantiomer of Formula 15A below and the (−)-enantiomer of Formula 16A below. It is understood that although this configuration is depicted as having each of $R_{10}$ through $R_{15}$, $R_{17}$, $R_{18}$, $R_{21}$, and $R_{24}$ through $R_{26}$ as hydrogen, any or all of these hydrogen atoms could be substituted with the substituents described above, yielding additional precursors to the (+)-enantiomer and the (−)-enantiomer of Formulae 13 and 14.

In other embodiments, for example, each of $R_{10}$ through $R_{15}$, $R_{17}$, $R_{18}$, $R_{21}$, and $R_{24}$ through $R_{26}$ is hydrogen, each of $R_8$, $R_9$, $R_{16}$, $R_{19}$, and $R_{20}$ is a methyl group, and X' is a hydrogen. This configuration yields the (+)-enantiomer of Formula 15B below and the (−)-enantiomer of Formula 16B below. Again, it is understood that although this configuration is depicted as having each of X', $R_{10}$ through $R_{15}$, $R_{17}$, $R_{18}$, $R_{21}$, and $R_{24}$ through $R_{26}$ as hydrogen, any or all of these hydrogen atoms could be substituted with the substituents described above, yielding additional precursors to the (+)-enantiomer and the (−)-enantiomer of Formulae 13 and 14.

Formula 15B

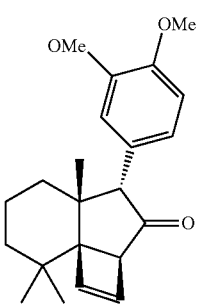

Formula 16B

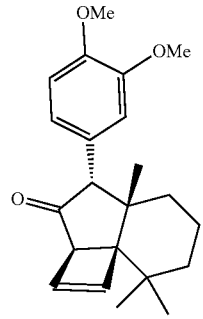

According to other embodiments of the present invention, (+) and (−) precursors to the enantiomers of Formulae 15 and 16 are represented by Formulae 17 and 18 below. As can be seen from Formulae 17 and 18 below, these structures are precursors to the three ring systems depicted in the previously described Formulae. In Formulae 17 and 18, all of the like numbered R groups are as described above with respect to Formulae 15 and 16.

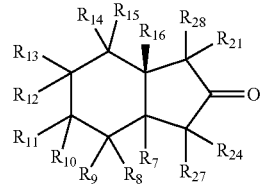

Formula 17

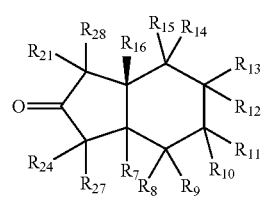

Formula 18

In Formula 17 and 18, each of $R_7$ through $R_{17}$, $R_{21}$ and $R_{24}$ are as described above with respect to $R_1$ through $R_{22}$ in Formulae 1-16 (i.e., like reference numerals designate like moieties and/or functional groups throughout). Additionally, any two adjacent groups selected from $R_7$ through $R_{16}$, $R_{21}$, $R_{22}$, $R_{24}$, $R_{27}$ and $R_{28}$ may optionally combine to form a carbon to carbon double bond in the respective six-membered rings or five-membered rings, and/or may optionally combine to form a cyclic or aromatic ring. In particular, in some embodiments, $R_7$ and $R_{27}$ may optionally combine to form a cyclobutane ring which may be saturated or unsaturated (e.g., monounsaturated as shown in Formulae 17A and 18A below). Also, $R_{24}$, $R_{27}$, and $R_{28}$ may be selected from the substituents discussed above for $R_1$ through $R_{22}$. In some embodiments, however, $R_{24}$, and $R_{28}$ may be hydrogen, and $R_{27}$ may combine with $R_7$ to form either a carbon to carbon double bond in the five membered ring (e.g., as shown in Formulae 17B and 18B below) or a cyclic or aromatic ring (e.g., a monounsaturated cyclobutane moiety as shown in Formulae 17A and 18A below).

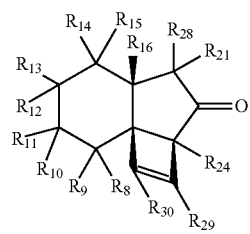

Formula 17A

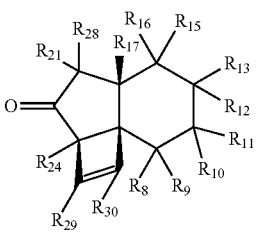

Formula 18A

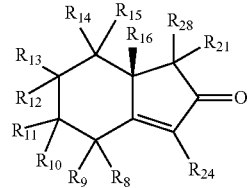

Formula 17B

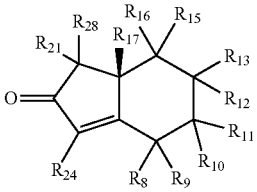

Formula 18B

In Formulae 17A and 18A, each of $R_{29}$ and $R_{30}$ may be selected from the substituents discussed above for $R_1$ through $R_{22}$ as well as trialkylsilyl groups. However, in some embodiments, each of $R_{29}$ and $R_{30}$ may be selected from hydrogen and trialkylsilyl groups. For example, each of $R_{29}$ and $R_{30}$ may be selected from hydrogen and trimethylsilyls groups.

In some exemplary embodiments of the present invention, in Formulae 17, 18, 17A, 17B, 18, 18A and 18B, each of $R_7$ through $R_{16}$, $R_{21}$, $R_{24}$, $R_{27}$ and $R_{28}$ is independently selected from hydrogen, carbonyl groups and alkyl groups, and each of $R_{29}$ and $R_{30}$ (when present) may be selected from hydrogen and trialkylsilyl groups. In some embodiments, however, $R_{24}$ and $R_{28}$ may be hydrogen, $R_{27}$ may combine with $R_7$ to form either a carbon to carbon double bond in the five membered ring (e.g., as shown in Formulae 17B and 18B above) or a cyclic or aromatic ring (e.g., a monounsaturated cyclobutane moiety as shown in Formulae 17A and 18A above), and each of $R_{29}$ and $R_{30}$ (when present) may be selected from hydrogen and trialkylsilyl groups. Also, in some exemplary embodiments, each of $R_7$ through $R_{16}$, $R_{21}$, $R_{24}$, $R_{27}$, and $R_{28}$ may be selected from hydrogen, aldehyde carbonyl groups and methyl groups, $R_{27}$ may combine with $R_7$ to form either a carbon to carbon double bond in the five membered ring or a cyclic or aromatic ring, and each of $R_{29}$ and $R_{30}$ (when present) may be selected from hydrogen and trialkylsilyl groups. For example, in some embodiments, each of $R_{10}$ through $R_{15}$, $R_{21}$, $R_{28}$, and $R_{24}$ is hydrogen, each of $R_8$, $R_9$ and $R_{16}$ is an alkyl group, $R_7$ and $R_{27}$ combine together to form either carbon to carbon double bond in the five membered ring structure or a cyclic or aromatic ring, and each of $R_{29}$ and $R_{30}$ (when present) may be selected from hydrogen and trialkylsilyl groups.

In some embodiments, for example, each of $R_{10}$ through $R_{15}$, $R_{21}$, $R_{28}$, and $R_{24}$ is hydrogen, each of $R_8$, $R_9$ and $R_{16}$ is a methyl group, $R_7$ and $R_{27}$ combine together to form either a carbon to carbon double bond in the five membered ring structure or a mononunsaturated cyclobutane moiety, and each of $R_{29}$ and $R_{30}$ (when present) may be selected from hydrogen and trimethylsilyl groups. The configuration in which $R_7$ and $R_{27}$ combine together to form a carbon to carbon double bond in the five membered ring yields the (+)-enantiomer of Formula 17C below and the (−)-enantiomer of Formula 18C below. The configuration in which $R_7$ and $R_{27}$ combine together to form a monounsaturated cyclobutane moiety in which one of $R_{29}$ and $R_{30}$ is a trimethylsilyl group yields the (+)-enantiomer of Formula 17D below and the (−)-enantiomer of Formula 18D below. The configuration in which $R_7$ and $R_{27}$ combine together to form a monounsaturated cyclobutane moiety in each of $R_{29}$ and $R_{30}$ is hydrogen yields the (+)-enantiomer of Formula 17E below and the (−)-enantiomer of Formula 18E below. It is understood that although these configurations are depicted as having each of $R_{10}$ through $R_{15}$, $R_{21}$, $R_{28}$, and $R_{24}$ as hydrogen, any or all of these hydrogen atoms could be substituted with the substituents described above, yielding additional precursors to the (+)-enantiomer and the (−)-enantiomer of Formulae 15 and 16.

Formula 17C

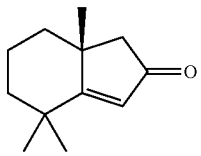

Formula 18C

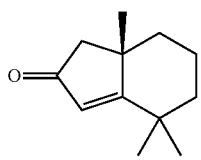

Formula 17D

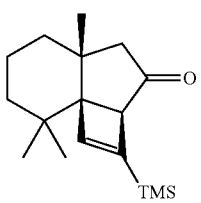

Formula 18D

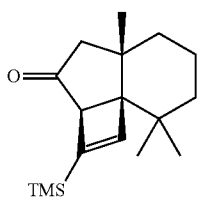

Formula 17E

Formula 18E

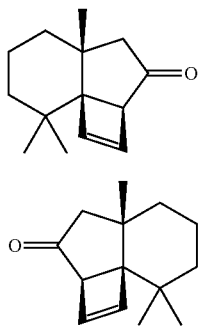

According to other embodiments of the present invention, derivatives of the compounds represented by Formulae 13 and 14 include compounds represented by Formulae 19 and 20, and Formulae 21 and 22, below. These derivatives were serendipitously obtained, as they were unexpectedly produced as a byproduct of the reaction leading to the formation the compounds of Formulae 13 and 14. Although the R groups in Formulae 19, 20, 21 and 22 are somewhat differently labelled (i.e., they are labelled in 100 series numerals rather than 10 series numerals), R groups in Formulae 19-22 having 100 series numerals corresponding to the 10 series numerals listed in the above Formulae 1-18, also have the same definitions. For example, $R_{108}$ in Formulae 19-22 corresponds to $R_8$ in the above Formulae 1-18.

Formula 19

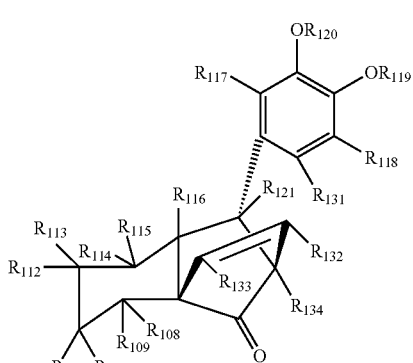

Formula 20

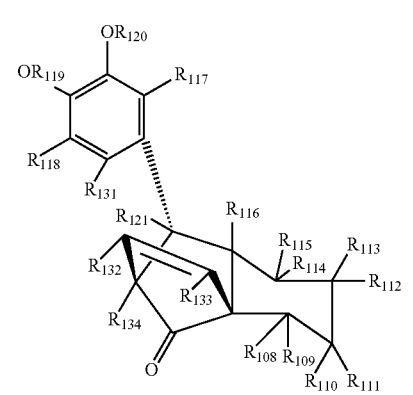

Formula 21

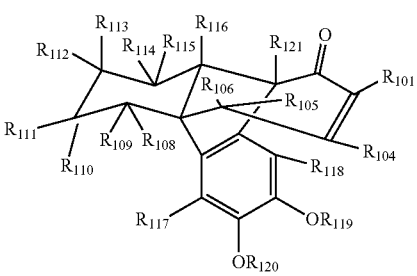

Formula 22

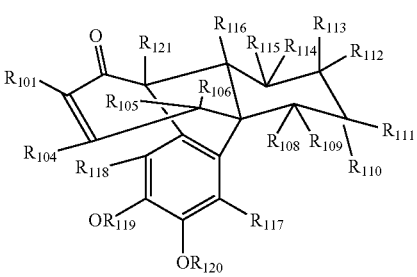

In Formula 19-22, each of $R_{101}$ and $R_{104}$ through $R_{121}$ are as described above with respect to $R_1$ through $R_{22}$ in Formulae 1-18 (i.e., like reference numerals designate like moieties and/or functional groups throughout). Additionally, any two adjacent groups selected from $R_8$ through $R_{16}$ and $R_{21}$ may optionally combine to form a carbon to carbon double bond in the respective rings. Also, $R_{131}$ through $R_{134}$ may be selected from the substituents discussed above for $R_1$ through $R_{22}$, or may be selected from trialkylsilane groups and hydrogen. For example, $R_{131}$ through $R_{134}$ may be selected from hydrogen and trimethylsilyl groups. In some embodiments, however, $R_{131}$ through $R_{134}$ may be hydrogen.

In some exemplary embodiments of the present invention, in Formulae 19-22, each of $R_1$, and $R_4$ through $R_{21}$ is independently selected from hydrogen, carbonyl groups, and alkyl groups, and each of $R_{131}$ through $R_{134}$ (when present) may be selected from hydrogen and trialkylsilyl groups. Also, in some exemplary embodiments, each of $R_1$, and $R_4$ through $R_{21}$ may be selected from hydrogen, aldehyde carbonyl groups and methyl groups, and each of $R_{131}$ through $R_{134}$ (when present) may be selected from hydrogen and trialkylsilyl groups. For example, in some embodiments, each of $R_1$, $R_4$ through $R_6$, $R_{10}$ through $R_{15}$, $R_{17}$, $R_{18}$ and $R_{21}$ is hydrogen, each of $R_8$, $R_9$, $R_{16}$, $R_{19}$ and $R_{20}$ is an alkyl group, and each of $R_{131}$ through $R_{134}$ (when present) may be selected from hydrogen and trialkylsilyl groups.

In some embodiments, for example, each of $R_1$, $R_4$ through $R_6$, $R_{10}$ through $R_{15}$, $R_{17}$, $R_{18}$ and $R_{21}$ is hydrogen, each of $R_8$, $R_9$, $R_{16}$, $R_{19}$ and $R_{20}$ is a methyl group, and each of $R_{131}$ through $R_{134}$ (when present) may be selected from hydrogen and trimethylsilyl groups. These configurations of Formulae 19-22, in which each of $R_{131}$ through $R_{134}$ (when present) is hydrogen yield the (+)-enantiomers of Formulae 19A, 20A, 21A and 22A below and the (−)-enantiomers of Formulae 19B, 20B, 21B and 22B below. It is understood that although these configurations are depicted as having each of $R_1$, $R_4$ through $R_6$, $R_{10}$ through $R_{15}$, $R_{17}$, $R_{18}$ and $R_{21}$ as hydrogen, any or all of these hydrogen atoms could be substituted with the substituents described above, yielding additional derivatives of the (+)-enantiomer and the (−)-enantiomer of Formulae 13 and 14.

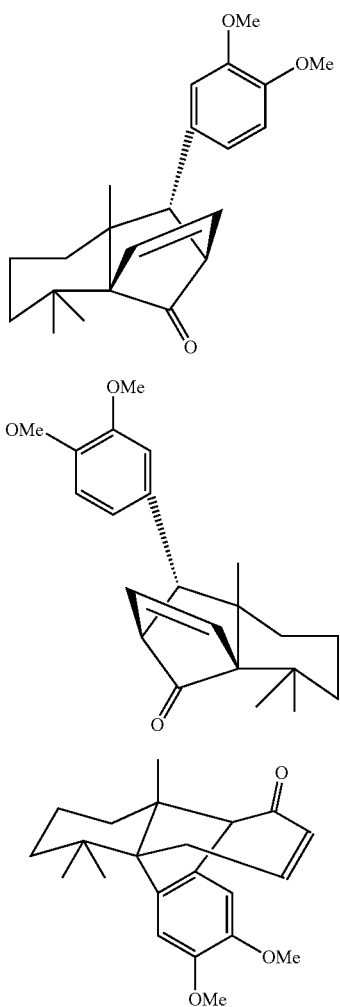

Formula 19A

Formula 20A

Formula 21A

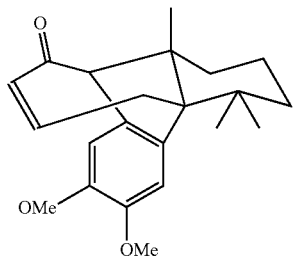

Formula 22A

Some embodiments of the present invention are directed to methods of enantioselectively synthesizing the enantiomeric compositions described above. These methods can be initially understood by devising a retrosynthetic pathway from the ultimate end-product, the enantioselective composition of liphagal (i.e., a non-racemic mixture of the two enantiomers of liphagal). Such a retrosynthetic pathway is illustrated in the following retrosynthetic Reaction Scheme 1.

Reaction Scheme 1 - retrosynthetic from (+)-liphagal

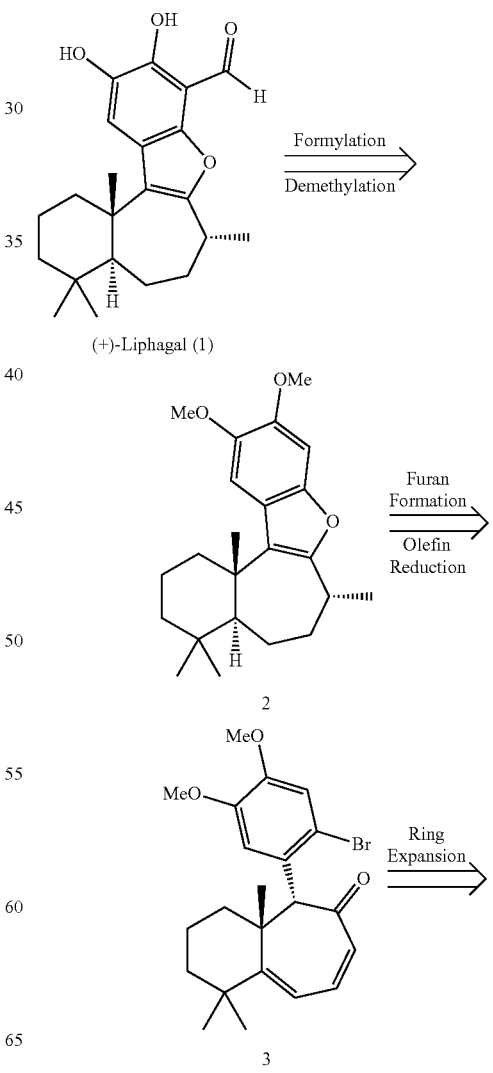

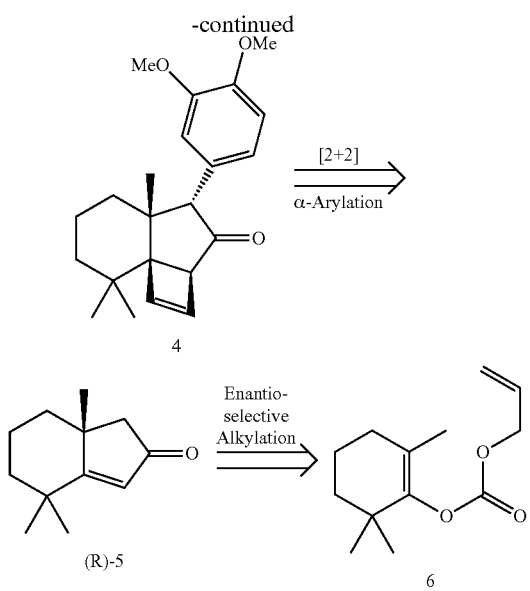

In Scheme 1, looking at a single enantiomer of liphagal (e.g., the (+) enantiomer, represented by Formula 1A above and designated compound 1 in the above Reaction Scheme 1), a first step in the retrosynthetic method is the simplification of the six-membered aromatic ring of liphagal to dimethoxybenzofuran (designated Compound 2 in the above retrosynthetic Reaction Scheme 1). The product designated Compound 2 is a known precursor to the natural liphagal product. Next in the retrosynthetic scheme is the disconnection of the tetracycle along the benzofuran moiety, which leads back to α-bromoaryl dienone (designated Compound 3 in the retrosynthetic Reaction Scheme 1).

Reduction of the sterically hindered tri-substituted olefin to establish the trans ring fusion is a major challenge. The α-bromoaryl dienone (Compound 3) could arise from a ring expansion of strained cyclobutene (designated Compound 4 in the retrosynthetic Scheme 1). Excision of the cyclobutene and α-aryl group from the ketone (i.e., Compound 4) reveals chiral cyclopentenone (designated Compound (R)-5, where R designates the enantiomer of Compound 5) in the retrosynthetic Scheme 1. The S enantiomer of Compound 5 (i.e., the enantiomeric enone (S)-5)) has been previously prepared from achiral enol carbonate (designated Compound 6 in the retrosynthetic Scheme 1). However, a synthesis of the R enantiomer, as depicted in Reaction Scheme 1, has not been reported. Palladium-catalyzed enantioselective decarboxylative alkylation reactions that employ the t-Bu-PHOX ligand scaffold in conjunction with allyl enol-carbonates, silyl enol-ethers, and racemic β-ketoesters has been used to produce a wide array of α-quaternary substituted ketones. With the strategy developed from this retrosynthetic analysis, a total, enantioselective synthesis of (+) or (−) liphagal could be created.

Working backwards from the retrosynthetic analysis, in an embodiment of the present invention, as shown in the following Reaction Scheme 2, the forward synthesis of the liphagal enantiomers commences with a palladium-catalyzed decarboxylative alkylation of enol carbonate (designated compound 6 in Reaction Scheme 2) to furnish a tetrasubstituted ketone (designated compound 7 in Reaction Scheme 2) in 87% yield and 92% enantiomeric excess. As used herein, as discussed above, "enantiomeric excess" (or "ee") is defined as |F(+)−F(−)| (or |F(−)−F(+)| for compositions including more of the (−) enantiomer) for a mixture of (+) and (−) enantiomers, with the composition given as the mole or weight fractions F(+) and F(−), such that F(+)+F(−)=1. When given as a percentage, enantiomeric excess is defined by 100*|F(+)−F(−)| (or 100*|F(+)−F(−)|). This intermediate was elaborated to the bicycle designated Compound 5 following the two-step sequence reported in McFadden, et al., "The Catalytic Enantioselective, Protecting Group-Free Total Synthesis of (+)-Dichroanone," J. Am. Chem. Soc., col. 128, pgs. 7738-7739 (2006), the entire content of which is incorporated herein by reference. The synthesis continues with exposure of the enone designated Compound 5 to trimethylsilylacetylene under UV irradiation, which promotes a [2+2] photocycloaddition. Exposure of the crude reaction mixture to $BF_3 \cdot OEt_2$ forms a single silylated cyclobutene product (designated Compound 8a). Subsequent removal of the trimethylsilyl group with TBAF yields the chromatographically stable and pleasantly fragrant cyclobutene designated Compound 8b, which is a compound that contains three contiguous quaternary centers within the strained carbon framework. A microwave-assisted palladium-catalyzed α-arylation with 4-bromoveratrole installs the electron rich aromatic moiety, producing the aryl ketone designated Compound 4 as a single diastereomer.

Reaction Scheme 2 - Forward synthesis of (+)-liphagal (Part 1) - Catalytic enantioselective preparation of synthetic building block (+)-7 and chemical elaboration to (+)-4

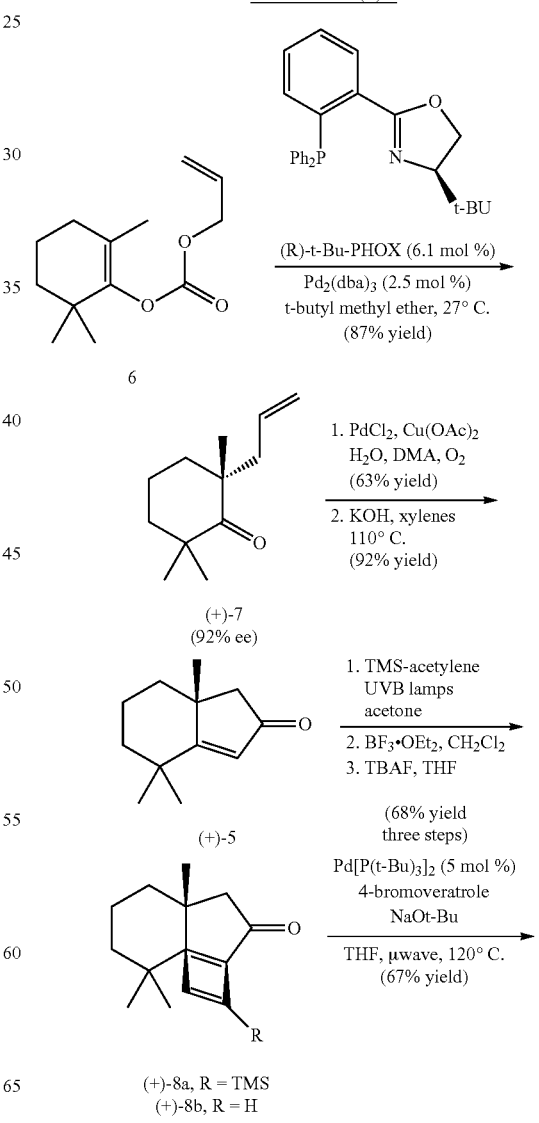

-continued

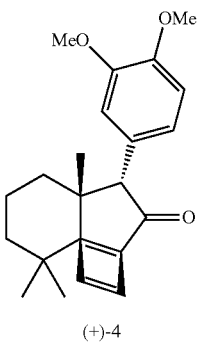

(+)-4

Upon synthesizing Compound 4 (from Reaction Scheme 2), Lewis acid-mediated ring expansion by selective cleavage of the strained cyclobutane (Compound 4) can be attempted by exposure of the tricyclic ketone (Compound 4) to $BF_3.OEt_2$ at 50° C. However, as shown in Reaction Scheme 3 below, this process provides the desired cycloheptadienone product (Compound 9) in modest yield. Serendipitously, it was found that this compound can be isolated alongside a crystalline byproduct (i.e., Compound 10), which is suitable for X-ray diffraction analysis and structure determination. Bridged polycyclic ketone (Compound 10) is presumably the result of a Cargill rearrangement, which proceeds through two concerted [1,2]-carbon-carbon bond migrations. More specifically, activation of the ketone (Compound 4) with $BF_3$ (yielding Compound 11) promotes carbon bond migration to rupture the cyclobutene and produce an allylic carbocation intermediate (Compound 12). The second carbon bond migration forms a [2.2.1] bridged bicyclic core of a Lewis acid complex (Compound 13). Finally, loss of $BF_3$ reveals the isolated product (Compound 10). Importantly, the stereospecific rearrangement mechanism allows assignment of the relative stereochemistry of cyclobutenes (Compound 8 in Reaction Scheme 2) from the unequivocal assignment of the bridged bicycle (Compound 10 in Reaction Scheme 3).

In addition to $BF_3.OEt_2$, it was discovered that $AlCl_3$ also promotes ring expansion of the aryl cyclobutene (Compound 4) without formation of the Cargill product (Compound 10). However, under these reaction conditions, a new side-product was surprisingly found, i.e., an enone (Compound) arising from an intramolecular 1,6-addition of the electron-rich arene fragment of Compound 9 to the cycloheptadienone system. This result suggests that the arene resides in close proximity to the tri-substituted olefin and also indicates that the aromatic moiety should be deactivated before ring expansion to avoid formation of Compound 14. However, while the formation of Compounds 10 and 14 may not be desirable in the total, enantioselective synthesis of a liphagal enantiomer, these derivatives have structures similar to other precursors in the total synthesis, and therefore would be expected to have similar properties.

Reaction Scheme 3 - Unexpected rearrangement and reactivity of strained cyclobutane

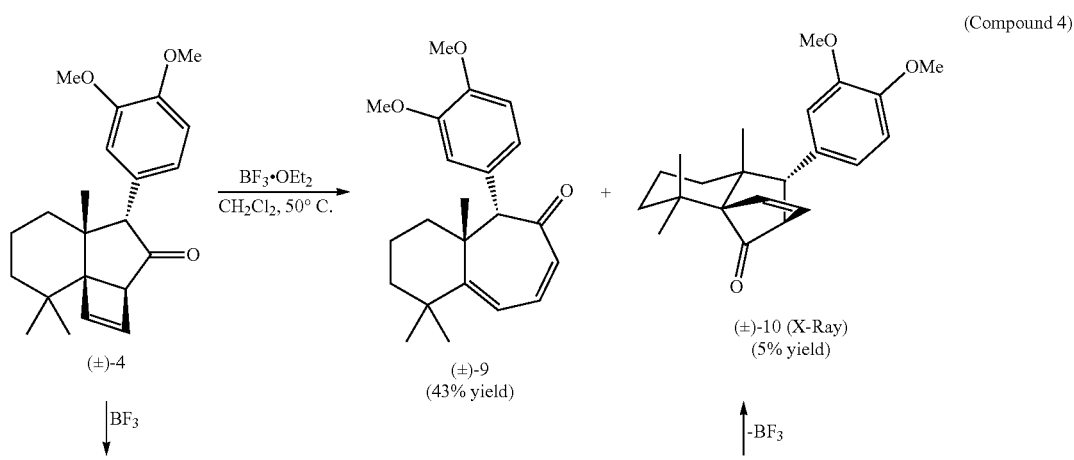

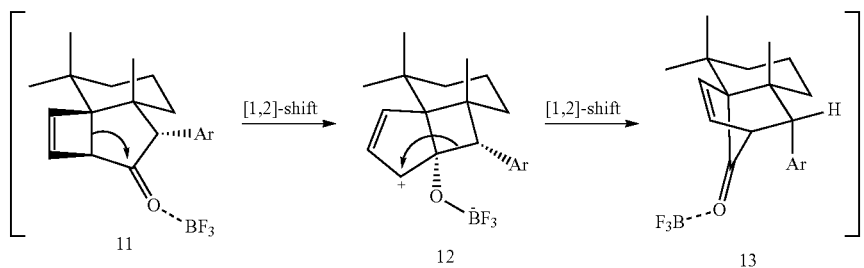

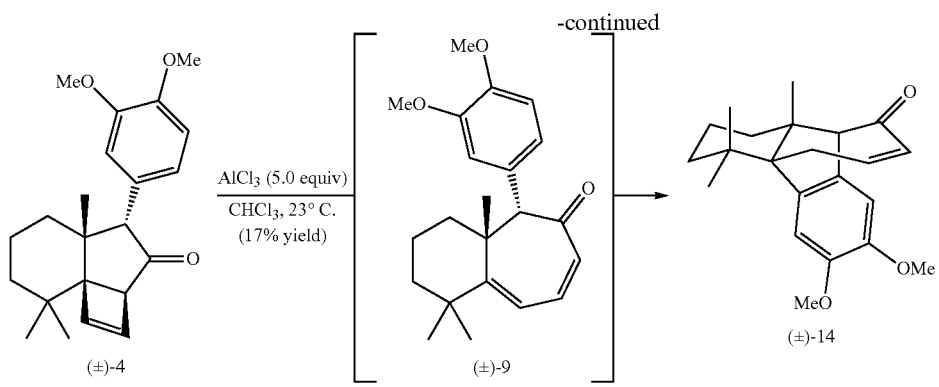

Next, as shown in Reaction Scheme 4 below, a functional group handle is installed on the aromatic ring. The functional group could be utilized for eventual benzofuran formation and could serve to deactivate the aromatic residue of Compound 9 toward unwanted Friedel-Crafts chemistry. It was found that chemoselective aromatic bromination occurs in the presence of the strained cyclobutene, furnishing a bromoarene (Compound 15 shown in Reaction Scheme 4 below). At this stage, crystallization of the crude product increases the enantiomeric excess to >99%. With the deactivated aromatic ketone in hand, it was found that treatment of the bromide (Compound 15) with $AlCl_3$ furnishes much improved yields of the corresponding ring expanded product (Compound 3). An optimized ring expansion from the [6-5-4] system to the desired [6-7] core (Compound 3) can be accomplished in the absence of a Lewis acid with microwave heating at about 250° C. in o-dichlorobenzene. Chemoselective reduction of the dienone (Compound 3) with Adams' catalyst in ethyl acetate furnishes a ketone (Compound 16), leaving the aromatic halide intact.

With the core carbon framework of liphagal (the (+) enantiomer depicted as Compound 1) secured, the focus now turned to the challenging stereoselective hydrogenation of the tri-substituted olefin to establish the desired [6-7] trans ring fusion. The strategy to effect this transformation was guided by the previous isolation of the 1,6-addition product (Compound 14 in Reaction Scheme 3), which provided evidence that hydrogenation to form a trans ring fusion would be sterically demanding. To alleviate steric congestion, epimerization of the aryl substituent can be carried out, forming a β-oriented α-aryl ketone (Compound 17). The mass recovery for this equilibration averages 97% and a 78% overall yield of Compound 17 may be obtained after three cycles of equilibration ($K_{eq(av)}$=0.76). With the arene substituent further removed from the tri-substituted olefin, the plan was to rigidify the polycyclic system via formation of the fourth ring. This began with a diastereoselective methylation, affording the desired α-methyl cycloheptenone (18) in 68% yield. Reduction of this hindered ketone with diisobutyl aluminium hydride (DIBAL) produced an alcohol (Compound 19), a substrate poised for dihydrobenzofuran formation.

However, initial attempts to form dihydrobenzofuran (Compound 21) were unsuccessful and prompted an unconventional strategy to accomplish the desired transformation. Formation of the dihydrobenzofuran (Compound 21) may be accomplished upon exposure of the bromoarene (Compound 19) to lithium diisopropylamide (LDA), proceeding through a putative aryne intermediate (Compound 20). This powerful aryne capture cyclization strategy generates the highly congested dihydrobenzofuran product in 83% yield. With the tetracycle (Compound 21) in hand, the key stereoselective hydrogenation of the tri-substituted olefin was tested. Using catalytic Pd/C in ethanol under 1 atm $H_2$, 97% yield of the saturated homodecalin (Compound 22) can be isolated, and exclusive formation of the [6-7] trans ring fusion is observed.

Having executed the synthesis of the challenging trans fused ring system, the completion of (+)-liphagal required three additional transformations: 1) benzofuran construction, 2) aldehyde installation, and 3) demethylation, the final two of which are known from previous syntheses (e.g., in Marion, et al., "Liphagal, a Selective Inhibitor of PI3 Kinase α Isolated from the Sponge Aka caralliphaga: Structure Elucidation and Biomimetic Synthesis," Org. Lett., vol. 8, no. 2, pgs. 321-324 (2006), and George, et al., "Enantiospecific, Biosynthetically Inspired Formal Total Synthesis of (+)-Liphagal," Org. Lett., vol. 12, no. 10, pgs. 2394-2397 (2010), the entire contents of which are incorporated herein by reference.

Oxidation of the dihydrobenzofuran (Compound 22) to the benzofuran (Compound 2) proved surprisingly difficult, and with 2,3-dichloro-5,6-dicyano-1,4-benzoquinone (DDQ) a tendency for over-oxidation can be observed. Upon switching to nitrosonium tetrafluoroborate, which oxidizes by hydride abstraction, dehydrogenation occurs in 70% yield to give the benzofuran of Compound 2. Aryl lithiation with n-butyllithium.TMEDA (tetramethylethylenediamine) and quenching with anhydrous dimethylformamide (DMF) installs the aldehyde functional group in the compound designated Compound 23. Finally, this may be followed by demethylation using boron triiodide to generate (+)-liphagal (Compound 1), which is identical in all respects to data reported in the literature for the natural product.

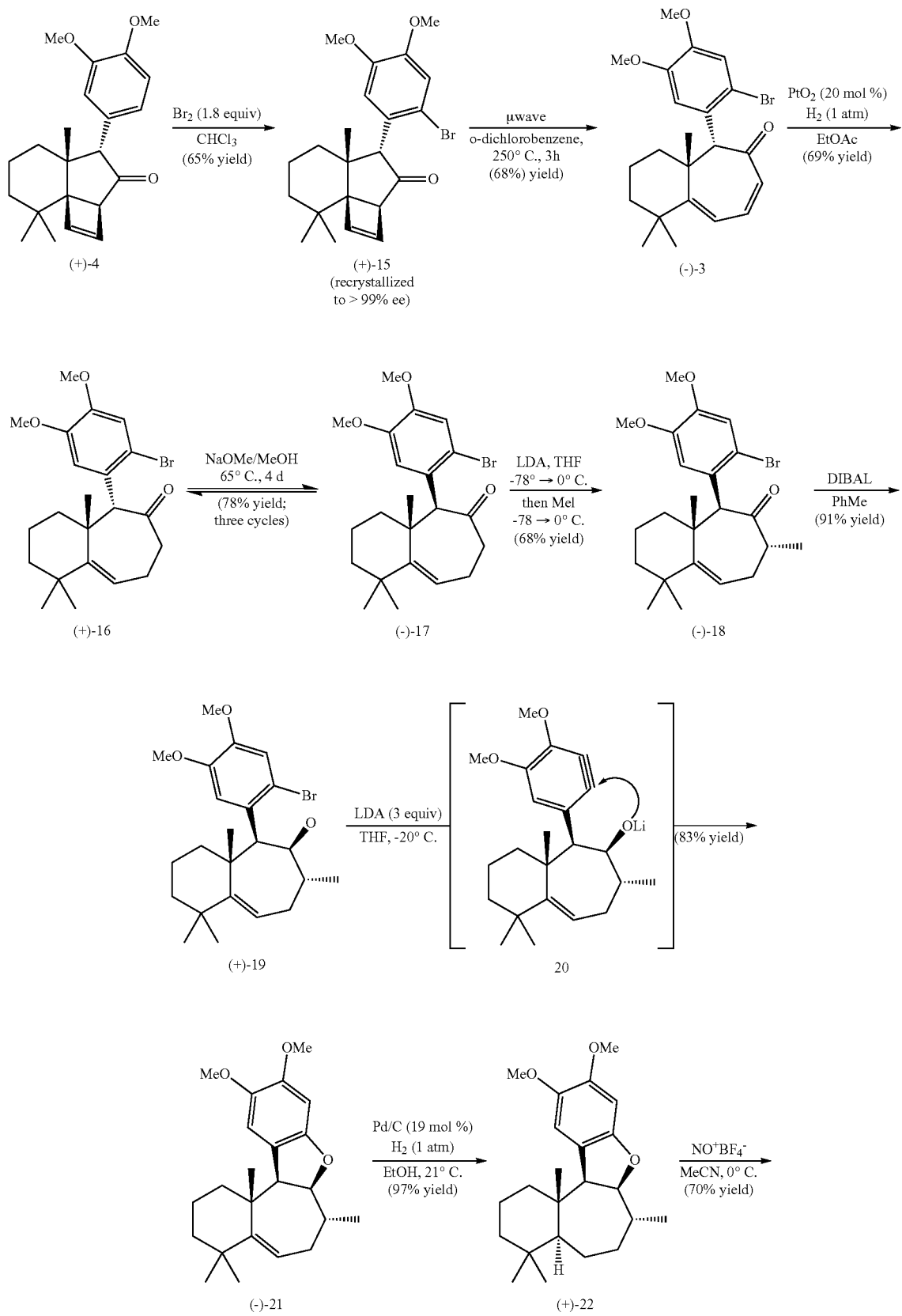

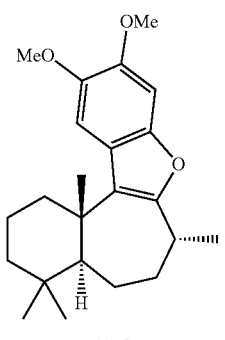
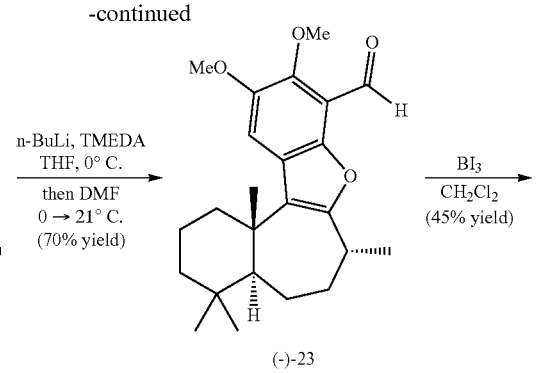

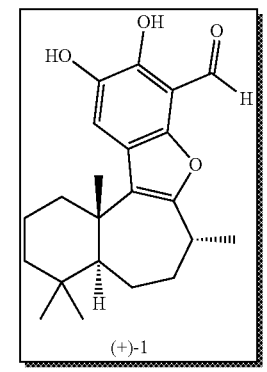

The above described process represents the first catalytic enantioselective total synthesis of (+)-liphagal, and accomplishes this feat in 15 steps from known compounds (and 19 steps from commercially available materials). Applying a combination of catalytic enantioselective alkylation (Compound 6→Compound 7), two-carbon ring expansion via cyclobutene (Compound 15), and an intramolecular aryne cyclization (Compound 19→Compound 20→Compound 21) enables access to the tetracyclic core of the natural product in enantioenriched form. Judicious choice of the tetracyclic hydrogenation substrate (Compound 21) establishes the critical trans-[6-7] ring fusion and enables completion of the total synthesis.

Given the above discussion of the synthesis of the (+) liphagal enantiomer, those of ordinary skill in the art would readily recognize that a corresponding synthesis method could be used to synthesize the (−) liphagal enantiomer in a similar enantioenriched form. Specifically, those of ordinary skill in the art would recognize that replacing the above disclosed reactants with their enantiomers would yield the (−) liphagal enantiomer in enantioenriched form. For example, to make the (−) enantiomer, the starting reactants, i.e., Compounds 6 and 7 in Reaction Scheme 2 would be replaced with their enantiomers, which are represented by Compounds 6A and 7A, below. Also, the reactant used to effect transformation of Compound 6 to Compound 7 would be replaced with its enantiomer. The reactant depicted in Scheme 2 above is represented by Reactant A below, and the enantiomer of this reactant used in the production of the (−) liphagal enantiomer is depicted as Reactant A' below. The remaining compounds in Schemes 2 through 4 are similarly replaced with their enantiomers, which are described above in Formulae 1 through 22.

Compound 6A
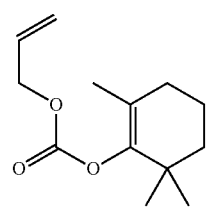

Compound 7A
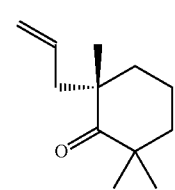

Reactant A
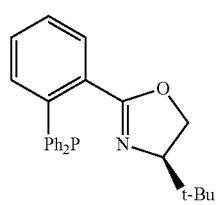

Reactant A'
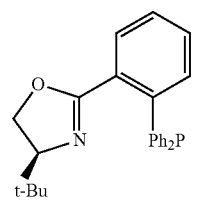

Although the above synthesis method is described as yielding the specific structure of the liphagal enantiomers, it is understood that similar methods can be used to prepare the derivatives and precursors (discussed above with respect to Formulae 1 through 22) to the liphagal enantiomers. In particular, according to certain embodiments of the present invention, a method of making an enantiomer represented by Formula 1 includes procedures analogous to those described above with respect to the production of (+) liphagal.

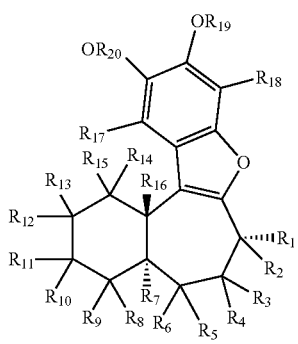

Formula 1

For example, in some embodiments of the present invention, a method of making an enantioenriched composition includes enantioselective catalytic alkylation of a first precursor compound to form a second precursor compound; oxidation and condensation of the second precursor compound to form a third precursor compound; promotion of a photocycloaddition reaction of the third precursor compound to form a fourth precursor compound; exposure of the fourth precursor product to a Lewis acid to form a fifth precursor compound; arylation of the fifth precursor compound to form a sixth precursor compound; functionalization of an aromatic group on the sixth precursor compound to form a seventh precursor compound; ring expansion of the seventh precursor compound to form an eighth precursor compound; reduction of the eighth precursor compound to form a ninth precursor compound; reduction of steric congestion in the ninth precursor compound to form a tenth precursor compound; intramolecular aryne cyclization of the tenth precursor compound to form a thirteenth precursor compound; stereoselective hydrogenation (or substitution) of the thirteenth precursor compound to form a fourteenth precursor compound; and oxidation of the fourteenth precursor compound to form a fifteenth precursor compound.

The method may further include functionalization of the fifteenth precursor compound to form a compound of Formula 1, and/or demethylation (or desubstitution) of the compound of Formula 1 (or the fifteenth precursor compound) to yield a different compound of Formula 1. For example, demethylation (or desubstitution) of the fifteenth precursor compound could result in the formation of a compound of Formula 1 in which all of $R_{18}$, $R_{19}$ and $R_{20}$ are hydrogen. Also, in some embodiments, the intramolecular aryne cyclization includes stereoselective substitution of the tenth precursor to form an eleventh precursor; reduction of the eleventh precursor to form a twelfth precursor; and exposure of the twelfth precursor to a strong base to form the thirteenth precursor. Additionally, reduction of the steric congestion may be accomplished by epimerization of an aryl substituent of the ninth precursor compound to form the tenth precursor compound. Also, as used herein, the term "strong base" is used in its art-recognized sense, and is not intended to be a term of degree. Some nonlimiting examples of some art-recognized strong bases include hydroxides of alkali and alkaline earth metals, as well as LDA.

In the method of making the enantiomer of Formula 1, according to an embodiment of the present invention, the first precursor compound may be an enol carbonate of Formula 100, below, and is subjected to palladium-catalyzed decarboxylative alkylation to yield the second precursor compound, which can be a tetrasubstituted ketone of Formula 110, below. In Formulae 100 and 110, all like numbered R groups are as described above with respect to $R_1$ through $R_{22}$, and $R_{200}$ through $R_{204}$ may include the substituents described above with respect to $R_1$ through $R_{22}$.

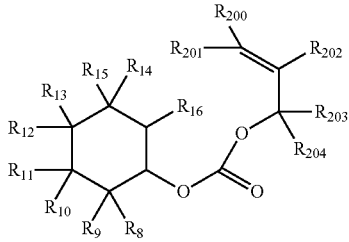

Formula 100

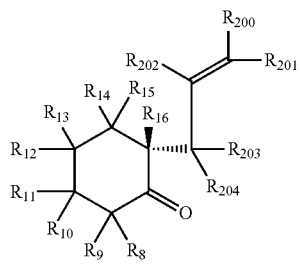

Formula 110

In the palladium-catalyzed decarboxylative alkylation, the compound of Formula 100 is reacted with Reactant A (above) (i.e., (R)-t-Bu-PHOX (4-(1,1-dimethylethyl)-2-[2-(diphenylphosphino)phenyl]-r,5-dyhydro-(4S)-oxazole)) in the presence of a $Pd_2(dba)_3$ catalyst in t-butyl methyl ether at a temperature of about 25 to about 30° C., for example about 27° C. Synthesis of the S enantiomer of t-Bu-PHOX has been reported, e.g., in Krout, et al., "Preparation of (S)-tert-ButylPHOX," Org. Synth., vol. 86, pgs. 181-193 (2009), the entire content of which is incorporated herein by reference. Those of ordinary skill in the art would readily understand a method of making the (R) enantiomer from the description of the (S) enantiomer. Also, although $Pd_2(dba)_3$ and t-butyl methyl ether are disclosed here as the catalyst and solvent in this reaction, it is understood that any suitable palladium catalyst and solvent may be used. Reactant A is present in this reaction in an amount of about 5 to about 10 mol %, for example, about 6.1 mol %, and the palladium catalyst is present in this reaction in an amount of about 1 to about 5 mol %, for example about 2.5 mol %. The reaction yields the compound of Formula 110 in a yield of about 80 to about 90%, for example about 87%, and an enantiomeric excess of about 85 to about 95%, for example about 92%.

After forming the second precursor compound (e.g., the compound of Formula 110), that compound is subjected to the two-step reaction sequence (i.e., oxidation and condensation) reported in McFadden, et al., "The Catalytic Enantioselective, Protecting Group-Free Total Synthesis of (+)-Dichroanone," J. Am. Chem. Soc., vol. 128, pgs. 7738-7739 (2006), the entire content of which is incorporated by reference. In particular, the second precursor compound (e.g., the compound of Formula 110) is first subjected to a Wacker oxidation using $PdCl_2$, $Cu(OAc)_2.H_2O$, dimethylacetamide (DMA) and $O_2$, and then to condensation using KOH in xylenes. This procedure yields the third precursor compound, which can be the compound of Formula 17B discussed above (and reproduced below) in a yield of about 85 to about 95%, for example about 92%.

Formula 17B

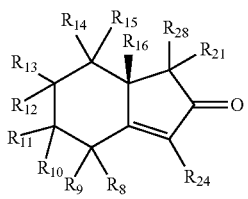

In the Wacker oxidation, the reaction can be carried out in a Parr apparatus, the $PdCl_2$ may be present in the reaction in an amount of about 3 to about 10 mol %, for example about 5 mol %, the $Cu(OAc)_2.H_2O$ may be present in the reaction in an amount of about 20 to about 30 mol %, for example about 25 mol %, the $O_2$ pressure may be about 1 atm, and the temperature of the reaction can be from about 20 to about 25° C., for example about 23° C. Also, the DMA solvent may be diluted with water, for example a ratio of DMA to water of about 7:1. Additionally, while the Wacker oxidation is described here as including $PdCl_2$, $Cu(OAc)_2.H_2O$, and DMA, it is understood that any other suitable reactants, catalysts and solvents could alternatively be used. The reaction may take place in a Parr apparatus and may take about 20 to about 30 hours to complete, for example about 24 hours.

The condensation reaction can be effected with about 0.3 to about 0.6 equivalents of powdered KOH in xylenes at a temperature of about 100 to about 120° C., for example about 110° C. Additionally, the reaction can take place in a Dean-Stark apparatus, and may take from about 10 to about 12 hours, for example about 11 hours. Also, although this reaction is described as using KOH in xylenes, it is understood that any other suitable base and solvent could alternatively be used. After oxidation and condensation, the third precursor compound (e.g., the compound of Formula 17B) is produced in a yield of about 85 to about 95%, for example, about 92%.

Next, photcycloaddition of the third precursor compound (e.g., the compound of Formula 17B) is promoted. This can be accomplished by exposure of the third precursor compound to trialkylsilylacetylene (e.g., trimethylsilylacetylene) under UV irradiation, which promotes a [2+2] photocycloaddition, yielding the fourth precursor compound. The crude reaction mixture (i.e., the fourth precursor compound) may then be exposed to a Lewis acid, such as $BF_3.OEt_2$, in a solvent (e.g., dichloromethane) to form the fifth precursor compound (substituted with TMS), which can be the single silylated cyclobutene product represented by Formula 17A discussed above (and reproduced below) in which $R_{29}$ is TMS. The TMS group may be removed with any suitable compound, such as TBAF (tetrabutyl ammonium fluoride) in a solvent (e.g., tetrahydrofuran (THF)), yielding the fifth precursor compound (without the TMS group) which may be a chromatographically stable and pleasantly fragrant cyclobutene compound represented by Formula 17A discussed above (and reproduced below) in which $R_{29}$ is hydrogen in yield of about 65 to about 75%, for example about 68%. This compound has three contiguous quaternary centers within the strained carbon framework.

Formula 17A - $R_{29}$ is TMS or hydrogen

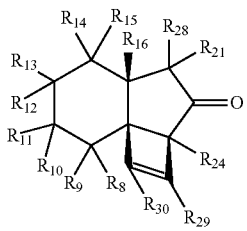

The fifth precursor compound (e.g., the compound of Formula 17A in which $R_{29}$ is hydrogen) is then subjected to a microwave-assisted palladium-catalyzed α-arylation with 4-bromoveratrole and NaOt-Bu in THF. This procedure yields the sixth precursor compound, which may be an aryl ketone represented by Formula 15 (described above and reproduced below) in which X' is hydrogen in a yield of about 60 to about 75%, for example about 67%. Although this procedure is described as using 4-bromoveratrole, it is understood that any suitable haloveratrole could be used, for example iodoveratrole, fluoroveratrole, chloroveratrole, etc. Also, although any suitable palladium catalyst can be used in this reaction, in some embodiments the palladium catalyst can be $Pd[P(t-Bu)_3]_2$. In some embodiments, the amount of the palladium catalyst may be about 3 to about 10 mol %, for example about 5 mol %. Also, although NaOt-Bu and THF are described in this reaction, it is understood that any suitable alternatives may also be used. Additionally, the reaction may be carried out at any suitable temperature, for example a temperature of about 100 to about 140° C., for example 120° C.

Formula 15

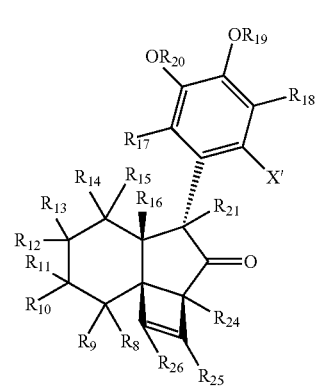

Next, a functional group handle is installed on the aromatic ring of the sixth precursor compound (e.g., the compound of Formula 15) to form the seventh precursor compound. Specifically, the sixth precursor compound (e.g., the compound of Formula 15 in which X' is hydrogen) is reacted with a halide (e.g., $Br_2$) in the presence of a solvent (e.g., trichloromethane). Surprisingly, under these conditions, chemoselective aromatic halogenation (e.g., bromination) occurs in the presence of the strained cyclobutene of Formula 15, yielding the seventh precursor compound, which may be a haloarene (e.g., a bromoarene) compound of Formula 15 in which X' is a halogen (e.g., Br) in a yield of about 60 to about 70%, for example about 65%. Recrystallization may also be performed in order to increase the enantiomeric excess. Indeed, recrystallization can increase the enantiomeric excess to greater than 99%. Also, the haloarene compound of Formula 15 in which X' is a halogen (e.g., Br) may be further treated with a Lewis acid, such as $AlCl_3$, which surprisingly improves the yield (in the next process of the method) of the ring expanded product, i.e., the eighth precursor compound which may be represented by Formula 13.

The seventh precursor compound, which may be the haloarene product of Formula 15 in which X' is a halogen (e.g., Br), is then subjected to ring expansion to form the eighth precursor compound. Specifically, expansion from the [6-5-4] system in Formula 15 to the [6-7] core in the compounds of Formula 13 is effected in the absence of a Lewis acid by using microwave heating at a temperature of about 200 to about 300° C., for example 250° C., in a solvent (e.g., o-dichlorobenzene). This reaction can be carried out for about 2 to about 5 hours, for example about 3 hours, and produces the eighth precursor compound (which can be the ring expanded product of Formula 13) in a yield of about 65 to about 75%, for example about 68%.

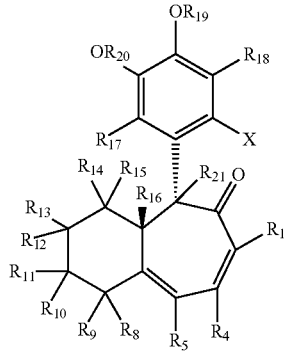

Formula 13

Chemoselective reduction is then performed on the eighth precursor compound (which can be the compound of Formula 13) using a catalyst (e.g, Adam's catalyst) in a solvent (e.g., ethyl acetate), producing the ninth precursor compound (which can be the compound of Formula 11B (reproduced below)) while leaving the aromatic halide intact. Specifically, the ninth precursor compound (e.g., the compound of Formula 13) is reduced using $PtO_2$ and $H_2$ in ethyl acetate. The $PtO_2$ may be present in this reaction in an amount of about 15 to about 25 mol %, for example about 20 mol %, and the $H_2$ may be at about 1 atm pressure. These conditions produce the ninth precursor compound (e.g, the compound of Formula 11B) in a yield of about 65 to about 75%.

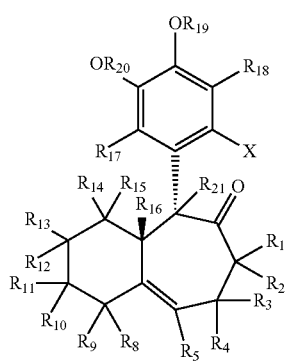

Formula 11B

Next, epimerization of the aryl substituent of the ninth precursor compound is performed to form the tenth precursor compound, which can be a β-oriented α-aryl ketone represented by Formula 11A (reproduced below). Specifically, the epimerization may be carried out in NaOMe/MeOH at a temperature of about 60 to about 70° C., for example 65° C., for about 3 to about 5 days, for example about 4 days. The mass recovery for this equilibration may average about 95 to about 99%, for example about 97%. An overall yield of the tenth precursor compound (e.g, the compound of Formula 11A) of about 75 to about 85% may be achieved after about three cycles of equilibration ($K_{eq(av)}$=0.76).

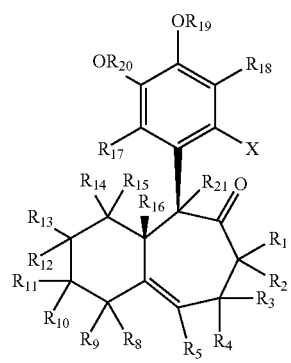

Formula 11A

Diastereoselective methylation is performed on the tenth precursor compound (e.g., the compound of Formula 11A) to yield the eleventh precursor compound (e.g., an α-substituted cycloheptanone of Formula 11C) in a yield of about 65 to about 75%, for example about 68%. Specifically, the tenth precursor compound (e.g., the compound of Formula 11A) is first treated with lithium diisopropylamide in tetrahydrofuran at a temperature of about −75 to about −85° C., e.g., about −78° C., and is then reacted with a halide substituent (e.g., an alkyl iodide, such as iodomethane) at a similar temperature, i.e., about −75 to about −85° C., e.g., about −78° C., to complete the substitution (e.g., alkylation or methylation).

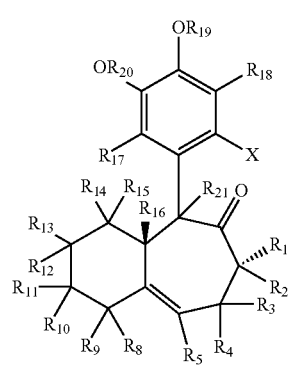

Formula 11C

Although not depicted in Formula 11C, it is understood that, according to this description, the stereochemistry of the bond between the seven-membered ring and the six-membered aromatic ring is the same as that depicted in FIG. 11A.

The eleventh precursor compound (e.g., the hindered ketone of Formula 11C) is then reduced to produce the twelfth precursor compound (e.g., the alcohol represented by Formula 9), which is a substrate poised for dihydrobenzofuran formation. This reduction reaction is carried out using DIBAL (diisobutyl aluminum hydride) in a solvent (e.g., toluene (abbreviated PhMe in the reaction schemes)), and produces the twelfth precursor compound (e.g., the alcohol of Formula 9) in a yield of about 85 to about 95%, for example about 91%.

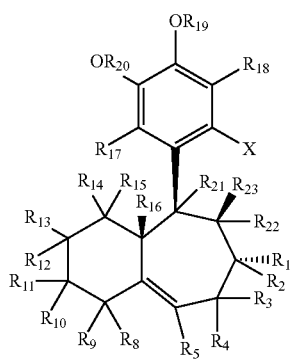

Formula 9

The twelfth precursor compound (e.g., the bromoarene compound of Formula 9) is then exposed to a base, such as lithium diisopropylamide (LDA), leading to the formation of the thirteenth precursor compound, which can be the dihydrobenzofuran compound represented by Formula 5. Specifically, the twelfth precursor compound (e.g., the compound of Formula 9) is exposed to the base (e.g., LDA) in the presence of a solvent (e.g., THF), and the reaction may be carried out at a temperature of about −15 to about −25° C., for example −20° C. This reaction may proceed through a putative aryne intermediate represented by Formula 7. Also, this reaction produces the thirteenth precursor compound (e.g., the highly congested dihydrobenzofuran product of Formula 5) in a yield of about 80 to about 90%, for example, about 83%.

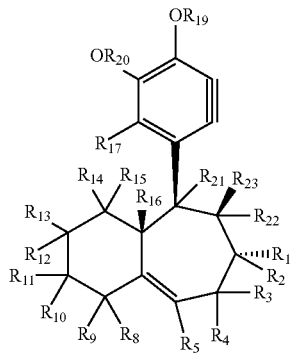

Formula 7

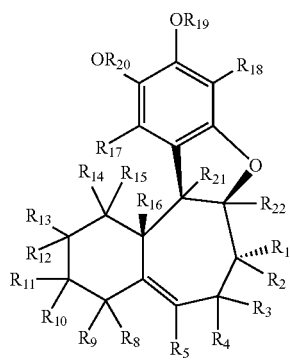

Formula 5

The thirteenth precursor compound (e.g, the compound of Formula 5) may then be stereoselectively hydrogenated (or substituted) to form the fourteenth precursor compound, which may be the homodecalin product represented by Formula 3. To effect stereoselective hydrogenation, the thirteenth precursor compound (e.g., the compound of Formula 5) may be subjected to a catalyst in a solvent under about 1 atm $H_2$. In some embodiments, the catalyst is Pd/C and the solvent is ethanol, but the present invention is not limited thereto, and any suitable alternative catalyst and/or solvent may also be used. Additionally, the amount of the catalyst is not particularly limited, but in some embodiments, the amount of the catalyst may be about 15 to about 25 mol %, for example, about 20 mol %. Also, this reaction can be carried out at any suitable temperature, for example a temperature of about 15 to about 25° C. In some embodiments, for example, the reaction temperature may be about 21° C. This reaction can produce the fourteenth precursor compound (e.g., the saturated homodecalin compound of Formula 3) in a yield of about 90 to about 100%, for example about 97%.

As would be understood by those of ordinary skill in the art, stereoselective installation of a substituent other than hydrogen could be accomplished by a number of processes, which would depend on the substituent to be installed. However, in some embodiments, stereoselective installation of a substituent other than hydrogen can be accomplished using standard diastereoselective olefin mono or difunctionalization methods, for example, dihydroxylation, epoxidation, hydroamination, carboamination, Diels-Alder reactions, etc.

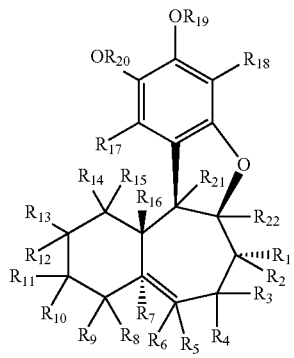

Formula 3

Next, the fourteenth precursor compound (e.g., the saturated homodecalin compound of Formula 3) may be oxidized to form the benzofuran compound represented by Formula 1 in which $R_{19}$ and $R_{20}$ are each an alkyl group (e.g., a methyl group), and $R_{18}$ is hydrogen. The oxidation may be carried out using DDQ (2,3-dichloro-5,6-dicyanobenzoquinone), however, this may lead to over-oxidation. Therefore, according to another embodiment, the oxidation may be carried out using nitrosonium tetrafluoroborate, which oxidizes via hydride abstraction. Using nitrosonium tetrafluoroborate, dehydrogenation to produce the benzofuran compound of Formula 1 (in which $R_{19}$ and $R_{20}$ are each an alkyl group (e.g., a methyl group), and $R_{18}$ is hydrogen) may occur in a yield of about 65 to about 75%, for example about 70%. Also, this reaction may occur in the presence of any suitable solvent (e.g., acetonitrile, designated MeCN in the schemes above), and may be performed at any suitable temperature, such as a temperature of about −10 to about 10° C., for example about 0° C.

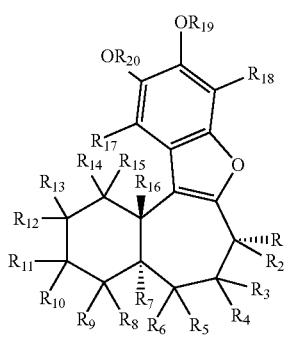

Formula 1

A functional group may then be installed at the $R_{18}$ position in the compound of Formula 1 (in which $R_{19}$ and $R_{20}$ are each an alkyl group (e.g., a methyl group), and $R_{18}$ is hydrogen). Specifically, an aldehyde functional group may be installed through aryl lithiation followed by quenching. The aryl lithiation may be accomplished with n-butyllithium.TMEDA, and the quenching may be accomplished with anhydrous DMF (dimethylformamide). In particular, the aryl lithiation reaction may involve reaction with the n-butyllithium.TMEDA in a solvent (e.g., THF) at a temperature of about −10 to about 10° C., for example about 0° C. The quenching reaction may be performed using anhydrous DMF, and the quenching may be conducted by ramping the temperature from about 0° C. to about room temperature, e.g., from about 0° C. to about 21° C., and the reaction may take about 30 minutes to about 1.5 hours, for example about 1 hour. This aldehyde installation procedure is discussed in George, et al., "Enantiospecific, Biosynthetically Inspired Formal Total Synthesis of (+)-Liphagal," Org. Lett., vol. 12, no. 10, pgs. 2394-2397 (2010), the entire content of which has been previously incorporated herein by reference. This reaction yields the compound of Formula 1 in which $R_{19}$ and $R_{20}$ are each an alkyl group (e.g., a methyl group), and $R_{18}$ is an aldehyde carbonyl group, and the yield of the reaction is about 65 to about 75%, for example about 70%.

Finally, the compound of Formula 1 (in which $R_{19}$ and $R_{20}$ are each an alkyl group (e.g., a methyl group), and $R_{18}$ is an aldehyde carbonyl group) may be demethylated to produce the compound of Formula 1 in which $R_{19}$ and $R_{20}$ are each hydrogen, and $R_{18}$ is an aldehyde carbonyl group (i.e., derivatives of liphagal). Demethylation may be accomplished with a boron trihalide (e.g., boron triiodide) and the reaction is carried out in a suitable solvent (e.g., dichloromethane). This reaction is discussed in Marion, et al., "Liphagal, a Selective Inhibitor of PI3 Kinase a Isolated from the Sponge Aka coralliphaga: Structure Elucidation and Biomimetic Synthesis," Org. Lett., vol. 8, no. 2, pgs. 321-324 (2006), the entire content of which has previously been incorporated herein by reference. This reaction produces the compound of Formula 1 (in which $R_{19}$ and $R_{20}$ are each hydrogen and $R_{18}$ is an aldehyde carbonyl group) in a yield of about 40 to about 50%, for example about 45%.

According to other embodiments of the present invention, methods of making the compounds of Formula 19-22 discussed above generally follow the same procedures as the methods described above to make the compounds of Formulae 1 through 18. However, to make the compounds of Formulae 19-22, the method deviates from the above described method after the microwave-assisted palladium-catalyzed α-arylation of the compound of Formula 17A in which $R_{29}$ is hydrogen. Specifically, to make a compound represented by Formula 19, a Lewis-acid mediated ring expansion is performed through selective cleavage of the strained cyclobutene of the compound of Formula 17A in which $R_{29}$ is hydrogen.

Specifically, the tricyclic ketone of Formula 17A in which $R_{29}$ is hydrogen is exposed to $BF_3.OEt_2$ in a solvent (e.g., dichloromethane) at a temperature of about 40 to about 60° C., for example about 50° C., yielding the compound of Formula 13 in a yield of about 40 to about 50%, but also yielding the compound of Formula 19 in a yield of about 3 to about 10%. The bridged polycyclic ketone of Formula 19 is presumably the result of a Cargill rearrangement, which proceeds through two concerted [1,2]-carbon-carbon bond migrations (as shown in Reaction Scheme 3 depicted and discussed above). More specifically, activation of the ketone of Formula 17A in which $R_{29}$ is hydrogen with $BF_3$ (i.e., as shown in Compound 11 in Reaction Scheme 3 above) promotes bond migration to rupture the cylobutene and produce an allylic carbocation intermediate (i.e., Compound 12 in Reaction Scheme 3 above). The second carbon bond migration forms a [2.2.1] bridged bicyclic core of a Lewis acid complex (i.e., Compound 13 in Reaction Scheme 3 above). Finally, loss of $BF_3$ reveals the isolated derivative product of Formula 19. Importantly, the stereospecific rearrangement mechanism allowed assignment of the relative stereochemistry of the cyclobutenes of Formula 17A from the unequivocal assignment of the bridged bicycle of Formula 19.

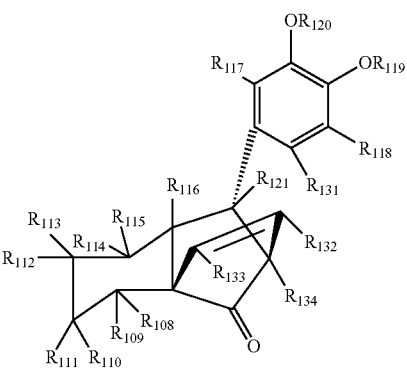

Formula 19

In the above method of making the compounds of Formula 19, replacing the $BF_3$ with $AlCl_3$ also promotes ring expansion of the aryl cyclobutene of Formula 17A, but does not result in the Cargill rearrangement product of Formula 19. Instead, using from 3 to 10 equivalents, for example 5 equivalents, of $AlCl_3$ in a solvent (e.g., trichloromethane) at a temperature of about 20 to about 30° C. yielded an enone represented by Formula 21 (discussed above and reproduced below). This enone arises from the intramolecular 1,6-addition of the electron-rich arene fragment of the compound represented by Formula 13 (described and depicted above) to the cycloheptadienone system. This suggests that the arene resides in close proximity to the tri-substituted olefin.

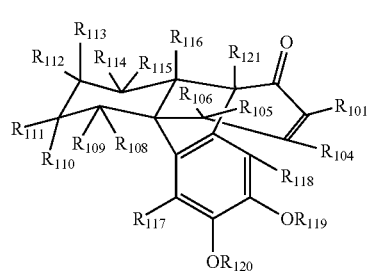

Formula 21

Although the above methods are described in connection with the synthesis of a single enantiomer of the desired products, those of ordinary skill in the art would readily recognize the corresponding methods needed to create the opposite enantiomer. Specifically, as discussed above, the same basic methods may be used to make the opposite enantiomers, except that the reactants used would be their opposite enantiomer. For example, to produce an end-product of the opposite enantiomer, the enantiomer of Formula 14 may be used in the methods instead of the enantiomer of Formula 13, etc. This applies to all enantiomers discussed above.

EXAMPLES

The below Examples are presented for illustrative purposes only, and do not limit the scope of the present invention.

Materials and Methods.

Unless otherwise stated, reactions were performed in flame-dried glassware under an argon or nitrogen atmosphere using dry, deoxygenated solvents. Reaction progress was monitored by thin-layer chromatography (TLC). THF was distilled over sodium/benzophenone or dried by passage through an activated alumina column under argon prior to use. Methanol was distilled over Mg(OMe)$_2$ prior to use. Other solvents were dried by passage through an activated alumina column under argon. Diisopropylamine and triethylamine were distilled over CaH$_2$ prior to use. Iodomethane was distilled prior to use. Purified water was obtained using a Barnstead NANOpure Infinity UV/UF system. Brine solutions are saturated aqueous solutions of sodium chloride. Phosphinooxazoline (PHOX) ligands were prepared by the methods described in Krout, et al., "Preparation of (S)-tert-ButylPHOX," Org. Synth., vol. 86, pgs. 181-193 (2009). All other reagents were purchased from Sigma-Aldrich, Acros Organics, Strem, or Alfa Aesar and used as received unless otherwise stated. Reaction temperatures were controlled by an IKAmag temperature modulator. Microwave-assisted reactions were performed in a Biotage Initiator 2.5 microwave reactor. Analytical LC/MS was performed on an Agilent 6140 single quadrupole LC/MS with an Agilent 1290 Infinity UHPLC system. Glove box manipulations were performed under a N$_2$ atmosphere. TLC was performed using E. Merck silica gel 60 F254 precoated glass plates (0.25 mm) and visualized by UV fluorescence quenching, p-anisaldehyde, or KMnO4 staining. ICN silica gel (particle size 0.032-0.0653 mm) was used for flash column chromatography. Automated flash column chromatography was performed on a Teledyne Isco CombiFlash Rf system. $^1$H NMR spectra were recorded on a Varian Mercury 300 MHz, Varian Inova 500 MHz, or Varian Inova 600 MHz spectrometer and are reported relative to residual CHCl$_3$ (δ 7.26 ppm) or C$_6$D$_6$ (δ 7.16 ppm). $^{13}$C NMR spectra are recorded on a Varian Mercury 300 MHz or Varian Inova 500 MHz spectrometer (at 75 MHz and 125 MHz respectively) and are reported relative to CDCl$_3$ (δ 77.2 ppm) or C$_6$D$_6$ (δ 128.4 ppm). Data for $^1$H NMR are reported as follows: chemical shift (δ ppm) (multiplicity, coupling constant (Hz), integration). Multiplicities are reported as follows: s=singlet, d=doublet, t=triplet, q=quartet, sext=sextet, dd=doublet of doublets, ddd=doublet of doublet of doublets, dddd=doublet of doublet of doublet of doublets, m=multiplet. Data for $^{13}$C are reported in terms of chemical shifts (δ ppm). IR spectra were obtained using a Perkin Elmer Paragon 1000 using thin films deposited on NaCl plates and reported in frequency of absorption (cm$^{-1}$). Optical rotations were measured with a Jasco P-2000 polarimeter operating on the sodium D-line (589 nm) using a 100 mm path-length cell and are reported as: $[\alpha]^T_D$, (concentration in g/100 mL, solvent, ee). Melting points were measured using a Thomas-Hoover capillary melting point apparatus and the reported values are uncorrected. Analytical chiral HPLC was performed with an Agilent 1100 Series HPLC utilizing a Chiralcel AD column (4.6 mm×25 cm) obtained from Daicel Chemical Industries Ltd. with visualization at 254 nm. Analytical chiral SFC was performed with a Mettler Toledo SFC supercritical CO$_2$ analytical chromatography system with a Chiralcel AD-H column (4.6 mm×25 cm) with visualization at 244 nm/235 nm. High-resolution mass spectra (HRMS) were obtained from the Caltech Mass Spectral Facility (EI+ or FAB+) or on a Agilent 6200 Series TOF with an Agilent G1978A Multimode source in electrospray ionization (ESI+), atmospheric pressure chemical ionization (APCI+), or mixed (MM: ESI-APCI+) ionization mode.

Experimental Procedures and Spectroscopic Data.

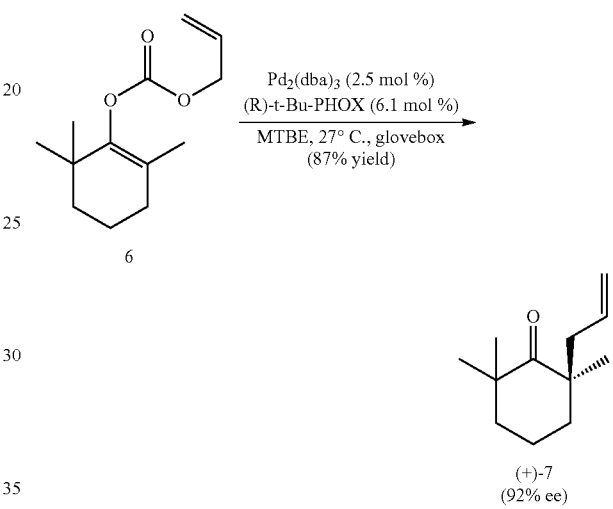

Allyl Ketone (+)-7.

In the glovebox, an oven dried recovery flask was charged with Pd$_2$(dba)$_3$ (25.8 mg, 0.0281 mmol), followed by (R)-t-Bu-PHOX (26.8 mg, 0.0691 mmol). Anhydrous t-butyl methyl ether (37 mL) was added and the solution stirred for 30 min. After this time, enol carbonate 6 (254.1 mg, 1.13 mmol) was added via pipette as a solution in t-butyl methyl ether (~2 mL). The flask was sealed with a yellow WW series Caplugs® and stirred at 27° C. for 15 h. The reaction was removed from the glovebox and vacuum filtered through silica gel. The majority of t-butyl methyl ether was removed by distillation under nitrogen and the remaining material purified by flash column chromatography on silica gel (2% Et$_2$O/pentane) providing allyl ketone (+)-7 (177.8 mg, 87% yield) as a colorless oil in 92% ee as determined by chiral HPLC of enone (+)-5 (vide infra). $[\alpha]^{25}_D$=+42.7° (c 1.005, CHCl$_3$), 92% ee. Other characterization data for this compound matched what has been previously reported.[2]

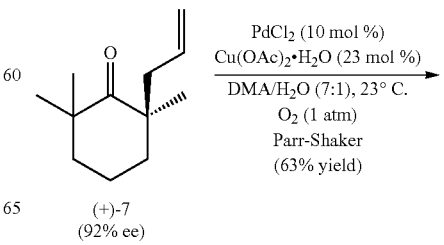

57

-continued

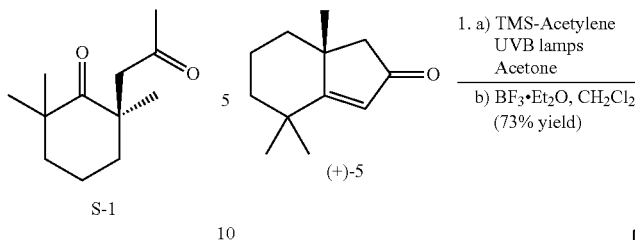

Diketone (+)-S-1.

A Parr flask was charged with PdCl$_2$ (7.0 mg, 0.0394 mmol) and Cu(OAc)$_2$.H$_2$O (38.6 mg, 0.229 mmol), followed by H$_2$O (0.25 mL). A solution of allyl ketone (+)-7 (152.1 mg, 0.843 mmol) in DMA (1.75 mL) was introduced. The reaction was cooled to −78° C., then evacuated/backfilled (vacuum/O$_2$) (3×). The reaction was warmed to 22° C. and placed on a Parr Shaker under 1 atm of O$_2$ for 25 h. At this time additional PdCl$_2$ (10.3 mg, 0.058 mmol) was added and the reaction restarted on the Parr Shaker under 1 atm of O$_2$. After 60 h the reaction was directly loaded onto a column of silica gel and purified by flash column chromatography (20:80 Et$_2$O:pentane eluent) giving diketone (−)-S-1 (105.5 mg, 63% yield) in 92% ee as determined by chiral HPLC of enone (+)-5 (vide infra). $[\alpha]^{25}_D=-72.9°$ (c 1.05, CHCl$_3$), 92% ee. Other characterization data for this compound matched what has been previously reported. See McFadden, et al., "The Catalytic Enantioselective, Protecting Group-Free Total Synthesis of (+)-Dichroanone," J. Am. Chem. Soc., vol. 128, pgs. 7738-7739 (2006), the entire content of which has already been incorporated herein by reference.

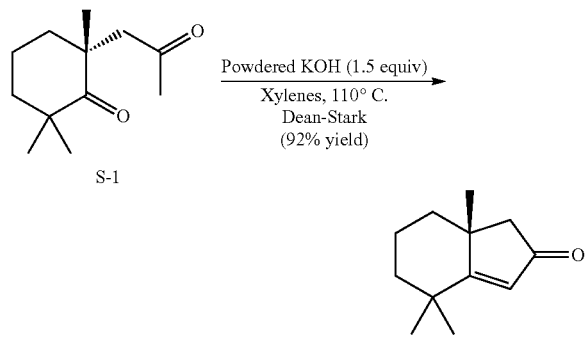

Enone (+)-5.

Diketone (−)-S-1 (105.5 mg, 0.537 mmol) was dissolved in xylenes under N$_2$ and charged to a round-bottom flask with an attached reflux condenser. Freshly powdered KOH (47.2 mg, 0.841 mmol) was added quickly all at once and the colorless solution was placed in a pre-heated oil bath and stirred at 110° C. for 11 h. After cooling, the reaction was directly loaded onto silica gel and purified by flash column chromatography (20:80 Et$_2$O:pentane→50:50 Et$_2$O:pentane eluent) yielding enone (+)-5 (87.8 mg, 92% yield) in 92% ee as determined by chiral HPLC. $[\alpha]^{25}_D=+99.9°$ (c 1.035, CHCl$_3$), 92% ee. Other characterization data for this compound matched what has been previously reported. See McFadden, et al., "The Catalytic Enantioselective, Protecting Group-Free Total Synthesis of (+)-Dichroanone," J. Am. Chem. Soc., vol. 128, pgs. 7738-7739 (2006), the entire content of which has already been incorporated herein by reference.

58

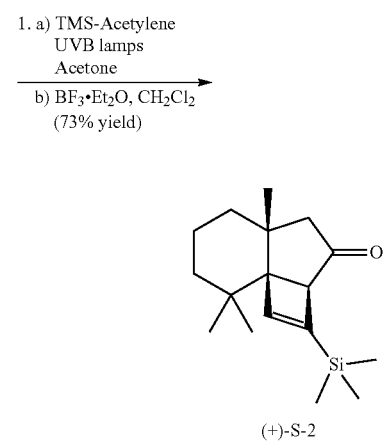

Silylcyclobutene (+)-S-2.

Enone (+)-5 (506.7 mg, 2.84 mmol) was distributed into five quartz test tubes and dissolved in anhydrous acetonitrile (5 mL each) and spectrophotometric grade acetone (1 mL each). To each test tube was added Trimethylsilyl acetylene (2.5 mL, 17.56 mmol; 0.5 mL each) and then capped with a yellow WW series Caplugs®. The test tubes were inverted (3×) to ensure adequate mixing of the reagents. At this time the reactions were placed in a Luzchem photoreactor and irradiated with ten UVB lamps (~313 nm) for a total of 22.5 h. The test tubes were removed from the photoreactor and the contents concentrated in vacuo. Due to the instability of one isomeric product the crude reaction mixture was immediately advanced to the next step.

The crude reaction mixture was dissolved in anhydrous CH$_2$Cl$_2$ and stirred while BF$_3$.OEt$_2$ (0.050 mL, 0.405 mmol) was added dropwise. The contents of the reaction were aged for 30 min and then treated with Celite® (5 g). The reaction was vacuum filtered, concentrated in vacuo, and purified by flash column chromatography on silica gel (2:98 EtOAc:hexane) providing silylcyclobutene (+)-S-2 (577.4 mg, 73% yield; two stages) as a white waxy solid. R$_f$=0.68 (20% EtOAc:hexanes), $^1$H NMR (CDCl$_3$, 500 MHz, 7.26 ppm for CHCl$_3$ in CDCl$_3$): δ=6.81 (d, J=1.4 Hz, 1H), 3.05 (m, 1H), 2.96 (d, J=16.2 Hz, 1H), 1.65-1.52 (m, 2H), 1.43-1.35, (m, 3H), 1.32-1.10 (m, 5H), 1.02 (s, 3H), 0.89 (s, 3H), 0.046 (s, 9H); $^{13}$C NMR (CDCl$_3$, 125 MHz, 77.2 ppm for CDCl$_3$): δ=216.6, 157.1, 153.3, 64.7, 59.2, 52.1, 38.7, 36.7, 36.3, 33.4, 28.1, 24.9, 22.0, 18.4, −2.1; IR (NaCl, cm$^{-1}$): v=2996, 2956, 2927, 2871, 2845, 1732, 1561, 1456, 1413, 1388, 1378, 1249, 1225, 1213, 1161, 962, 907, 840, 753; HRMS (MM: ESI-APCI+) m/z: C$_{17}$H$_{29}$OSi[M+H]$^+$: calc'd 277.1982. found 277.1989; $[\alpha]^{25}_D=+477.687$ (c=3.39, CHCl$_3$), 91% ee.

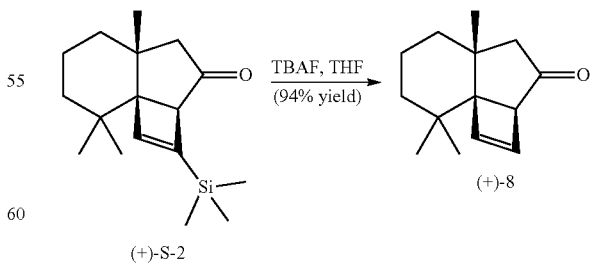

Cyclobutene (+)-8.

To a solution of silylcyclobutene (+)-S-2 (253.0 mg, 0.915 mmol) in anhydrous THF was added 1.0 M TBAF in THF (2 mL, 2.0 mmol) under a N$_2$ atmosphere. The colorless solution immediately turned reddish-brown. The reaction was stirred and heated to 40° C. in an oil bath. Following completion of the reaction, as monitored by TLC, it was concentrated in vacuo and loaded directly onto silica gel with $CH_2Cl_2$ for flash column chromatography (5:95 EtOAc:hexanes) to afford cyclobutene (+)-8 (176.6 mg, 94% yield) as a white waxy volatile solid. $R_f$=0.39 (10% EtOAc/Hex), sublimation point, sp: <23° C. (3 mmHg); $^1H$ NMR ($CDCl_3$, 500 MHz, 7.26 ppm for $CHCl_3$ in $CDCl_3$): δ=6.37 (m, 1H), 6.32 (m, 1H), 3.06-3.02 (m, 2H), 1.69-1.55 (m, 2H), 1.47-1.36 (m, 3H), 1.30 (m, 1H), 1.21-1.12 (m, 4H), 1.05 (s, 3H), 0.94 (s, 3H); $^{13}C$ NMR ($CDCl_3$, 125 MHz, 77.2 ppm for $CDCl_3$): δ=216.2, 143.0, 137.8, 65.2, 58.4, 51.9, 38.8, 37.1, 36.1, 33.5, 28.2, 25.1, 22.1, 18.4; IR (NaCl, $cm^{-1}$): v=3046, 2957, 2924, 2870, 2844, 1733, 1456, 1414, 1388, 1378, 1364, 1212, 1161, 725; HRMS (MM: ESI-APCI+) m/z: $C_{14}H_{21}O[M+H]^+$: calc'd 205.1587. found 205.1591; $[α]^{25}_D$=+642.438° (c=1.065, $CHCl_3$), 91% ee.

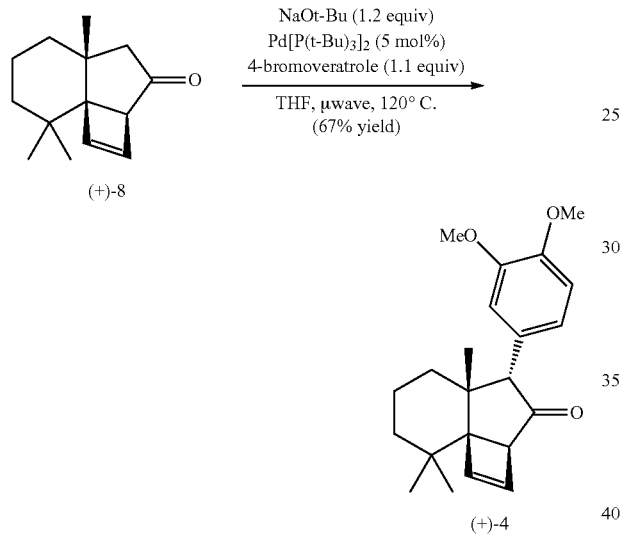

Arylcyclobutene (+)-4.

In the glovebox, a 5 mL oven-dried microwave vial was charged with $Pd[P(t-Bu)_3]_2$ (14.3 mg, 0.02798 mmol, 5 mol %) and NaOt-Bu (65.6 mg, 0.6826 mmol). A stir bar was added to the vial before it was sealed and removed from the glovebox. A solution of cyclobutene (+)-8 (110.0 mg, 0.5388 mmol) in anhydrous THF was added to the vial under $N_2$, followed by 4-bromoveratrole (0.085 mL, 0.5908 mmol). The reaction was placed in the microwave reactor and heated to 120° C. for a total of 7.5 h. The reaction was quenched with sat. aq $NH_4Cl$ (0.50 mL) and treated with activated charcoal (0.022 mg) and Celite® (0.310 mg). The heterogeneous mixture was stirred overnight and then vacuum filtered. The residue was purified by flash column chromatography on silica gel (5:95→10:90 EtOAc:hexanes) to provide aryl cyclobutene (+)-4 (124.0 mg, 67% yield) as a white amorphous solid. $R_f$=0.28 (20:80 EtOAc:hexane); $^1H$ NMR (500 MHz, $C_6D_6$): δ 6.80 (d, J=2.2 Hz, 1H), 6.74 (dd, J=8.3 Hz, 2.2 Hz, 1H), 6.68 (d, J=8.3 Hz, 1H), 6.15 (app. dd, J=2.9 Hz, 0.9 Hz, 1H), 6.05 (app. dd, J=2.9 Hz, 1.5 Hz, 1H), 4.35 (s, 1H), 3.54 (s, 3H), 3.46 (s, 3H), 3.12 (app. dd, J=1.5 Hz, 0.9 Hz, 1H), 1.37-1.18 (m, 3H), 1.09 (app. ddd, J=13.7 Hz, 3.7 Hz, 3.4 Hz, 1H), 1.08-1.02, (m, 1H), 1.07 (app. ddd, J=12.9 Hz, 3.7 Hz, 3.2 Hz, 1H), 1.02 (s, 3H), 0.93 (s, 3H), 0.89 (s, 3H); 13C NMR (125 MHz, $C_6D_6$): δ 212.8, 149.93, 149.92, 142.6, 140.4, 126.9, 125.1, 117.1, 112.3, 63.1, 60.7, 57.1, 56.3, 56.0, 40.5, 39.3, 34.0, 33.6, 28.7, 25.9, 20.7, 18.6; IR (NaCl, $cm^{-1}$): v=2930, 2871, 2842, 1732, 1608, 1588, 1517, 1464, 1253, 1146, 1030, 739; HRMS ($EI^+$) m/z: $C_{22}H_{28}O_3[M]^{+\bullet}$: calc'd 340.2039. found 340.2040; $[α]^{25}_D$=+512.59° (c 1.015, $CHCl_3$), 91% ee.

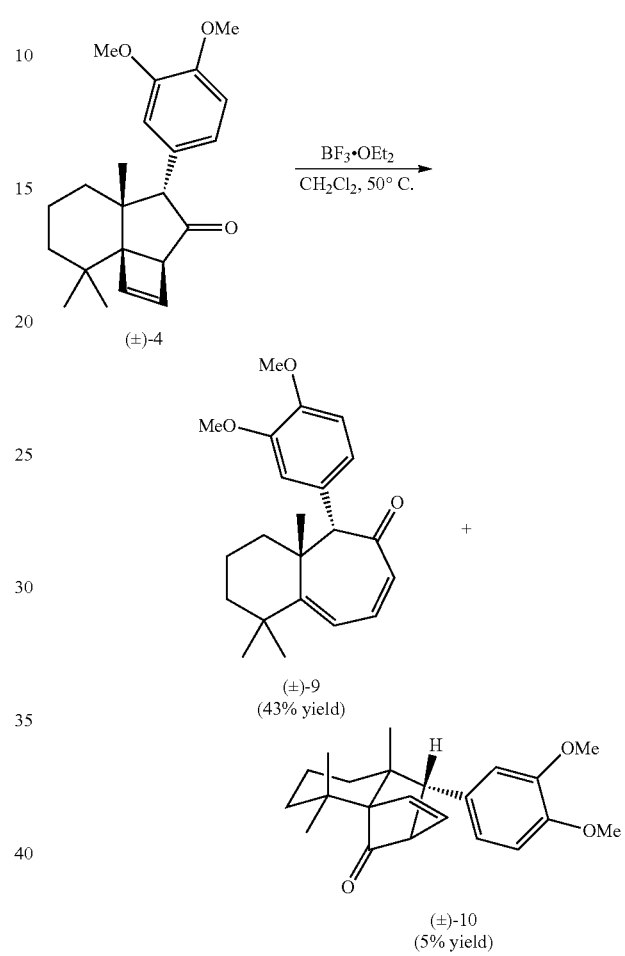

Aryl Cycloheptadienone (±)-9 and Cargill Rearrangement Adduct (±)-10.

A Schlenk flask was charged with a solution of aryl cyclobutene (±)-4 (563 mg, 1.65 mmol) and $CH_2Cl_2$ (52 mL). $BF_3 \cdot OEt_2$ (1.05 mL, 8.27 mmol) was then introduced. The vessel was sealed and heated with stirring to 50° C. behind a blast shield for 20 h. The reaction was cooled to 23° C. and added slowly to a suspension of brine (25 mL), sat. aq $NaHCO_3$ (25 mL), and $CH_2Cl_2$ (25 mL). After addition was complete, the reaction was stirred vigorously for 5 min. The organic layer was collected, and the aqueous layer was extracted with $CH_2Cl_2$ (2×30 mL). All organic layers were combined, dried ($Na_2SO_4$), filtered, and concentrated. The residue was purified by flash column chromatography on silica gel (hexane→20:80 EtOAc:hexane→30:70 EtOAc: hexane→40:60 EtOAc:hexane eluent), affording aryl cycloheptadienone (±)-9 (242 mg, 43% yield) as a yellow oil. $R_f$ 0.61 (50:50 EtOAc/hexane); $^1H$ NMR (500 MHz, $C_6D_6$): δ 7.01 (app. d, J=2.0 Hz, 1H), 6.95 (app. dd, J=8.3 Hz, 2.0 Hz, 1H), 6.53 (d, J=8.3 Hz, 1H), 6.17 (d, J=6.8 Hz, 1H), 6.16 (d, J=2.0 Hz, 1H), 5.91 (dd, J=6.8 Hz, 2.0 Hz, 1H), 3.55 (s, 1H), 3.48 (s, 3H), 3.38 (s, 3H), 1.82 (app. td, $J_t$=13.2 Hz, $J_d$=5.1 Hz, 1H), 1.53-1.43 (m, 1H), 1.29-1.16 (m, 2H), 1.24 (s, 3H), 1.13-1.00 (m, 2H), 1.00 (s, 3H), 0.93 (s, 3H); $^{13}$C NMR (125 MHz, C$_6$D$_6$): δ 198.5, 166.8, 150.1, 150.0, 137.0, 129.8, 129.5, 123.1, 121.0, 114.8, 112.3, 70.6, 56.1, 55.9, 41.0, 38.6, 38.3, 36.8, 33.6, 31.7, 25.2, 17.9; IR (NaCl, cm$^{-1}$): v=2924, 1645, 1573, 1516, 1463, 1419, 1264, 1236, 1148, 1028; HRMS (EI$^+$) m/z: C$_{22}$H$_{28}$O$_3$ [M]$^{+\bullet}$: calc'd 340.2039. found 340.2038.

In addition to (±)-9, several fractions containing a second compound in semipure form were collected from the flash column above. These fractions were combined and concentrated. The residue was purified by flash column chromatography on silica gel (50:50 CH$_2$Cl$_2$:PhH→10:50:50 EtOAc: CH$_2$Cl$_2$:PhH), affording pure Cargill rearrangement adduct (±)-10 (28.1 mg, 5.0% yield) as colorless crystals. One of these crystals was suitable for X-Ray analysis, allowing for determination of the relative stereochemistry of the compound. R$_f$ 0.74 (50:50 EtOAc/hexane); mp 116-118° C. (C$_6$D$_6$); $^1$H NMR (500 MHz, C$_6$D$_6$); δ 6.79 (app. d, J=8.3 Hz, 1H), 6.78 (app. s, 1H), 6.57 (app. d, J=8.3 Hz, 1H), 6.32 (app. dd, J=7.1 Hz, 3.9 Hz, 1H), 6.20 (app. dd, J=7.1 Hz, 1.2 Hz, 1H), 3.54 (s, 3H), 3.44 (s, 3H), 2.83 (app. dd, J=3.9 Hz, 0.7 Hz, 1H), 2.23 (s, 1H), 2.04 (app. td, J$_t$=13.4 Hz, J$_d$=3.9 Hz, 1H), 1.47 (app. qt, J$_q$=13.7 Hz, J$_t$=3.2 Hz, 1H), 1.35 (app. d, J=14.2 Hz, 1H), 1.32-1.13 (m, 2H), 1.29 (s, 3H), 1.05 (s, 3H), 1.00 (s, 3H), 0.74 (app. d, J=13.9 Hz, 1H); $^{13}$C NMR (125 MHz, C$_6$D$_6$): δ 206.5, 150.2, 149.4, 134.6, 134.4, 134.1, 121.0, 113.2, 112.5, 64.0, 56.1, 56.0, 53.4, 40.2, 37.1, 34.3, 32.5, 32.4, 28.1, 26.9, 26.6, 19.6; IR (NaCl, cm$^{-1}$): v=2995, 2934, 2867, 2834, 1772, 1518, 1464, 1267, 1254, 1241, 1147, 1030, 750; HRMS (EI$^+$) m/z: C$_{22}$H$_{28}$O$_3$[M]$^{+\bullet}$: calc'd 340.2039. found 340.2034.

(2×20 mL). All organic layers were combined, dried (Na$_2$SO$_4$), filtered, and concentrated to ~500 μL total volume. The brown oil was purified by preparative TLC (20:80 EtOAc:hexane eluent), affording the Friedel-Crafts adduct (±)-14 (8.3 mg, 17% yield) as a yellow powder. R$_f$ 0.24 (20:80 EtOAc/hexane); mp 152-155° C. (CHCl$_3$); $^1$H NMR (300 MHz, CDCl$_3$) δ 7.09 (s, 1H), 6.64 (s, 1H), 6.04 (app. ddd, J=12.6 Hz, 5.5 Hz, 3.6 Hz, 1H), 5.66 (app. dd, broad, J=12.6 Hz, 1.9 Hz, 1H), 3.84 (s, 3H), 3.81 (s, 3H), 3.33 (app. d, broad, J=1.6 Hz, 1H), 2.84 (app. d, broad, J=1.9 Hz, 1H), 2.84 (app. dd, J=9.0 Hz, 1.6 Hz, 1H), 1.72-1.58 (m, 1H), 1.54-1.26 (m, 4H), 1.43 (s, 3H), 1.26 (s, 3H), 1.24-1.00 (m, 1H), 1.19 (s, 3H); $^{13}$C NMR (75 MHz, CDCl$_3$): δ 148.8, 148.4, 142.9, 139.5 135.5, 128.7, 110.2, 107.6, 73.1, 57.5, 56.3, 55.9, 46.4, 40.8, 39.9, 38.9, 37.5, 29.6, 26.9, 20.7, 18.4; IR (NaCl, cm$^{-1}$): v=2932, 1659, 1605, 1504, 1464, 1402, 1295, 1206, 1096, 1036, 914, 857, 755; HRMS (EI$^+$) m/z: C$_{22}$H$_{28}$O$_3$[M]$^{+\bullet}$: calc'd 340.2039. found 340.2039. $^1$H-nOesy-1D spectra were obtained for (±)-14 (300 MHz, CDCl$_3$); the results are shown below:

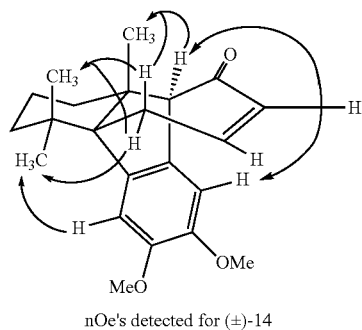

nOe's detected for (±)-14

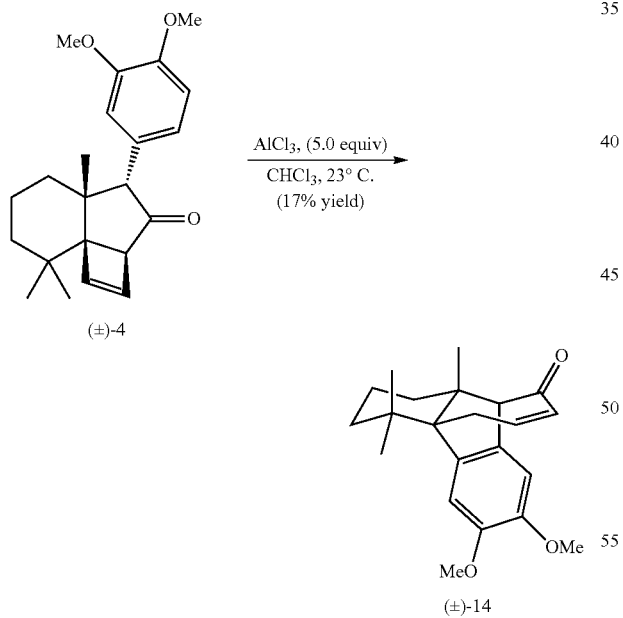

Friedel-Crafts Adduct (±)-14.

A solution of aryl cyclobutene (±)-4 (50 mg, 0.147 mmol, 1.0 equiv) in CHCl$_3$ (15.0 mL) was treated with AlCl$_3$ (98.0 mg, 0.735 mmol, 5.0 equiv, weighed in the glovebox). As the reaction stirred for 48 h, it went from peach-colored to maroon. After the reaction was complete, it was added dropwise to a solution of brine (20 mL) and sat. aq NaHCO$_3$ (20 mL) at 23° C. The suspension was then extracted with CHCl$_3$

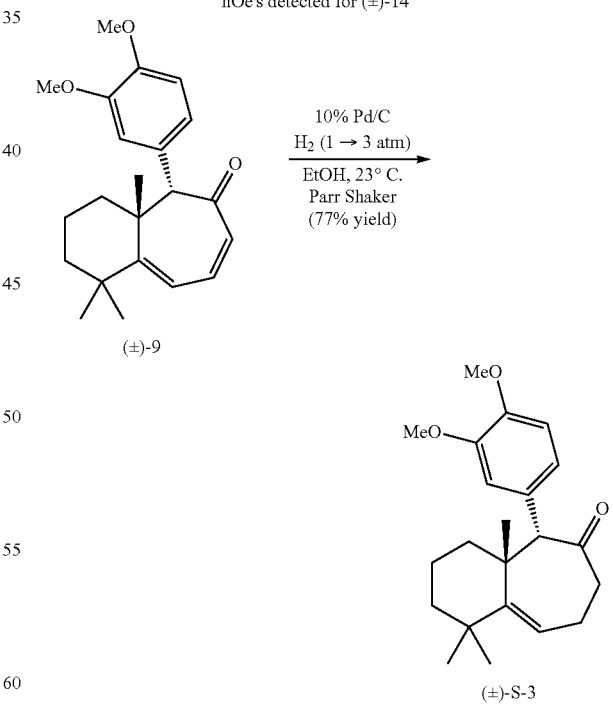

γ,δ-Unsaturated Aryl Cycloheptanone (±)-S-3.

A Parr flask was charged with 10% w/w Pd/C (38 mg, 35.3 mol, 5 mol %), followed by a solution of aryl cycloheptadienone (±)-9 (240 mg, 0.705 mmol) in absolute EtOH (40 mL). The reaction was placed under H$_2$ (1 atm) at 23° C. on a Parr shaker for 40 h. At this time, more 10% w/w Pd/C (114 mg, 0.106 mmol, 15 mol %) was carefully added. The reaction was continued under H₂ (now 3 atm) for 20 h. Once the reaction was complete, it was filtered through celite over glass frits with the aide of EtOAc. The filtrate was concentrated and purified by flash chromatography on silica gel (hexane→20:80 EtOAc:hexane eluent), giving γ,δ-unsaturated aryl cycloheptanone (±)-S-3 (188 mg, 77% yield) as a colorless oil. $R_f$ 0.31 (20:80 EtOAc/hexane); ¹H NMR (300 MHz, C₆D₆): δ 7.17 (app. d, J=2.1 Hz, 1H), 7.09 (app. dd, J=8.2 Hz, 2.1 Hz, 1H), 6.59 (app. d, J=8.2 Hz, 1H), 5.77 (dd, J=8.2 Hz, 5.2 Hz, 1H), 3.85 (s, 1H), 3.49 (s, 3H), 3.43 (s, 3H), 2.60 (app. td, $J_t$=13.8 Hz, $J_d$=4.7 Hz, 1H), 2.30-1.86 (m, 5H), 1.60-1.42 (m, 1H), 1.36-1.20 (m, 1H), 1.27 (s, 3H), 1.16 (s, 3H0, 1.01 (s, 3H), 0.98-0.68 (m, 1H); ¹³C NMR (75 MHz, C₆D₆): δ 210.0, 153.5, 150.1, 149.7, 130.5, 123.6, 123.5, 115.3, 112.3, 71.8, 56.2, 55.9, 42.0, 41.0, 40.2, 37.8 (2C), 33.8, 33.7, 28.4, 23.7, 18.6; IR (NaCl, cm⁻¹): v=2933, 1695, 1603, 1588, 1515, 1464, 1379, 1252, 1146, 1029, 756; HRMS (EI⁺) m/z: C₂₂H₃₀O₃[M]⁺·: calc'd 342.2195. found 342.2183.

3H); ¹³C NMR (75 MHz, CDCl₃): δ 214.8, 148.7, 147.5, 142.7, 140.2, 125.0, 118.2, 115.9, 115.4, 62.9, 58.6, 56.3, 56.21, 56.18, 42.0, 39.0, 33.8, 33.5, 28.4, 25.6, 20.7, 17.9; IR (NaCl, cm⁻¹): v=2931, 2870, 2844, 1732, 1603, 1571, 1508, 1464, 1379, 1258, 1211, 1166, 1032, 914, 845, 735; HRMS (FAB⁺) m/z: C₂₂H₂₇O₃⁸¹Br[M+H]⁺: calc'd 420.1123. found 420.1119; [α]²⁵_D=+519.57° (c 2.16, CHCl₃), >99% ee.

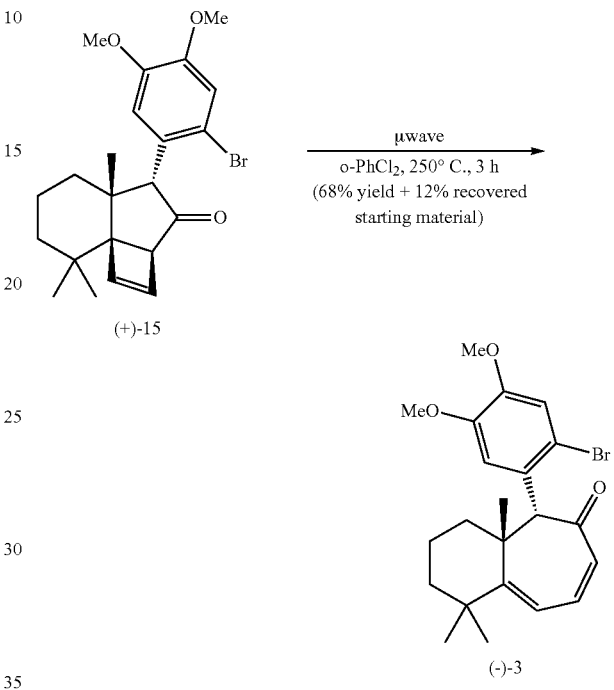

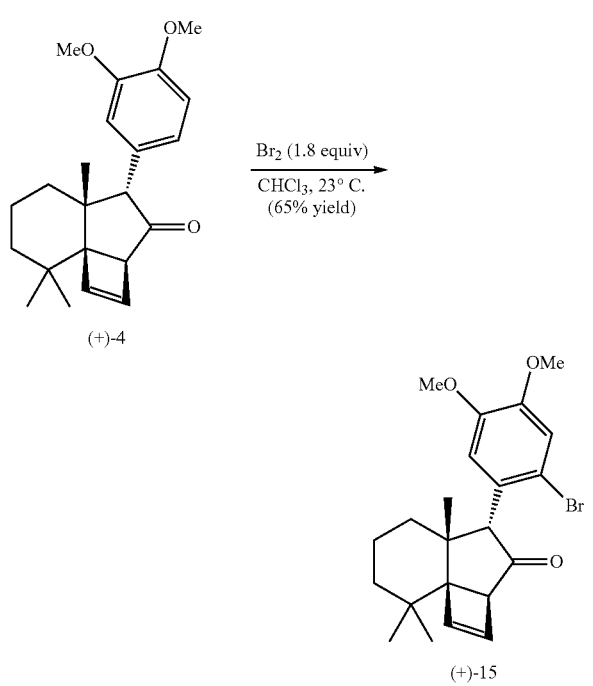

Bromoaryl dienone (−)-3.

A round bottom flask was charged with bromoaryl cyclobutene (+)-15 (214.5 mg, 0.512 mmol) and dissolved in o-dichlorobenzene (o-PhCl₂) (15 mL) with the aide of mild heating from a heat gun. The clear and colorless solution was distributed between three 20 mL microwave vials. The round bottom flask was rinsed with o-PhCl₂ (15 mL×2, 9 mL×1) and again distributed between the three microwave vials (total=18 mL each). The solutions were sealed, placed under Ar, and degassed by the method of freeze-pump-thaw (3×). At this time, the microwave vials were individually irradiated (3 h) in a microwave reactor at 250° C. Following irradiation the clear yellow-orange solutions were combined and loaded directly onto silica gel for purification by flash column chromatography (10:90→20:80→30:70 EtOAc:hexanes) yielding bromoaryl dienone (−)-3 (147.0 mg, 68% yield) as a yellow solid, in addition to recovered bromoaryl cyclobutene (+)-15 (26.0 mg, 12% yield) as a white solid. $R_f$=0.28 (20:80 EtOAc/hexane); mp 146-147° C. (EtOAc/hexane)(racemate), mp 144-147° C. (EtOAc/hexane)(95% ee); ¹H NMR (300 MHz, CDCl₃): δ 7.21 (s, 1H), 7.03 (s, 1H), 6.70 (dd, J=12.4 Hz, 8.8 Hz, 1H), 6.30 (d, J=8.8 Hz, 1H), 6.08 (d, J=12.4 Hz, 1H), 4.16 (s, 1H), 3.82 (s, 3H), 3.72 (s, 3H), 1.75-1.33 (m, 5H), 1.37 (s, 3H), 1.21 (s, 3H), 1.22-1.04 (m, 1H), 1.05 (s, 3H); ¹³C NMR (75 MHz, CDCl₃): δ 198.7, 168.4, 148.4, 148.0, 137.6, 129.5, 128.1, 120.4, 118.0, 115.8, 112.4, 66.3, 56.1, 55.8, 42.8, 38.4, 37.9, 35.4, 33.5, 31.5, 25.3, 17.0; IR (NaCl, cm⁻¹): v=2934, 1644, 1572, 1509, 1463, 1440, 1377, 1267, 1248, 1230, 1205, 1159, 1030, 837; HRMS (EI⁺) m/z C₂₂H₂₇BrO₃[M]⁺°: calc'd 418.1144. found 418.1158; [α]²⁴_D=−437.31° (c 0.985, CHCl₃), 95% ee.

Bromoaryl cyclobutene (+)-15.

To a solution of aryl cyclobutene (+)-4 (268.0 mg, 0.787 mmol) in CHCl₃ was added a 0.1 g/mL CHCl₃ solution of Br₂ (1.2 mL, 0.795 mmol). After 5 min additional Br₂ (0.990 mL, 0.655 mmol) was added portion-wise. The reaction was quenched with sat. aq NaHCO₃ (10 mL) and 5% aq Na₂S₂O₃ (10 mL). This mixture was extracted with CH₂Cl₂ (3×25 mL), washed with Brine, dried (MgSO₄), vacuum filtered, and concentrated in vacuo. The crude product was recrystallized from EtOAc yielding bromoaryl cyclobutene (+)-15 (214.5 mg, 65% yield) as colorless crystals in >99% ee as determined by chiral SFC. $R_f$=0.39 (20:80 EtOAc/hexane); mp 215-217° C. (EtOAc/hexane)(racemate), mp 240-242° C. (95% ee)³; NMR (300 MHz, CDCl₃): δ 7.02 (s, 1H), 6.65 (s, 1H), 6.57 (app. dd, J=2.7 Hz, 0.8 Hz, 1H), 6.52 (app. dd, J=2.7 Hz, 1.6 Hz, 1H), 5.21 (s, 1H), 3.84 (app. s, 6H), 3.13 (app. s, 1H), 1.60-1.40 (m, 3H), 1.34 (app. dd, J=12.9 Hz, 3.8 Hz, 1H), 1.28-1.04 (m, 2H), 1.19 (s, 3H), 1.11 (s, 3H), 1.00 (s,

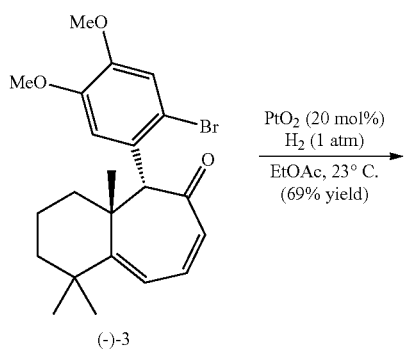

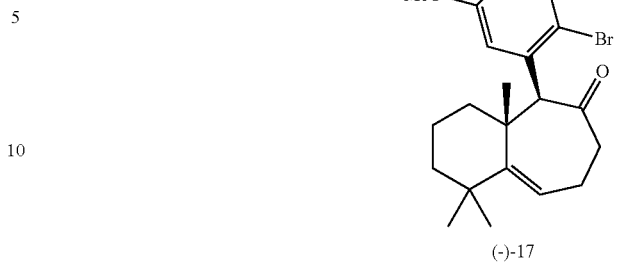

Bromoaryl⁻-γ,δ⁻-Unsaturated Cycloheptanone (+)-16.

A round-bottom flask containing bromoaryl dienone (−)-3 (400 mg, 0.952 mmol) in EtOAc (ACS grade, 50 mL) was degassed with argon for 5 min. Then, PtO$_2$ (43.2 mg, 0.190 mmol, 20 mol %) was carefully added. The reaction was cooled to −78° C., then evacuated/backfilled (vacuum/H$_2$ (1 atm)) (3×). With vigorous stirring, the reaction was warmed to 23° C. under H$_2$ (1 atm). After 30 min, the reaction was concentrated, and the residue was taken up in PhH. It was purified by flash chromatography on silica gel (10:90 EtOAc:hexane eluent), giving bromoaryl⁻-γδ⁻-unsaturated cycloheptanone (+)-16 (277 mg, 69% yield) as a white solid. R$_f$=0.41 (20:80 EtOAc/hexane); mp 114-116° C. (EtOAc/hexane)(racemate), mp 121-123° C. (EtOAc/hexane)(95% ee); $^1$H NMR (300 MHz, CDCl$_3$): δ 7.58 (s, 1H), 7.02 (s, 1H), 6.00 (dd, J=9.9 Hz, 4.4 Hz, 1H), 4.68 (s, 1H), 3.87 (s, 3H), 3.85 (s, 3H), 2.71-2.49 (m, 2H), 2.43-2.32 (m, 2H), 1.79-1.57 (m, 2H), 1.51-1.39 (m, 2H), 1.36-1.24 (m, 2H), 1.28 (s, 3H), 1.19 (s, 3H), 1.17 (s, 3H); $^{13}$C NMR (75 MHz, CDCl$_3$): δ 210.0, 153.8, 148.6, 147.8, 128.2, 122.7, 118.4, 115.6, 115.0, 66.0, 56.7, 56.2, 43.9, 41.5, 39.7, 37.8, 36.4, 33.7, 33.3, 27.5, 23.4, 17.9; IR (NaCl, cm$^{-1}$): ν=2936, 2845, 1716, 1699, 1600, 1567, 1506, 1463, 1440, 1374, 1254, 1212, 1159, 1030, 732; HRMS (FAB$^+$) m/z: C$_{22}$H$_{29}$BrO$_3$[M]$^{+o}$: calc'd 420.1300. found 420.1303; [α]$^{25}_D$=+162.47° (c 1.250, CHCl$_3$), 95% ee.

β-Bromoaryl Ketone (−)-17.

In a glovebox[4], a 20 mL oven-dried scintillation vial was charged with a solution of bromoaryl⁻-γ,δ⁻-unsaturated cycloheptanone (+)-16 (138.1 mg, 0.327 mmol) in MeOH (1 mL) and ~1M NaOMe (5 mL, 5 mmol) in MeOH. The reaction mixture was heated to 65° C. in the glovebox with stirring for 86 h. The reaction was removed from the glovebox and quenched with AcOH (0.30 mL) under vigorous stirring. The mixture was diluted with H$_2$O (3.0 mL) and the volatiles concentrated in vacuo. Brine (3.0 mL) was added and the aqueous phase extracted with EtOAc (4×3 mL). The organic layers were combined, dried (MgSO$_4$), vacuum filtered, and concentrated in vacuo. The residue was purified by HPLC (Zorbax Rx-Sil, 5 μm, 9.4×250 mm, 8:92 EtOAc:hexanes, 7 mL/min, monitored at 254 nm) affording bromoaryl⁻-γ,δ⁻-unsaturated cycloheptanone (+)-16 (73.4 mg, 53% yield) as a white solid and β-bromoaryl ketone (−)-17 (61.6 mg, 44% yield) as a colorless oil. Retention times: bromoaryl⁻-γ,δ-⁻unsaturated cycloheptanone (+)-16 7.5 min, δ-bromoaryl ketone (−)-17 8.8 min. This procedure was repeated twice more with the recovered bromoaryl⁻-γ,δ⁻-unsaturated cycloheptanone (+)-16 to yield δ-bromoaryl ketone (−)-17 (109.0 mg, 78% yield after three cycles of equilibration) as a colorless oil. R$_f$=0.33 (20:80 EtOAc:hexanes); $^1$H NMR (CDCl$_3$, 300 MHz, 7.26 ppm for CHCl$_3$ in CDCl$_3$): δ=7.20 (s, 1H), 6.99 (s, 1H), 5.97 (dd, J$_1$=3.4 Hz, J$_2$=8.5 Hz, 1H), 5.28 (s, 1H), 3.90 (s, 3H), 3.84 (s, 3H), 2.77 (m, 1H), 2.66-2.51 (m, 2H), 2.33 (m, 1H), 1.67-1.19 (m, 11H), 1.15 (s, 3H), 0.92 (m, 1H); $^{13}$C NMR (CDCl$_3$, 75 MHz, 77.2 ppm for CDCl$_3$): δ=211.1, 155.7, 148.4, 147.5, 128.8, 121.9, 117.4, 115.3, 114.9, 62.3, 56.2, 56.1, 43.5, 43.1, 39.7, 38.2, 37.7, 33.9, 32.2, 24.8, 24.6, 18.2; IR (NaCl, cm$^{-1}$): ν=2933, 1706, 1602, 1570, 1506, 1466, 1439, 1375, 1308, 1266, 1209, 1160, 1029; HRMS (MM: ESI-APCI+) m/z: C$_{22}$H$_{30}$O$_3$Br[M+H]$^+$: calc'd 421.1373. found 421.1356; [α]$^{25}_D$=−212.15° (c=0.74, CHCl$_3$), >99% ee.

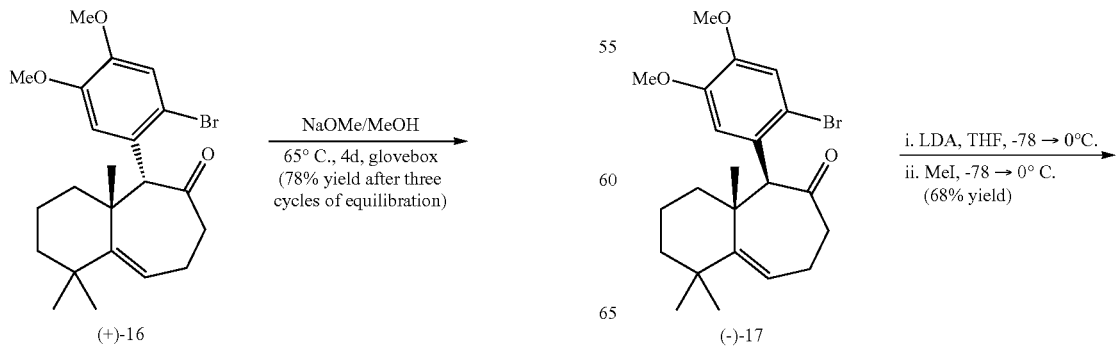

-continued

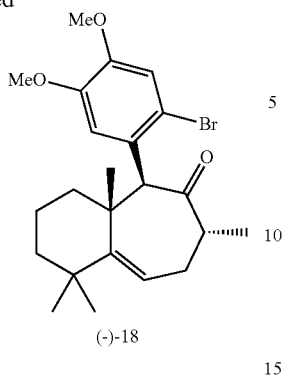

(−)-18

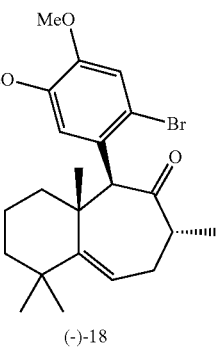

(−)-18

DIBAl
PhMe, 23° C.
(91% yield) →

Bromoaryl Methyl Ketone (−)-18.

To a solution of freshly distilled i-Pr$_2$NH (0.025 mL, 0.1768 mmol) in anhydrous THF (0.20 mL) cooled to −78° C. was added 2.3 M n-BuLi (0.062 mL, 0.1439 mmol) dropwise via syringe. The contents were stirred for 30 min at −78° C. before addition of β-bromoaryl ketone (−)-17 (57.8 mg, 0.1371 mmol) as a solution in anhydrous THF (1 mL). The pear-shaped flask containing β-bromoaryl ketone (−)-17 was rinsed with THF (0.20 mL) and added to the reaction mixture at −78° C. The stirred solution was aged for 30 min at −78° C. followed by 30 min in an ice-water bath. The reaction mixture was cooled to −78° C. and MeI (0.025 mL, 0.4015 mmol) was added dropwise. The reaction stirred for 15 min at −78° C., followed by 15 min in an ice-water bath. The reaction was allowed to warm to 23° C. and additional MeI (0.050 mL, 0.8030 mmol) was added. Stirring continued for 30 min before quenching with H$_2$O (5 drops). The volatiles were removed in vacuo and the residue dissolved in EtOAc and diluted with Brine. The organic layer was collected and the aqueous layer extracted with EtOAc (3×2 mL). All organic layers were combined, dried (Na$_2$SO$_4$), vacuum filtered, and concentrated in vacuo. The residue was purified by HPLC (Zorbax Rx-Sil, □m, 9.4×250 mm, 8:92 EtOAc:hexanes, 7 mL/min, monitored at 254 nm) affording bromoaryl methyl ketone (−)-18 (40.6 mg, 68% yield) as a colorless oil and β-bromoaryl ketone (−)-17 (10.6 mg, 18% yield) as a colorless oil. Retention times: bromoaryl methyl ketone (−)-18 5.4 min, β-bromoaryl ketone (−)-17 7.7 min. $R_f$=0.45 (20:80 EtOAc:hexanes); $^1$H NMR (CDCl$_3$, 300 MHz, 7.26 ppm for CHCl$_3$ in CDCl$_3$): δ=7.22 (s, 1H), 6.99 (s, 1H), 5.93, (dd, J$_1$=2.4 Hz, J$_2$=8.7 Hz, 1H), 5.35, (s, 1H), 3.91 (s, 3H), 3.84 (s, 3H), 2.79-2.48 (m, 2H), 2.29 (m, 1H), 1.72-1.35 (m, 4H), 1.33 (s, 3H), 1.26 (m, 1H), 1.19 (s, 3H), 1.17-1.10 (m, 6H), 0.96 (m, 1H); $^{13}$C NMR (CDCl$_3$, 75 MHz, 77.2 ppm for CDCl$_3$): δ=213.3, 155.6, 148.5, 147.7, 129.2, 121.4, 117.5, 115.5, 115.0, 61.3, 56.3, 56.2, 47.2, 43.4, 40.0, 38.2, 38.1, 34.0, 33.5, 32.0, 24.7, 18.4, 17.7; IR (NaCl, cm$^1$): ν=2932, 2868, 2843, 1706, 1602, 1503, 1462, 1441, 1377, 1308, 1262, 1207, 1162, 1032, 845, 795, 734; HRMS (MM: ESI-APCI+) m/z: C$_{23}$H$_{32}$O$_3$Br[M+H]$^+$: calc'd 435.1529. found 435.1526; $[\alpha]^{25}_D$=−190.14° (c=0.815, CHCl$_3$), >99% ee.

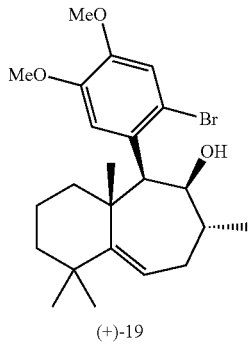

(+)-19

Aryl alcohol (+)-19.

To a solution of bromoaryl methyl ketone (−)-18 (40.6 mg, 0.0932 mmol) in anhydrous PhMe was added a freshly prepared 1M solution of DIBAL (0.380 mL, 0.380 mmol) in PhMe at 21° C. dropwise. The reaction aged for 20 min before it was quenched with sat. Na$_2$SO$_4$:Celite® (2:1) and stirred for an additional 30 min. The heterogeneous mixture was filtered and concentrated in vacuo. The residue was purified by HPLC (Zorbax Rx-Sil, 5 μm, 9.4×250 mm, 25:75 EtOAc:hexanes, 7 mL/min, monitored at 254 nm) providing aryl alcohol (+)-19 (37.3 mg, 91% yield) as a colorless oil. $R_f$=0.28 (20:80 EtOAc:hexanes); $^1$H NMR (CDCl$_3$, 500 MHz, 7.26 ppm for CHCl$_3$ in CDCl$_3$): δ=7.36 (s, 1H), 7.03 (s, 1H), 5.76 (dd, J$_1$=2.9 Hz, J$_2$=8.7 Hz, 1H), 3.95 (d, J=3.5 Hz, 1H), 3.86 (s, 3H), 3.85 (s, 3H), 3.41 (ddd, J$_1$=3.9 Hz, J$_2$=4.6 Hz, J$_3$=8.7 Hz, 1H), 2.32-2.06 (m, 3H), 1.72 (d, J=4.9 Hz, 1H), 1.69 (s, 3H), 1.68-1.60 (m, 1H), 1.44 (m, 1H), 1.37-1.19 (m, 3H), 1.14 (s, 3H), 1.11 (s, 3H), 1.05 (d, J=6.4 Hz, 3H), 0.92 (ddd, J$_1$=4.5 Hz, J$_2$=13.0 Hz, J$_3$=13.0 Hz, 1H); $^{13}$C NMR (CDCl$_3$, 125 MHz, 77.2 ppm for CDCl$_3$): δ=156.1, 147.9, 147.6, 134.5, 122.2, 116.9, 115.5, 114.5, 81.6, 56.2, 56.2, 54.6, 42.9, 40.0, 39.9, 39.8, 37.9, 34.0, 33.8, 32.4, 24.6, 20.7, 18.0; IR (NaCl, cm$^{-1}$): ν=3543, 2953, 2928, 2868, 2839, 1602, 1570, 1503, 1464, 1439, 1385, 1357, 1293, 1261, 1246, 1207, 1157, 1034, 757; HRMS (EI+) m/z: C$_{23}$H$_{33}$O$_3$Br[M]$^{-\cdot}$: calc'd 436.1613. found 436.1600; $[\alpha]^{25}_D$=+82.61° (c=0.145, CHCl$_3$), >99% ee.

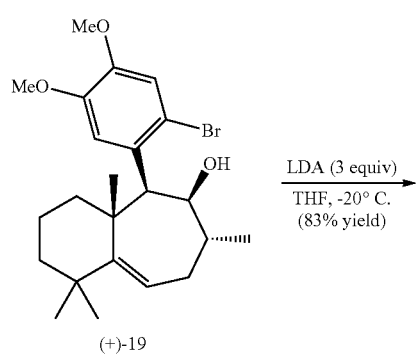
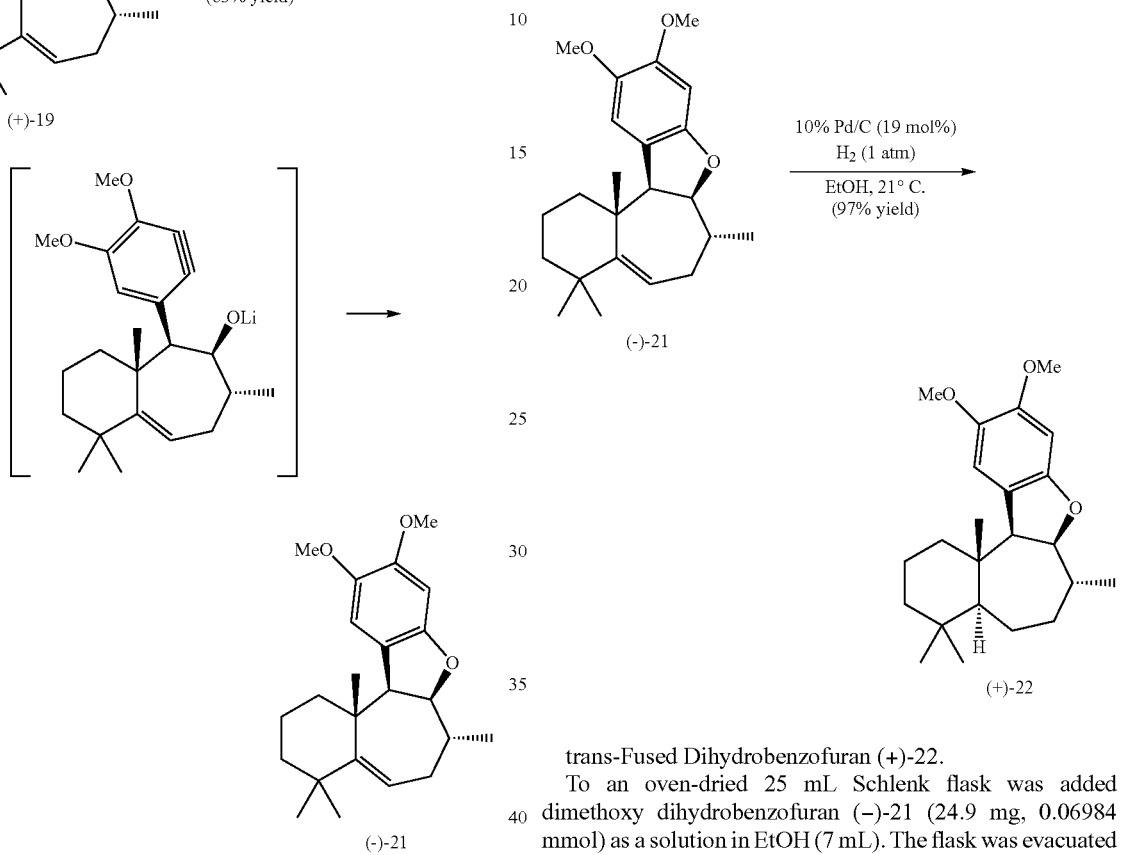

Dimethoxy dihydrobenzofuran (−)-21.

Preparation of LDA: To a solution of freshly distilled i-Pr$_2$NH (0.550 mL, 3.89 mmol) in anhydrous THF (5.4 mL) cooled to −78° C. was added ~2.2 M n-BuLi (1.60 mL, 3.52 mmol) dropwise via syringe. The contents were stirred for 30 min at −78° C. before use. This solution was titrated according to the method of Chong[5] and found to be 0.52 M.

A solution of aryl alcohol (+)-19 (36.7 mg, 0.0839 mmol) in anhydrous THF (2.8 mL) was stirred and cooled to −20° C. To this colorless solution was added freshly prepared LDA dropwise via syringe. Following completion of the reaction (20 min, monitored by TLC) it was quenched with H$_2$O (one drop) at −20° C. and allowed to warm to 22° C. The crude reaction was filtered through Celite®, concentrated in vacuo, and purified by flash column chromatography on silica gel (10:90→20:80 EtOAc:hexanes) yielding dimethoxy dihydrobenzofuran (−)-21 (25.0 mg, 83% yield) as a white solid. R$_f$=0.56 (20:80 EtOAc:hexanes); $^1$H NMR (CDCl$_3$, 500 MHz, 7.26 ppm for CHCl$_3$ in CDCl$_3$): δ=6.79 (s, 1H), 6.48 (s, 1H), 5.76 (dd, J$_1$=2.2 Hz, J$_2$=8.5 Hz, 1H), 4.18 (dd, J$_1$=7.1 Hz, J$_2$=10.8 Hz, 1H), 3.84 (s, 3H), 3.82 (s, 3H), 3.09 (d, J=7.1 Hz, 1H), 2.61 (m, 1H), 2.20-1.99 (m, 2H), 1.74-1.56 (m, 2H), 1.53-1.43 (m, 2H), 1.32 (m, 2H), 1.12 (d, J=6.5 Hz, 3H), 1.11 (s, 3H), 1.11 (s, 3H), 1.09 (s, 3H); $^{13}$C NMR (CDCl$_3$, 125 MHz, 77.2 ppm for CDCl$_3$): δ=155.7, 152.8, 150.0, 142.4, 121.9, 120.0, 113.7, 95.7, 95.0, 57.5, 56.2, 56.1, 41.5, 40.6, 39.2, 38.0, 34.6, 34.2, 33.6, 32.3, 22.9, 21.2, 17.9; IR (NaCl, cm$^{-1}$): v=3056, 2953, 2929, 2868, 2846, 1618, 1496, 1454, 1396, 1376, 1349, 1340, 1298, 1224, 1191, 1166, 1103, 989, 822; HRMS (FAB+) m/z: C$_{23}$H$_{32}$O$_3$[M]$^{+•}$: calc'd 356.2352. found 356.2359; [α]$^{25}_D$=−99.55° (c=1.25, CHCl$_3$), >99% ee.

trans-Fused Dihydrobenzofuran (+)-22.

To an oven-dried 25 mL Schlenk flask was added dimethoxy dihydrobenzofuran (−)-21 (24.9 mg, 0.06984 mmol) as a solution in EtOH (7 mL). The flask was evacuated and backfilled with N$_2$ (3×) before addition of Pd/C (14.4 mg, 0.01353 mmol, 10 wt. %, 19 mol %). The rubber septum was replaced under a positive N$_2$ flow by a three-way Teflon stopcock connected to a H$_2$ balloon. The heterogeneous mixture was cooled to −78° C. before it was evacuated and backfilled with H$_2$ (3×). The −78° C. cold bath was removed and the reaction was allowed to warm to 21° C. After stirring for 12 h the contents of the flask were filtered, concentrated in vacuo, and purified by flash column chromatography on silica gel (10:90 EtOAc:hexanes) affording trans-fused dihydrobenzofuran (+)-22 (24.3 mg, 97% yield) as a white solid. R$_f$=0.53 (10:90 EtOAc:hexanes); $^1$H NMR (CDCl$_3$, 500 MHz, 7.26 ppm for CHCl$_3$ in CDCl$_3$): δ=6.82 (s, 1H), 6.44 (s, 1H), 4.15 (dd, J$_1$=7.7 Hz, J$_2$=10.0 Hz, 1H), 3.83 (s, 3H), 3.82 (s, 3H), 2.79 (d, J=7.6 Hz, 1H), 2.25 (m, 1H), 2.02 (m, 1H), 1.66 (m, 2H), 1.55 (m, 1H), 1.39 (m, 3H), 1.29-1.16 (m, 3H), 1.14 (d, J=6.5 Hz, 3H), 1.00 (dd, J$_1$=2.4 Hz, J$_2$=12.1 Hz, 1H), 0.94 (s, 3H), 0.83 (s, 3H), 0.80 (s, 3H); $^{13}$C NMR (CDCl$_3$, 125 MHz, 77.2 ppm for CDCl$_3$): δ=155.2, 149.9, 142.2, 119.5, 114.1, 95.7, 94.7, 59.9, 57.7, 57.5, 56.1, 43.2, 40.9, 40.7, 37.7, 35.0, 34.1, 34.1, 28.1, 23.1, 22.2, 18.3, 16.3; IR (NaCl, cm$^{-1}$): v=2949, 2928, 2868, 2845, 1618, 1496, 1464, 1453, 1389, 1340, 1224, 1193, 1167, 1121, 1099, 987; HRMS (FAB+) m/z: C$_{23}$H$_{34}$O$_3$[M]$^{+•}$: calc'd 358.2508. found 358.2509; [α]$^{25}_D$=+40.47° (c=1.03, CHCl$_3$), >99% ee.

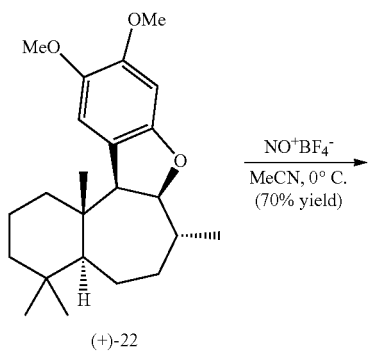

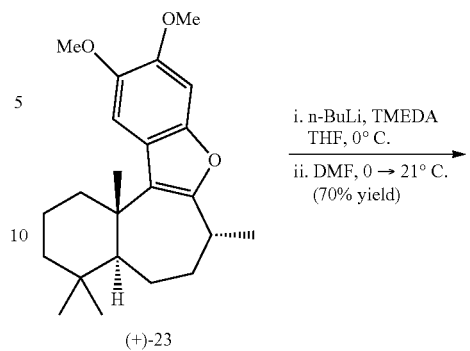

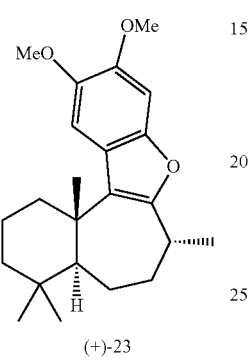

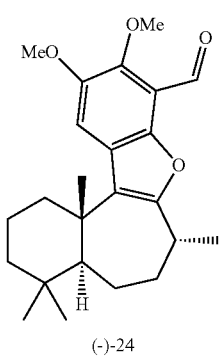

Dimethoxybenzofuran (+)-23.

To a solution of trans-fused dihydrobenzofuran (+)-22 (5.4 mg, 0.0150 mmol) in anhydrous MeCN at 0° C. was added dropwise a freshly prepared 0.128 mg/μl solution of NO$^+$BF$_4^-$ (20 μl, 0.0219 mmol) in anhydrous MeCN. The reaction solution turned brown following addition of the NO$^+$BF$_4^-$ solution, however this color slowly faded. Analysis of the mixture by LC/MS indicated that trans-fused dihydrobenzofuran (+)-22 remained. Additional NO$^+$BF$_4^-$ (150 μl, 0.164 mmol) was added at 0° C., however analysis of the mixture by LC/MS again indicated that trans-fused dihydrobenzofuran (+)-22 remained. A final aliquot of NO$^+$BF4$^-$ (75 μl, 0.083 mmol) was added at 0° C. before the reaction was quenched by the addition of urea (40 mg, 0.67 mmol) and H$_2$O (100 μl). The reaction solution was diluted with EtOAc, filtered through Celite®, and concentrated in vacuo. The residue was purified by flash pipette chromatography on silica gel (5:95 EtOAc:hexanes) providing dimethoxybenzofuran (+)-23 (3.7 mg, 70% yield) as a white solid. R$_f$=0.53 (20:80 EtOAc:hexanes); $^1$H NMR (CDCl$_3$, 500 MHz, 7.26 ppm for CHCl$_3$ in CDCl$_3$): δ=7.16 (s, 1H), 6.93 (s, 1H), 3.91 (s, 3H), 3.89 (s, 3H), 3.18 (sext, J=7.0 Hz, 1H), 2.60 (m, 1H), 2.16 (m, 1H), 1.84 (m, 1H), 1.73 (m, 1H), 1.66-1.44 (m, 6H), 1.41 (d, J=7.1 Hz, 3H), 1.38 (s, 3H), 1.26 (m, 1H), 0.98 (s, 3H), 0.95 (s, 3H); $^{13}$C NMR (CDCl$_3$, 125 MHz, 77.2 ppm for CDCl$_3$): δ=156.0, 148.6, 147.0, 145.0, 125.5, 120.5, 105.7, 95.1, 57.2, 56.3, 53.8, 42.2, 40.5, 39.7, 35.4, 35.0, 33.9, 33.5, 24.5, 22.2, 22.1, 20.4, 19.1; IR (NaCl, cm$^{-1}$): v=2930, 2867, 1623, 1488, 1466, 1439, 1389, 1316, 1281, 1211, 1197, 1166, 1136, 1115; HRMS (EI+) m/z: C$_{23}$H$_{32}$O$_3$[M]$^+$: calc'd 356.2352. found 356.2353; [α]$^{25}_D$=+16.85° (c=0.16, CHCl$_3$), >99% ee.

O,O'-Dimethyliphagal (−)-24.

Preparation of n-BuLi.TMEDA: To a stirred solution of TMEDA (380 μl, 2.5 mmol) in anhydrous THF (5 mL) was added a ~2.0 M solution of n-BuLi (1.20 mL, 2.4 mmol) at 21° C. The contents stirred for 30 min prior to use. This solution was titrated according to the method of Chong[5] and found to be 0.33 M.

A two dram vial containing dimethoxybenzofuran (+)-23 (3.7 mg, 0.01037 mmol) in anhydrous THF (500 μl) was cooled to 0° C. before dropwise addition of n-BuLi.TMEDA (80 μl, 0.0264 mmol). After stirring for 30 min at 0° C. DMF (7.5 μl, 0.0972 mmol) was introduced and the reaction was allowed to warm to 21° C. After 20 min the reaction was quenched by the addition of sat. aq NH$_4$Cl (25 mL) and filtered through MgSO$_4$ prior to HPLC purification (Zorbax Rx-Sil, 5 μm, 9.4×250 mm, 5:95 EtOAc:hexanes, 6 mL/min, monitored at 254 nm) providing O,O'-dimethyliphagal (−)-24 (2.8 mg, 70% yield) as a faint yellow solid. R$_f$=0.50 (20:80 EtOAc:hexanes); NMR (CDCl$_3$, 500 MHz, 7.26 ppm for CHCl$_3$ in CDCl$_3$): δ=10.56 (s, 1H), 7.47 (s, 1H), 3.97 (s, 3H), 3.93 (s, 3H), 3.31 (sext, J=7.0 Hz, 1H), 2.55 (m, 1H), 2.18 (dddd, J$_1$=3.3 Hz, J$_2$=7.2 Hz, J$_3$=7.2 Hz, J$_4$=12.8 Hz, 1H), 1.85 (m, 1H), 1.74 (m, 1H), 1.64-1.48 (m, 6H), 1.46 (d, J=7.2 Hz, 3H), 1.37 (s, 3H), 1.26 (ddd, J$_1$=2.8 Hz, J$_2$=13.5 Hz, J$_3$=13.5 Hz, 1H), 0.99 (s, 3H), 0.96 (s, 3H); $^{13}$C NMR (CDCl$_3$, 125 MHz, 77.2 ppm for CDCl$_3$): δ=188.6, 159.1, 149.7, 148.1, 146.5, 125.5, 124.8, 115.0, 113.3, 63.0, 57.5, 53.7, 42.1, 40.5, 39.7, 35.0, 35.0, 33.7, 33.5, 24.2, 22.3, 22.2, 20.4, 19.1; IR (NaCl, cm$^{-1}$): v=2933, 2866, 1690, 1606, 1584, 1464, 1435, 1388, 1330, 1240, 1124, 1054, 979; HRMS (MM: ESI-APCI+) m/z: C$_{24}$H$_{33}$O$_4$[M+H]$^+$: calc'd 385.2373. found 385.2371; [α]$^{25}_D$=−16.36° (c=0.280, CHCl$_3$), >99% ee.[6]

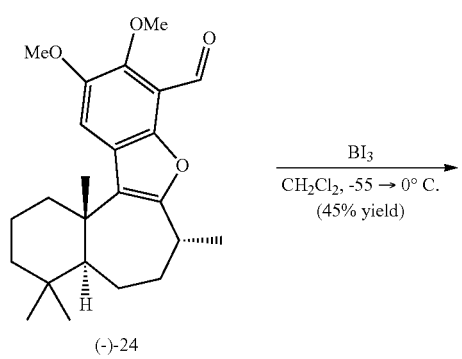

(−)-24

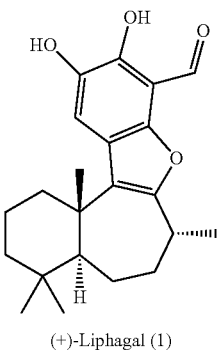

(+)-Liphagal (1)

Liphagal (+)-1.

In the glovebox[4], a two dram vial containing 0, O'-dimethyliphagal (−)-24 (1.7 mg, 0.00442 mmol) dissolved in anhydrous CH$_2$Cl$_2$ (680 μl) was cooled to −55° C. before addition of a freshly prepared 0.01M solution of BI$_3$ (885 μl, 0.00885 mmol) in anhydrous CH$_2$Cl$_2$. After 5 min at −55° C. the vial was warmed to 0° C. over 45 min. After 20 min at 0° C. the vial was removed from the glovebox and immediately quenched with H$_2$O:MeCN (50 μL:300 μL) resulting in a cloudy mixture. The volatiles were removed under a stream of Ar. The yellow residue was dissolved in MeCN, filtered through a Kimwipe® plug, and purified by reversed-phase HPLC (Eclipse XDB-C18, 5 μm, 9.4×250 mm, 80:20 MeCN: 0.1% AcOH/H$_2$O, 5 mL/min, monitored at 254 nm) yielding liphagal (+)-1 (0.7 mg, 45% yield) as a yellow oil/film. Retention time: liphagal (+)-1 ~21 min. R$_f$=0.58 (20:80 EtOAc: hexanes+1% AcOH); $^1$H NMR (CDCl$_3$, 600 MHz, 7.26 ppm for CHCl$_3$ in CDCl$_3$): δ=11.24 (s, 1H), 10.45 (s, 1H), 7.55 (s, 1H), 5.30 (s, 1H), 3.22 (sext, J=7.0 Hz, 1H), 2.54 (m, 1H), 2.18 (dddd, J$_1$=3.5 Hz, J$_2$=6.4 Hz, J$_3$=6.4 Hz, J$_4$=13.1 Hz, 1H), 1.87 (m, 1H), 1.71 (m, 1H), 1.65-1.45 (m, 6H), 1.43 (d, J=7.1 Hz, 3H), 1.35 (s, 3H), 1.25 (ddd, J$_1$=3.1 Hz, J$_2$=13.3 Hz, J$_3$=13.3 Hz, 1H), 0.98 (s, 3H), 0.95 (s, 3H); $^{13}$C NMR (CDCl$_3$, 125 MHz, 77.2 ppm for CDCl$_3$): δ=192.7, 156.7, 148.2, 145.5, 139.6, 125.7, 120.5, 116.2, 106.5, 54.0, 42.1, 40.5, 39.7, 35.4, 35.1, 33.9, 33.5, 24.4, 22.2, 21.9, 20.5, 19.0; IR (NaCl, cm$^{-1}$): v=3558, 3436, 2931, 2868, 1654, 1607, 1455, 1391, 1379, 1328, 1297, 1193; HRMS (MM: ESI-APCI+) m/z: C$_{22}$H$_{27}$O$_4$[M−H]$^-$: calc'd 355.1915. found 355.1914; [α]$^{25}_D$=+25.99° (c=0.072, CHCl$_3$), >99% ee.

Comparison of Synthetic Liphagal Prepared by Andersen and Stoltz.

The data listed for Stoltz is for the liphagal prepared according to the above examples. The data listed for Andersen is for the liphagal prepared according to the procedure discussed in Marion, et al., "Liphagal, a Selective Inhibitor of PI3 Kinase α Isolated from the Sponge Aka coralliphaga: Struture Elucidation and Biomimetic Synthesis," Org. Lett., vol. 8, no. 2, pgs. 321-324, the entire content of which has already been incorporated herein by reference.

| $^1$H NMR of (+)-Liphagal, CDCl$_3$[1] | | | |
|---|---|---|---|
| Synthetic, 400 MHz Andersen | | Synthetic (+), 600 MHz Stoltz | |
| Shift (ppm) | Multiplicity/Coupling (Hz) | Shift (ppm) | Multiplicity/Coupling (Hz) |
| 11.24 | s | 11.24 | s |
| 10.45 | s | 10.45 | s |
| 7.55 | s | 7.55 | s |
| 5.32 | br s | 5.30 | s |
| 3.20 | m | 3.22 | sext, 7.0 |
| 2.54 | m | 2.54 | m |
| 2.17 | m | 2.18 | dddd, 3.5, 6.4, 6.4, 13.1 |
| 1.86 | m | 1.87 | m |
| — | — | 1.71 | m |
| 1.8-1.5 | m | 1.65-1.45 | m |
| 1.43 | d, 7.0 | 1.43 | d, 7.1 |
| 1.34 | s | 1.35 | s |
| 1.25 | m | 1.25 | ddd, 3.1, 13.3, 13.3 |
| 0.98 | s | 0.98 | s |
| 0.95 | s | 0.95 | s |

1. The values for Andersen's Synthetic Liphagal have been referenced to residual CHCl$_3$ in CDCl$_3$ at δ = 7.26

| $^{13}$C NMR of (+)-Liphagal, CDCl$_3$[1] | |
|---|---|
| Synthetic, 400 MHz Andersen Shift (ppm) | Synthetic (+), 500 MHz Stoltz Shift (ppm) |
| 192.6 | 192.7 |
| 156.7 | 156.7 |
| 148.1 | 148.2 |

-continued

$^{13}$C NMR of (+)-Liphagal, CDCl$_3$[1]

| Synthetic, 400 MHz Andersen Shift (ppm) | Synthetic (+), 500 MHz Stoltz Shift (ppm) |
|---|---|
| 145.5 | 145.5 |
| 139.6 | 139.6 |
| 125.7 | 125.7 |
| 120.5 | 120.5 |
| 116.1 | 116.2 |
| 106.4 | 106.5 |
| 53.9 | 54.0 |
| 42.1 | 42.1 |
| 40.4 | 40.5 |
| 39.6 | 39.7 |
| 35.3 | 35.4 |
| 35.0 | 35.1 |
| 33.8 | 33.9 |
| 33.5 | 33.5 |
| 24.3 | 24.4 |
| 22.1 | 22.2 |
| 21.8 | 21.9 |
| 20.4 | 20.5 |
| 18.9 | 19.0 |

1. The values for Andersen's Synthetic Liphagal have been referenced to CDCl$_3$ at δ = 77.2

Methods for the Determination of Enantiomeric Excess.

| Entry | Substrate | Assay | Column | Method | Retention Time (min) | | |
|---|---|---|---|---|---|---|---|
| 1. | (R)-(+)-5 | Enantiomeric Excess | Chiral HPLC | 3% EtOH/Hex monitor@254 nm | Major (R) | 9.1 | |
| | | | Chiralcel AD Column | 20 min | Minor (S) | 10.2 | |
| 2. | (R)-(+)-15 | Enantiomeric Excess | Chiral SFC | 30% IPA/scCO$_2$ monitor@235/244 nm | Major (R) | 4.6 | |
| | | | Chiralcel AD-H Column | 10 min | Minor (S) | 7.3 | |

While the present invention has been illustrated and described with reference to certain exemplary embodiments, those of ordinary skill in the art will understand that various modifications and changes may be made to the described embodiments without departing from the spirit and scope of the preset invention, as defined in the following claims.

What is claimed is:

1. A method for preparing a compound of Formula 17A:

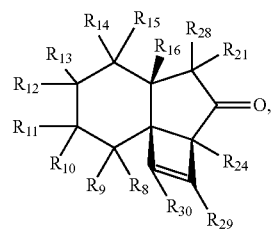
(17A)

comprising treating a compound of Formula 17B:

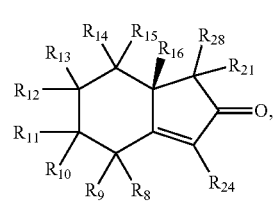
(17B)

under [2+2] photocycloaddition conditions with a compound represented by the Formula (I):

(1)

wherein:
R$_8$-R$_{16}$ and R$_{24}$ are independently selected from hydrogen, alkyl group and carbonyl group;

$R_{21}$ and $R_{28}$ are hydrogen; and
$R_{29}$ and $R_{30}$ are independently hydrogen or trialkylsilyl group.

2. A method for preparing a compound of Formula 18A:

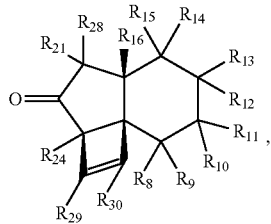
(18A)

comprising treating a compound of Formula 18B:

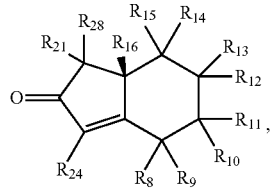
(18B)

under [2+2] photocycloaddition conditions with a compound represented by the Formula (I):

 (1)

wherein:

$R_8$-$R_{16}$ and $R_{24}$ are independently hydrogen or an alkyl group;

$R_{21}$ and $R_{28}$ are hydrogen; and $R_{29}$ and $R_{30}$ are independently hydrogen or trialkylsilyl group.

3. The method of claim 1 or 2, wherein $R_{24}$ is hydrogen.

4. The method of claim 1 or 2, wherein the compound of Formula (I) is trimethylsilyl acetylene.

5. The method of claim 1 or 2, wherein the photocycloaddition conditions comprise UV radiation.

6. The method of claim 1 or 2, wherein the UV radiation comprises UVB radiation.

7. The method of claim 1 or 2, wherein the photocycloaddition conditions comprise a solvent.

8. The method of claim 7, wherein the solvent comprises acetone.

9. The method of claim 1 or 2, wherein the method further comprises treating a compound of Formula 17A or 17B with a Lewis acid.

* * * * *